(12) United States Patent
Ausubel et al.

(10) Patent No.: US 9,301,940 B2
(45) Date of Patent: Apr. 5, 2016

(54) METHODS FOR SCREENING ANTIMICROBIAL AND ANTIVIRAL COMPOUNDS AND USES THEREOF

(75) Inventors: Frederick M. Ausubel, Newton, MA (US); Kim Lewis, Newton, MA (US); Terence I. Moy, Wayland, MA (US); Suresh Gopalan, Lexington, MA (US)

(73) Assignees: The General Hospital Corporation, Boston, MA (US); Northeastern University, Boston, MA (US)

( * ) Notice: Subject to any disclaimer, the term of this patent is extended or adjusted under 35 U.S.C. 154(b) by 1321 days.

(21) Appl. No.: 12/304,963

(22) PCT Filed: Jun. 18, 2007

(86) PCT No.: PCT/US2007/014127
§ 371 (c)(1),
(2), (4) Date: Nov. 25, 2009

(87) PCT Pub. No.: WO2008/066576
PCT Pub. Date: Jun. 5, 2008

(65) Prior Publication Data
US 2010/0216852 A1    Aug. 26, 2010

Related U.S. Application Data

(60) Provisional application No. 60/814,465, filed on Jun. 16, 2006, provisional application No. 60/872,168, filed on Dec. 1, 2006.

(51) Int. Cl.
*A61K 31/221* (2006.01)
*A61K 31/426* (2006.01)
*C12Q 1/18* (2006.01)

(52) U.S. Cl.
CPC ............. *A61K 31/221* (2013.01); *A61K 31/426* (2013.01); *C12Q 1/18* (2013.01)

(58) Field of Classification Search
None
See application file for complete search history.

(56) References Cited

U.S. PATENT DOCUMENTS 6,706,766 B2 *  3/2004  Yuan et al. .................... 514/617
6,904,423 B1     6/2005  Nicolaou et al.

OTHER PUBLICATIONS

Moy et al. "Identification of Novel Antimicrobials Using a Live-Animal Infection Model". PNAS, Jul. 5, 2006; 103(27):10414-10419.*

Pilger et al. "Identification of a Small Molecule that Inhibits Herpes Simplex Virus DNA Polymerase Subunit Interactions and Viral Replication". Chemistry & Biology. 2004; 11:647-654.*
Leibovici et al. "The Benefit of Appropriate Empirical Antibiotic Treatment in Patients with Bloodstream Infection". Journal of Internal Medicine. 1998; 244:379-386.*
Zaragoza et al. "The Influence of Inadequate Empirical Antimicrobial Treatment on Patients with Bloodstream Infections in an Intensive Care Unit". Clin Microbiol Infect. 2003; 9:412-418.*
Blot et al. "Colonization Status and Appropriate Antibiotic Therapy for Nosocomial Bacteremia Caused by Antibiotic-Resistant Gram-Negative Bacteria in an Intensive Care Unit". Infect Control Hosp Epidemiol, 2005; 26:575-579.*
Kim et al. "*Staphylococcus aureus* Bacteremia: Using Echocardiography to Guide Length of Therapy". Cleveland Clinic Journal of Medicine. 2003; 70(6):517-533.*
Kang et al. "Bloodstream Infections due to Extended-Spectrum Beta-Lactamase-Producing *Escherichia coli* and *Klebsiella pneumoniae*: Risk Factors for Mortality and Treatment Outcome, with Special Emphasis on Antimicrobial Therapy". Antimicrob. Agents Chemother. 2004; 48(12):4574-4581.*
Chamot et al. "Effectiveness of Combination Antimicrobial Therapy for *Pseudomonas aeruginosa* Bacteremia". Antimicrob. Agents Chemother. 2003; 47(9):2756-2764.*
Peter et al. "The Yucatan Micropig as an Experimental Bacteremia Model". Pathol Biol. 2001; 49:576-582.*
Wang et al. "Use of Bacteriophage in the Treatment of Experimental Animal Bacteremia from Imipenem-Resistant *Pseudomonas aeruginosa*". International Journal of Molecular Medicine, 2006; 17:309-317.*
Déziel et al., "The contribution of MvfR to *Pseudomonas aeruginosa* pathogenesis and quorum sensing circuitry regulation: multiple quorum sensing-regulated genes are modulated without affecting lasRI, rhlRI or the production of N-acyl-L-homoserine lactones," *Mol. Microbiol.* 55:998-1014, 2005.
Himmel et al., "HIV-1 reverse transcriptase structure with RNase H inhibitor dihydroxy benzoyl naphthyl hydrazone bound at a novel site," *ACS Chem. Biol.* 1:702-712, 2006.
Kwok et al., "A small-molecule screen in C. elegans yields a new calcium channel antagonist," *Nature* 441:91-95, 2006.
Lehner et al., "Systematic mapping of genetic interactions in Caenorhabditis elegans identifies common modifiers of diverse signaling pathways," *Nat. Genet.* 38:896-903, 2006.
Liu et al., "Restriction of vaccinia virus replication by a ced-3 and ced-4-dependent pathway in Caenorhabditis elegans," *Proc. Natl. Acad. Sci. USA* 103:4174-4179, 2006.
McGovern et al., "A common mechanism underlying promiscuous inhibitors from virtual and high-throughput screening," *J. Med. Chem.* 45:1712-1722, 2002.
International Search Report and Written Opinion for International Application No. PCT/US07/14127, dated Sep. 17, 2008 (8 pages).

* cited by examiner

*Primary Examiner* — Leslie A. Royds Draper
(74) *Attorney, Agent, or Firm* — Clark & Elbing LLP

(57) ABSTRACT

The invention features compounds that have antibacterial activity, their use for the treatment of bacterial infections, screening methods that use whole animals or plant seedlings to identify compounds that inhibit a pathogen in the animal or plant, and screening methods to identify compounds that increase the lifespan of an organism.

2 Claims, 27 Drawing Sheets

A1

A2: Homologue Tanimoto=0.8866    A3: Homologue Tanimoto=0.8854    A4: Homologue Tanimoto=0.861

A5: Homologue Tanimoto=0.8542    A6: Homologue Tanimoto=0.9786    A7: Homologue Tanimoto=0.9105

A8: Homologue Tanimoto=0.865    A9: Homologue Tanimoto=0.9482

B1

B2: Homologue Tanimoto=0.8926

C1

C2: Homologue Tanimoto=0.9706

C3: Homologue Tanimoto=0.9545

C4: Homologue Tanimoto=0.924

C5: Homologue Tanimoto=0.924

C6: Homologue Tanimoto=0.9203

C7: Homologue Tanimoto=0.9203

D1

D2: Homologue Tanimoto=0.9684  D3: Homologue Tanimoto=0.8558  D4: Homologue Tanimoto=0.8776

E1

E2: Homologue Tanitmoto=0.9394   E3: Homologue Tanitmoto=0.9394   E4: Homologue Tanitmoto=0.9394

E5: Homologue Tanimoto=0.9265   E6: Homologue Tanimoto=0.9208   E7: Homologue Tanimoto=0.9175

E8: Homologue Tanimoto=0.9163   E9: Homologue Tanimoto=0.9163   E10: Homologue Tanimoto=0.9163

E11: Homologue Tanimoto=0.9122   E12: Homologue Tanimoto=0.9118   E13: Homologue Tanimoto=0.9118

E14: Homologue Tanimoto=0.9118   E15: Homologue Tanimoto=0.8990   E16: Homologue Tanimoto=0.8986

E17: Homologue Tanimoto=0.8986   E18: Homologue Tanimoto=0.8942   E19: Homologue Tanimoto=0.8815

E20: Homologue Tanimoto=0.8796   E21: Homologue Tanimoto=0.8779   E22: Homologue Tanimoto=0.8774

E23: Homologue Tanimoto=0.8692   E24: Homologue Tanimoto=0.8629   E25: Homologue Tanimoto=0.8532

F1

F2: Homologue Tanimoto=0.9472

F3: Homologue Tanimoto=0.8939

F4: Homologue Tanimoto=0.8868

F5: Homologue Tanimoto=0.8835

F6: Homologue Tanimoto=0.8773

F7: Homologue Tanimoto=0.8736

G1

G2: Homologue Tanimoto=0.9377

H1

H2: Homologues Tanimoto=0.8610   H3: Homologues Tanimoto=0.8973   H4: Homologues Tanimoto=0.9526

H5: Homologues Tanimoto=0.8737   H6: Homologues Tanimoto=0.8617   H7: Homologues Tanimoto=0.8783

H8: Homologues Tanimoto=0.8783

I1

I2: Homologue Tanimoto=0.8670

J1

J2: Homologue Tanimoto=0.9281

J3: Homologue Tanimoto=0.8986

J4: Homologue Tanimoto=0.8780

J5: Homologue Tanimoto=0.9535

J6: Homologue Tanimoto=0.8617 compound E30 compound F1 compound G1 compound H1 compound I1 compound J1 compound K1 compound L1 compound M1 compound N1 compound O1

METHODS FOR SCREENING ANTIMICROBIAL AND ANTIVIRAL COMPOUNDS AND USES THEREOF

CROSS-REFERENCE TO RELATED APPLICATIONS

This application is the U.S. National. Stage of International Application No. PCT/US2007/014127, filed Jun. 18, 2007, which in turn, claims the benefit of U.S. Provisional Application Nos. 60/814,465, filed Jun. 16, 2006, and 60/872,168, filed Dec. 1, 2006, each of which is incorporated by reference.

STATEMENT AS TO FEDERALLY FUNDED RESEARCH

This invention was made in part with Government funding, and the Government therefore has certain rights in the invention. In particular, portions of the invention disclosed herein were funded, in part, by NIH Grant Nos. RO1 AI070863, R21 AI059483, K08 AI63084-01, and RO1 AI072508.

BACKGROUND OF THE INVENTION

This invention relates to the field of antimicrobials and antivirals for the treatment of infections and compounds that increase longevity.

The growing problem of antibiotic resistant bacteria (see Chambers H. F., Emerg. Infect. Dis. 7:178-182 (2001); Hecht D. W., Clin. Infect. Dis. 39:92-97 (2004); Jacobs M. R., Am. J. Med. 117 Suppl. 3A:3S-15S (2004); Molbak K., Clin. Infect. Dis. 41:1613-1620 (2005); Shah et al., Res. Microbiol. 155:409-421 (2004); Wisplinghoff et al., Clin. Infect. Dis. 39:309-317 (2004); and Zinner S. H., Expert Rev. Anti. Infect. Ther. 3:907-913 (2005)) and the imminent threat of biowarfare agents (see Lane et al., Nat. Med. 7:1271-1273 (2001)) points to a need for new anti-infective therapies. However, the rate of new antimicrobial and antiviral discovery is unlikely to meet the expected need for the foreseeable future (see Boggs et al., Clin. Microbiol. Infect. 10 Suppl. 4:32-36 (2004); Bush K., Clin. Microbiol. Infect. 10 Suppl. 4:10-17 (2004); Dougherty et al., Curr. Pharm. Des. 8:1119-1135 (2002); Schmid M. B., Nat. Rev. Microbiol. 2:739-746 (2004); Silver L. L., IDrugs 8:651-655 (2005); and Walsh C., Nat. Rev. Microbiol. 1:65-70 (2003)). Specific problems include the over-mining of cultivable microorganisms (see Osburne et al., ASM News 66:411-417 (2000)), a high background of toxic compounds or compounds with poor pharmacokinetic properties in synthetic compound libraries (see Projan et al., Clin. Microbiol. Infect. 10 Suppl 4:18-22 (2004); and Lipinski et al., Nature 432:855-861 (2004)), and the inability of most synthetic leads to penetrate across the multi-drug resistance (MDR) barrier of Gram-negative bacteria (see Li et al., Drugs 64:159-204 (2004)). The increased use of in vitro assays for small-molecule discovery that bear little resemblance to the biological systems in which the drugs need to function may also be responsible for the decline in the rate of drug discovery (see Lipinski et al., Nature 432:855-861 (2004); Horrobin D. F., Nat. Rev. Drug Discov. 2:151-154 (2003); Williams M., Curr. Opin. Investig. Drugs 5:29-33 (2004)). Efforts to identify new antifungal compounds have been hindered by the fact that most compounds that have antifungal activity in vitro are also toxic to mammalian cells.

Plant pathogenic diseases are also of concern because they cause damage to plants and plant products. Phytopathogens produce disease in plants by any number of methods including: (1) consuming host cell nutrients; (2) killing or disrupting host cell metabolism through toxins, enzymes, or growth-regulators; (3) affecting photosynthesis by inducing chlorosis (e.g., by degrading chloroplasts); and (4) blocking conductive tissues and interfering with normal physiological processes.

Crop plants, ornamentals, trees, and shrubs are especially vulnerable to diseases caused by bacteria, fungi, and viruses. Phytopathogenic bacteria, for example, cause the development of many disease symptoms including leaf spots and blights, soft-rots, wilts, overgrowths, scabs, and cankers. Bacterial diseases occur most commonly on vegetables (and some ornamentals) that have fleshy storage tissues, such as potatoes, carrots, onions, iris, or hyacinth. They may also occur in plants bearing fleshy fruit (such as cucumber, squash, eggplant, or tomato), as well as in leafy plants (such as cabbage, celery, lettuce, or spinach). Plant bacterial diseases occur throughout the world and cause serious damage to crops in the field, in transit, and in storage.

A facile bioassay compatible with high throughput screening technologies that simultaneously evaluated libraries of chemical compounds for antimicrobial and antiviral activity and host toxicity in the context of a live-animal, or plant seedling, infection model could solve some of the main obstacles in current antimicrobial discovery. There is a need in the art for the development of new antimicrobial and antiviral compounds.

SUMMARY OF THE INVENTION

We have discovered compounds that have antibacterial activity. These compounds can be useful for the treatment of bacterial infection in animals and plants. In addition, we discovered a screening method that uses whole animals or plant seedlings to identify compounds that inhibit a pathogen in the animal or plant seedling. The screening method can also be used to identify compounds that increase longevity of an organism.

The invention features a pharmaceutical composition including a compound of formula (I), or a salt thereof, and a pharmaceutically acceptable excipient.

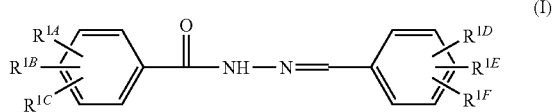

(I)

In formula (I) each of $R^{1A}$, $R^{1B}$, $R^{1C}$, $R^{1D}$, $R^{1E}$, and $R^{1F}$ is, independently, selected from H, halide, nitro, $C_{1-4}$ alkyl, $C_{2-4}$ alkenyl, $C_{2-4}$ alkynyl, $OR^{1G}$, $OC(O)R^{1H}$, $NR^{1I}R^{1J}$, $NHC(O)R^{1K}$, $NHC(S)R^{1L}$, $NHC(O)OR^{1M}$, $NHC(S)OR^{1N}$, $NHC(O)NHR^{1O}$, $NHC(S)NHR^{1P}$, $NHC(O)SR^{1Q}$, $NHC(S)SR^{1R}$, $NHS(O)_2R^{1S}$, $C(O)OR^{1T}$, and $C(O)NHR^{1U}$; and each of $R^{1G}$, $R^{1H}$, $R^{1I}$, $R^{1J}$, $R^{1K}$, $R^{1L}$, $R^{1M}$, $R^{1N}$, $R^{1O}$, $R^{1P}$, $R^{1Q}$, $R^{1R}$, $R^{1S}$, $R^{1T}$, and $R^{1U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. In one particular embodiment, $R^{1A}$ and $R^{1D}$ are H; each of $R^{1B}$, $R^{1C}$, $R^{1E}$, and $R^{1F}$ is, independently, selected from H, halide, nitro, $C_{1-4}$ alkyl, $C_{2-4}$ alkenyl, $C_{2-4}$ alkynyl, $OR^{1G}$, $OC(O)R^{1H}$, $NR^{1I}R^{1J}$, $NHC(O)R^{1K}$, $NHC(S)R^{1L}$, $NHC(O)OR^{1M}$, $NHC(S)OR^{1N}$, $NHC(O)NHR^{1O}$, $NHC(S)NHR^{1P}$, $NHC(O)SR^{1Q}$, $NHC(S)SR^{1R}$, $NHS(O)_2R^{1S}$, $C(O)OR^{1T}$, and $C(O)NHR^{1U}$; and each of $R^{1G}$, $R^{1H}$, $R^{1I}$, $R^{1J}$, $R^{1K}$, $R^{1L}$, $R^{1M}$, $R^{1N}$, $R^{1O}$, $R^{1P}$, $R^{1Q}$, $R^{1R}$, $R^{1S}$, $R^{1T}$, and $R^{1U}$ is, independently, selected from H, $C_{1-4}$ alkyl, $C_{2-4}$ alkenyl, $C_{2-4}$ alkynyl, and $C_{1-4}$ heteroalkyl.

The invention further features a pharmaceutical composition including a compound of formula (II), or a salt thereof, and a pharmaceutically acceptable excipient.

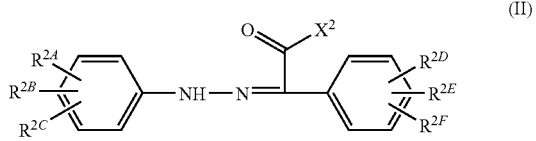

(II)

In formula (II) each of $R^{2A}$, $R^{2B}$, $R^{2C}$, $R^{2D}$, $R^{2E}$, and $R^{2F}$ is, independently, selected from H, halide, nitro, $C_{1-4}$ alkyl, $C_{2-4}$ alkenyl, $C_{2-4}$ alkynyl, $OR^{2G}$, $OC(O)R^{2H}$, $NR^{2I}R^{2J}$, $NHC(O)R^{2K}$, $NHC(S)R^{2L}$, $NHC(O)OR^{2M}$, $NHC(S)OR^{2N}$, $NHC(O)NHR^{2O}$, $NHC(S)NHR^{2P}$, $NHC(O)SR^{2Q}$, $NHC(S)SR^{2R}$, $NHS(O)_2R^{2S}$, $C(O)OR^{2T}$, and $C(O)NHR^{2U}$; $X^2$ is independently selected from $OR^{2G}$, $OC(O)R^{2H}$, $NR^{2I}R^{2J}$, $NHC(O)R^{2K}$, $NHC(S)R^{2L}$, $NHC(O)OR^{2M}$, $NHC(S)OR^{2N}$, $NHC(O)NHR^{2O}$, $NHC(S)NHR^{2P}$, $NHC(O)SR^{2Q}$, $NHC(S)SR^{2R}$, and $NHS(O)_2R^{2S}$; and each of $R^{2G}$, $R^{2H}$, $R^{2I}$, $R^{2J}$, $R^{2K}$, $R^{2L}$, $R^{2M}$, $R^{2N}$, $R^{2O}$, $R^{2P}$, $R^{2Q}$, $R^{2R}$, $R^{2S}$, $R^{2T}$, and $R^{2U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. In one particular embodiment, $R^{2A}$ and $R^{2D}$ are H; each of $R^{2B}$, $R^{2C}$, $R^{2E}$, and $R^{2F}$ is, independently, selected from H, halide, nitro, $C_{1-4}$ alkyl, $C_{2-4}$ alkenyl, $C_{2-4}$ alkynyl, $OR^{2G}$, $OC(O)R^{2H}$, $NR^{2I}R^{2J}$, $NHC(O)R^{2K}$, $NHC(S)R^{2L}$, $NHC(O)OR^{2M}$, $NHC(S)OR^{2N}$, $NHC(O)NHR^{2O}$, $NHC(S)NHR^{2P}$, $NHC(O)SR^{2Q}$, $NHC(S)SR^{2R}$, $NHS(O)_2R^{2S}$, $C(O)OR^{2T}$, and $C(O)NHR^{2U}$; $X^2$ is independently selected from $OR^{2G}$, $OC(O)R^{2H}$, $NR^{2I}R^{2J}$, $NHC(O)R^{2K}$, $NHC(S)R^{2L}$, $NHC(O)OR^{2M}$, $NHC(S)OR^{2N}$, $NHC(O)NHR^{2O}$, $NHC(S)NHR^{2P}$, $NHC(O)SR^{2Q}$, $NHC(S)SR^{2R}$, and $NHS(O)_2R^{2S}$; and each of $R^{2G}$, $R^{2H}$, $R^{2I}$, $R^{2J}$, $R^{2K}$, $R^{2L}$, $R^{2M}$, $R^{2N}$, $R^{2O}$, $R^{2P}$, $R^{2Q}$, $R^{2R}$, $R^{2S}$, $R^{2T}$, and $R^{2U}$ is, independently, selected from H, $C_{1-4}$ alkyl, $C_{2-4}$ alkenyl, $C_{2-4}$ alkynyl, $C_{2-6}$ heterocyclyl, and $C_{1-4}$ heteroalkyl.

The invention also features a pharmaceutical composition including a compound of formula (III), or a salt thereof, and a pharmaceutically acceptable excipient.

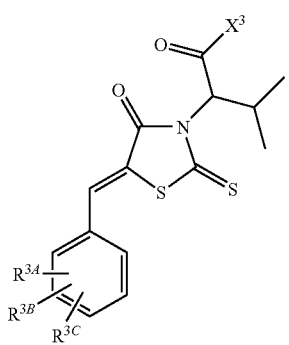

(III)

In formula (III) each of $R^{3A}$, $R^{3B}$, and $R^{3C}$ is, independently, selected from H, halide, nitro, $C_{1-4}$ alkyl, $C_{2-4}$ alkenyl, $C_{2-4}$ alkynyl, $OR^{3G}$, $OC(O)R^{3H}$, $NR^{3I}R^{3J}$, $NHC(O)R^{3K}$, $NHC(S)R^{3L}$, $NHC(O)OR^{3M}$, $NHC(S)OR^{3N}$, $NHC(O)NHR^{3O}$, $NHC(S)NHR^{3P}$, $NHC(O)SR^{3Q}$, $NHC(S)SR^{3R}$, $NHS(O)_2R^{3S}$, $C(O)OR^{3T}$, and $C(O)NHR^{3U}$; $X^3$ is independently selected from $OR^{3G}$, $OC(O)R^{3H}$, $NR^{3I}R^{3J}$, $NHC(O)R^{3K}$, $NHC(S)R^{3L}$, $NHC(O)OR^{3M}$, $NHC(S)OR^{3N}$, $NHC(O)NHR^{3O}$, $NHC(S)NHR^{3P}$, $NHC(O)SR^{3Q}$, $NHC(S)SR^{3R}$, and $NHS(O)_2R^{3S}$; and each of $R^{3G}$, $R^{3H}$, $R^{3I}$, $R^{3J}$, $R^{3K}$, $R^{3L}$, $R^{3M}$, $R^{3N}$, $R^{3O}$, $R^{3P}$, $R^{3Q}$, $R^{3R}$, $R^{3S}$, $R^{3T}$, and $R^{3U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. In one particular embodiment, $R^{3A}$ is H; each of $R^{3B}$ and $R^{3C}$ is, independently, selected from H, halide, nitro, $C_{1-4}$ alkyl, $C_{2-4}$ alkenyl, $C_{2-4}$ alkynyl, $OR^{3G}$, $OC(O)R^{3H}$, $NR^{3I}R^{3J}$, $NHC(O)R^{3K}$, $NHC(S)R^{3L}$, $NHC(O)OR^{3M}$, $NHC(S)OR^{3N}$, $NHC(O)NHR^{3O}$, $NHC(S)NHR^{3P}$, $NHC(O)SR^{3Q}$, $NHC(S)SR^{3R}$, $NHS(O)_2R^{3S}$, $C(O)OR^{3T}$, and $C(O)NHR^{3U}$; $X^3$ is independently selected from $OR^{3G}$, $OC(O)R^{3H}$, $NR^{3I}R^{3J}$, $NHC(O)R^{3K}$, $NHC(S)R^{3L}$, $NHC(O)OR^{3M}$, $NHC(S)OR^{3N}$, $NHC(O)NHR^{3O}$, $NHC(S)NHR^{3P}$, $NHC(O)SR^{3Q}$, $NHC(S)SR^{3R}$, and $NHS(O)_2R^{3S}$; and each of $R^{3G}$, $R^{3H}$, $R^{3I}$, $R^{3J}$, $R^{3K}$, $R^{3L}$, $R^{3M}$, $R^{3N}$, $R^{3O}$, $R^{3P}$, $R^{3Q}$, $R^{3R}$, $R^{3S}$, $R^{3T}$, and $R^{3U}$ is, independently, selected from H, $C_{1-4}$ alkyl, $C_{2-4}$ alkenyl, $C_{2-4}$ alkynyl, and $C_{1-4}$ heteroalkyl.

The invention features a pharmaceutical composition including a compound of formula (IV), or a salt thereof, and a pharmaceutically acceptable excipient.

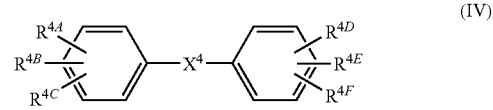

(IV)

In formula (IV) each of $R^{4A}$, $R^{4B}$, $R^{4C}$, $R^{4D}$, $R^{4E}$, and $R^{4F}$ is, independently, selected from H, halide, nitro, $C_{1-4}$ alkyl, $C_{2-4}$ alkenyl, $C_{2-4}$ alkynyl, $OR^{4G}$, $OC(O)R^{4H}$, $NR^{4I}R^{4J}$, $NHC(O)R^{4K}$, $NHC(S)R^{4L}$, $NHC(O)OR^{4M}$, $NHC(S)OR^{4N}$, $NHC(O)NHR^{4O}$, $NHC(S)NHR^{4P}$, $NHC(O)SR^{4Q}$, $NHC(S)SR^{4R}$, $NHS(O)_2R^{4S}$, $C(O)OR^{4T}$, and $C(O)NHR^{4U}$; $X^4$ is —S(O)— or —S(O)$_2$—; and each of $R^{4G}$, $R^{4H}$, $R^{4I}$, $R^{4J}$, $R^{4K}$, $R^{4L}$, $R^{4M}$, $R^{4N}$, $R^{4O}$, $R^{4P}$, $R^{4Q}$, $R^{4R}$, $R^{4S}$, $R^{4T}$, and $R^{4U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. In one particular embodiment, $R^{4A}$ and $R^{4D}$ are H; each of $R^{4B}$, $R^{4C}$, $R^{4E}$, and $R^{4F}$ is, independently, selected from H, halide, nitro, $C_{1-4}$ alkyl, $C_{2-4}$ alkenyl, $C_{2-4}$ alkynyl, $OR^{4G}$, $OC(O)R^{4H}$, $NR^{4I}R^{4J}$, $NHC(O)R^{4K}$, $NHC(S)R^{4L}$, $NHC(O)OR^{4M}$, $NHC(S)OR^{4N}$, $NHC(O)NHR^{4O}$; $NHC(S)NHR^{4P}$, $NHC(O)SR^{4Q}$, $NHC(S)SR^{4R}$, $NHS(O)_2R^{4S}$, $C(O)OR^{4T}$, and $C(O)NHR^{4U}$; $X^4$ is —S(O)— or —S(O)$_2$—; and each of $R^{4G}$, $R^{4H}$, $R^{4I}$, $R^{4J}$, $R^{4K}$, $R^{4L}$, $R^{4M}$, $R^{4N}$, $R^{4O}$, $R^{4P}$, $R^{4Q}$, $R^{4R}$, $R^{4S}$, $R^{4T}$, and $R^{4U}$ is, independently, selected from H, $C_{1-4}$ alkyl, $C_{2-4}$ alkenyl, $C_{2-4}$ alkynyl, and $C_{1-4}$ heteroalkyl.

The invention further features a pharmaceutical composition including a compound of formula (V), or a salt thereof, and a pharmaceutically acceptable excipient.

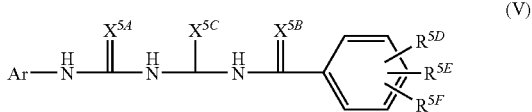

(V)

In formula (V) Ar is

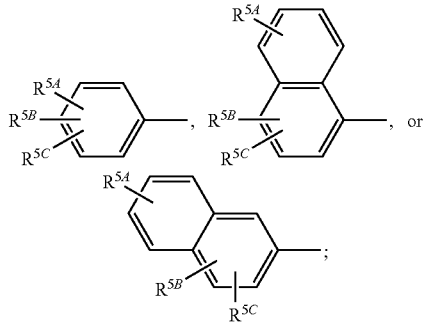

each of $R^{5A}$, $R^{5B}$, $R^{5C}$, $R^{5D}$, $R^{5E}$, and $R^{5F}$ is, independently, selected from H, halide, nitro, $C_{1-4}$ alkyl, $C_{2-4}$ alkenyl, $C_{2-4}$ alkynyl, $OR^{5G}$, $OC(O)R^{5H}$, $NR^{5I}R^{5J}$, $NHC(O)R^{5K}$, $NHC(S)R^{5L}$, $NHC(O)OR^{5M}$, $NHC(S)OR^{5N}$, $NHC(O)NHR^{5O}$, $NHC(S)NHR^{5P}$, $NHC(O)SR^{5Q}$, $NHC(S)SR^{5R}$, $NHS(O)_2R^{5S}$, $C(O)OR^{5T}$, and $C(O)NHR^{5U}$; each of $X^{5A}$ and $X^{5B}$ is, independently, selected from O and S; $X^{5C}$ is selected from $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl; and each of $R^{5G}$, $R^{5H}$, $R^{5I}$, $R^{5J}$, $R^{5K}$, $R^{5L}$, $R^{5M}$, $R^{5N}$, $R^{5O}$, $R^{5P}$, $R^{5Q}$, $R^{5R}$, $R^{5S}$, $R^{5T}$, and $R^{5U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. In one particular embodiment, $R^{5A}$ and $R^{5D}$ are H; each of $R^{5B}$, $R^{5C}$, $R^{5E}$, and $R^{5F}$ is, independently, selected from H, halide, nitro, $C_{1-4}$ alkyl, $C_{2-4}$ alkenyl, $C_{2-4}$ alkynyl, $OR^{5G}$, $OC(O)R^{5H}$, $NR^{5I}R^{5J}$, $NHC(O)R^{5K}$, $NHC(S)R^{5L}$, $NHC(O)OR^{5M}$, $NHC(S)OR^{5N}$, $NHC(O)NHR^{5O}$, $NHC(S)NHR^{5P}$, $NHC(O)SR^{5Q}$, $NHC(S)SR^{5R}$, $NHS(O)_2R^{5S}$, $C(O)OR^{5T}$, and $C(O)NHR^{5U}$; each of $X^{5A}$ and $X^{5B}$ is, independently, selected from O and S; $X^{5C}$ is selected from $C_{1-4}$ alkyl, $C_{2-4}$ alkenyl, and $C_{1-4}$ heteroalkyl; and each of $R^{5G}$, $R^{5H}$, $R^{5I}$, $R^{5J}$, $R^{5K}$, $R^{5L}$, $R^{5M}$, $R^{5N}$, $R^{5O}$, $R^{5P}$, $R^{5Q}$, $R^{5R}$, $R^{5S}$, $R^{5T}$, and $R^{5U}$ is, independently, selected from H, $C_{1-4}$ alkyl, $C_{2-4}$ alkenyl, $C_{2-4}$ alkynyl, and $C_{1-4}$ heteroalkyl.

The invention also features a pharmaceutical composition including a compound of formula (VI), or a salt thereof, and a pharmaceutically acceptable excipient.

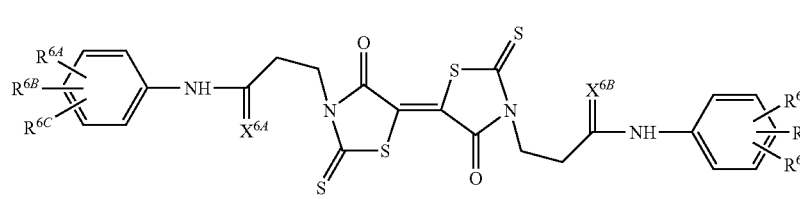

(VI)

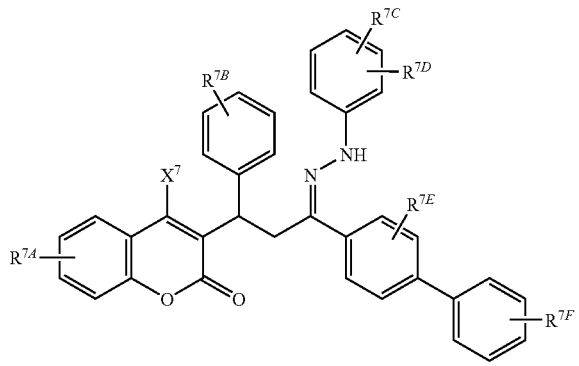

(VII)

In formula (VII) each of $R^{7A}$, $R^{7B}$, $R^{7C}$, $R^{7D}$, $R^{7E}$, and $R^{7F}$ is, independently, selected from H, halide, nitro, $C_{1-4}$ alkyl, $C_{2-4}$ alkenyl, $C_{2-4}$ alkynyl, $OR^{7G}$, $OC(O)R^{7H}$, $NR^{7I}R^{7J}$, $NHC(O)R^{7K}$, $NHC(S)R^{7L}$, $NHC(O)OR^{7M}$, $NHC(S)OR^{7N}$, $NHC(O)NHR^{7O}$, $NHC(S)NHR^{7P}$, $NHC(O)SR^{7Q}$, $NHC(S)SR^{7R}$, $NHS(O)_2R^{7S}$, $C(O)OR^{7T}$, and $C(O)NHR^{7U}$; $X^7$ is independently selected from $OR^{7G}$, $OC(O)R^{7H}$, $NR^{7I}R^{7J}$, $NHC(O)R^{7K}$, $NHC(S)R^{7L}$, $NHC(O)OR^{7M}$, $NHC(S)OR^{7N}$, $NHC(O)NHR^{7O}$, $NHC(S)NHR^{7P}$, $NHC(O)SR^{7Q}$, $NHC(S)SR^{7R}$, and $NHS(O)_2R^{7S}$; and each of $R^{7G}$, $R^{7H}$, $R^{7I}$, $R^{7J}$, $R^{7K}$, $R^{7L}$, $R^{7M}$, In formula (VI) each of $R^{6A}$, $R^{6B}$, $R^{6C}$, $R^{6D}$, $R^{6E}$, and $R^{6F}$ is, independently, selected from H, halide, nitro, $C_{1-4}$ alkyl, $C_{2-4}$ alkenyl, $C_{2-4}$ alkynyl, $OR^{6G}$, $OC(O)R^{6H}$, $NR^{6I}R^{6J}$, $NHC(O)R^{6K}$, $NHC(S)R^{6L}$, $NHC(O)OR^{6M}$, $NHC(S)OR^{6N}$, $NHC(O)NHR^{6O}$, $NHC(S)NHR^{6P}$, $NHC(O)SR^{6Q}$, $NHC(S)SR^{6R}$, $NHS(O)_2R^{6S}$, $C(O)OR^{6T}$, and $C(O)NHR^{6U}$; each of $X^{6A}$ and $X^{6B}$ is, independently, selected from O and S; and each of $R^{6G}$, $R^{6H}$, $R^{6I}$, $R^{6J}$, $R^{6K}$, $R^{6L}$, $R^{6M}$, $R^{6N}$, $R^{6O}$, $R^{6P}$, $R^{6Q}$, $R^{6R}$, $R^{6S}$, $R^{6T}$, and $R^{6U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. In one particular embodiment, $R^{6A}$ and $R^{6D}$ are H; each of $R^{6B}$, $R^{6C}$, $R^{6E}$, and $R^{6F}$ is, independently, selected from H, halide, nitro, $C_{1-4}$ alkyl, $C_{2-4}$ alkenyl, $C_{2-4}$ alkynyl, $OR^{6G}$, $OC(O)R^{6H}$, $NR^{6I}R^{6J}$, $NHC(O)R^{6K}$, $NHC(S)R^{6L}$, $NHC(O)OR^{6M}$, $NHC(S)OR^{6N}$, $NHC(O)NHR^{6O}$, $NHC(S)NHR^{6P}$, $NHC(O)SR^{6Q}$, $NHC(S)SR^{6R}$, $NHS(O)_2R^{6S}$, $C(O)OR^{6T}$, and $C(O)NHR^{6U}$; each of $X^{6A}$ and $X^{6B}$ is O; and each of $R^{6G}$, $R^{6H}$, $R^{6I}$, $R^{6J}$, $R^{6K}$, $R^{6L}$, $R^{6M}$, $R^{6N}$, $R^{6O}$, $R^{6P}$, $R^{6Q}$, $R^{6R}$, $R^{6S}$, $R^{6T}$, and $R^{6U}$ is, independently, selected from H, $C_{1-4}$ alkyl, $C_{2-4}$ alkenyl, $C_{2-4}$ alkynyl, and $C_{1-4}$ heteroalkyl.

The invention features a pharmaceutical composition including a compound of formula (VII), or a salt thereof, and a pharmaceutically acceptable excipient.

$R^{7N}$, $R^{7O}$, $R^{7P}$, $R^{7Q}$, $R^{7R}$, $R^{7S}$, $R^{7T}$, and $R^{7U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. In one particular embodiment, $R^{7A}$ is H; each of $R^{7B}$, $R^{7C}$, $R^{7D}$, $R^{7E}$, and $R^{7F}$ is, independently, selected from H, halide, nitro, $C_{1-4}$ alkyl, $C_{2-4}$ alkenyl, $C_{2-4}$ alkynyl, $OR^{7G}$, $OC(O)R^{7H}$, $NR^{7I}R^{7J}$, $NHC(O)R^{7K}$, $NHC(S)R^{7L}$, $NHC(O)OR^{7M}$, $NHC(S)OR^{7N}$, $NHC(O)NHR^{7O}$, $NHC(S)NHR^{7P}$, $NHC(O)SR^{7Q}$, $NHC(S)SR^{7R}$, $NHS(O)_2R^{7S}$, $C(O)OR^{7T}$, and $C(O)NHR^{7U}$; $X^7$ is independently $OR^{7G}$; and each of $R^{7G}$, $R^{7H}$, $R^{7I}$, $R^{7J}$, $R^{7K}$, $R^{7L}$, $R^{7M}$, $R^{7N}$, $R^{7O}$, $R^{7P}$, $R^{7Q}$, $R^{7R}$, $R^{7S}$, $R^{7T}$, and $R^{7U}$ is, independently, selected from H, $C_{1-4}$ alkyl, $C_{2-4}$ alkenyl, $C_{2-4}$ alkynyl, and $C_{1-4}$ heteroalkyl.

The invention further features a pharmaceutical composition including a compound of formula (VIII), or a salt thereof, and a pharmaceutically acceptable excipient.

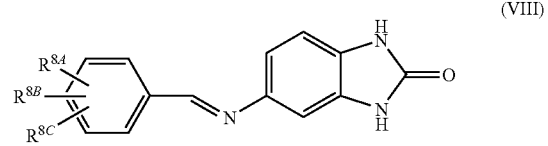

(VIII)

In formula (VIII) each of $R^{8A}$, $R^{8B}$, and $R^{8C}$ is, independently, selected from H, halide, nitro, $C_{1-4}$ alkyl, $C_{2-4}$ alkenyl, $C_{2-4}$ alkynyl, $OR^{8G}$, $OC(O)R^{8H}$, $NR^{8I}R^{8J}$, $NHC(O)R^{8K}$, $NHC(S)R^{8L}$, $NHC(O)OR^{8M}$, $NHC(S)OR^{8N}$, $NHC(O)NHR^{8O}$, $NHC(S)NHR^{8P}$, $NHC(O)SR^{8Q}$, $NHC(S)SR^{8R}$, $NHS(O)_2R^{8S}$, $C(O)OR^{8T}$, and $C(O)NHR^{8U}$; and each of $R^{8G}$, $R^{8H}$, $R^{8I}$, $R^{8J}$, $R^{8K}$, $R^{8L}$, $R^{8M}$, $R^{8N}$, $R^{8O}$, $R^{8P}$, $R^{8Q}$, $R^{8R}$, $R^{8S}$, $R^{8T}$, and $R^{8U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. In one particular embodiment, $R^{8A}$ is H; each of $R^{8B}$ and $R^{8C}$ is, independently, selected from H, halide, nitro, $C_{1-4}$ alkyl, $C_{2-4}$ alkenyl, $C_{2-4}$ alkynyl, $OR^{8G}$, $OC(O)R^{8H}$, $NR^{8I}R^{8J}$, $NHC(O)R^{8K}$, $NHC(S)R^{8L}$, $NHC(O)OR^{8M}$, $NHC(S)OR^{8N}$, $NHC(O)NHR^{8O}$, $NHC(S)NHR^{8P}$, $NHC(O)SR^{8Q}$, $NHC(S)SR^{8R}$, $NHS(O)_2R^{8S}$, $C(O)OR^{8T}$, and $C(O)NHR^{8U}$; and each of $R^{8G}$, $R^{8H}$, $R^{8I}$, $R^{8J}$, $R^{8K}$, $R^{8L}$, $R^{8M}$, $R^{8N}$, $R^{8O}$, $R^{8P}$, $R^{8Q}$, $R^{8R}$, $R^{8S}$, $R^{8T}$, and $R^{8U}$ is, independently, selected from H, $C_{1-4}$ alkyl, $C_{2-4}$ alkenyl, $C_{2-4}$ alkynyl, and $C_{1-4}$ heteroalkyl.

The invention also features a pharmaceutical composition including a compound of formula (IX), or a salt thereof, and a pharmaceutically acceptable excipient.

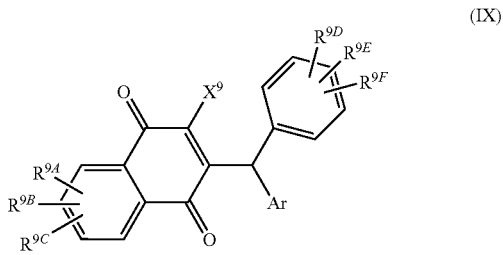

(IX)

In formula (IX) each of $R^{9A}$, $R^{9B}$, $R^{9C}$, $R^{9D}$, $R^{9E}$, and $R^{9F}$ is, independently, selected from H, halide, nitro, $C_{1-4}$ alkyl, $C_{2-4}$ alkenyl, $C_{2-4}$ alkynyl, $OR^{9G}$, $OC(O)R^{9H}$, $NR^{9I}R^{9J}$, $NHC(O)R^{9K}$, $NHC(S)R^{9L}$, $NHC(O)OR^{9M}$, $NHC(S)OR^{9N}$, $NHC(O)NHR^{9O}$, $NHC(S)NHR^{9P}$, $NHC(O)SR^{9Q}$, $NHC(S)SR^{9R}$, $NHS(O)_2R^{9S}$, $C(O)OR^{9T}$, and $C(O)NHR^{9U}$; $X^9$ is independently selected from $OR^{9G}$, $OC(O)R^{9H}$, $NR^{9I}R^{9J}$, $NHC(O)R^{9K}$, $NHC(S)R^{9L}$, $NHC(O)OR^{9M}$, $NHC(S)OR^{9N}$, $NHC(O)NHR^{9O}$, $NHC(S)NHR^{9P}$, $NHC(O)SR^{9Q}$, $NHC(S)SR^{9R}$, and $NHS(O)_2R^{9S}$; Ar is selected from $C_{2-6}$ heterocyclyl and $C_{6-12}$ aryl; and each of $R^{9G}$, $R^{9H}$, $R^{9I}$, $R^{9J}$, $R^{9K}$, $R^{9L}$, $R^{9M}$, $R^{9N}$, $R^{9O}$, $R^{9P}$, $R^{9Q}$, $R^{9R}$, $R^{9S}$, $R^{9T}$, and $R^{9U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. In one particular embodiment, $R^{9A}$, $R^{9B}$, and $R^{9C}$ are H; each of $R^{9D}$, $R^{9E}$, and $R^{9F}$ is, independently, selected from H, halide, nitro, $C_{1-4}$ alkyl, $C_{2-4}$ alkenyl, $C_{2-4}$ alkynyl, $OR^{9G}$, $OC(O)R^{9H}$, $NR^{9I}R^{9J}$, $NHC(O)R^{9K}$, $NHC(S)R^{9L}$, $NHC(O)OR^{9M}$, $NHC(S)OR^{9N}$, $NHC(O)NHR^{9O}$, $NHC(S)NHR^{9P}$, $NHC(O)SR^{9Q}$, $NHC(S)SR^{9R}$, $NHS(O)_2R^{9S}$, $C(O)OR^{9T}$, and $C(O)NHR^{9U}$; $X^9$ is independently $OR^{9G}$; Ar is selected from $C_{2-6}$ heterocyclyl and $C_{6-12}$ aryl; and each of $R^{9G}$, $R^{9H}$, $R^{9I}$, $R^{9J}$, $R^{9K}$, $R^{9L}$, $R^{9M}$, $R^{9N}$, $R^{9O}$, $R^{9P}$, $R^{9Q}$, $R^{9R}$, $R^{9S}$, $R^{9T}$, and $R^{9U}$ is, independently, selected from H, $C_{1-4}$ alkyl, $C_{2-4}$ alkenyl, $C_{2-4}$ alkynyl, and $C_{1-4}$ heteroalkyl.

The invention features a pharmaceutical composition including a compound of formula (X), or a salt thereof, and a pharmaceutically acceptable excipient.

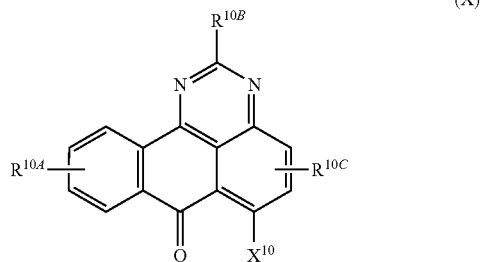

(X)

In formula (X) each of $R^{10A}$, $R^{10B}$, and $R^{10C}$ is, independently, selected from H, halide, nitro, $C_{1-4}$ alkyl, $C_{2-4}$ alkenyl, $C_{2-4}$ alkynyl, $OR^{10G}$, $OC(O)R^{10H}$, $NR^{10I}R^{10J}$, $NHC(O)R^{10K}$, $NHC(S)R^{10L}$, $NHC(O)OR^{10M}$, $NHC(S)OR^{10N}$, $NHC(O)NHR^{10O}$, $NHC(S)NHR^{10P}$, $NHC(O)SR^{10Q}$, $NHC(S)SR^{10R}$, $NHS(O)_2R^{10S}$, $C(O)OR^{10T}$, and $C(O)NHR^{10U}$; $X^{10}$ is independently selected from $OR^{10G}$, $OC(O)R^{10H}$, $NR^{10I}R^{10J}$, $NHC(O)R^{10K}$, $NHC(S)R^{10L}$, $NHC(O)OR^{10M}$, $NHC(S)OR^{10N}$, $NHC(O)NHR^{10O}$, $NHC(S)NHR^{10P}$, $NHC(O)SR^{10Q}$, $NHC(S)SR^{10R}$, and $NHS(O)_2R^{10S}$; and each of $R^{10G}$, $R^{10H}$, $R^{10I}$, $R^{10J}$, $R^{10K}$, $R^{10L}$, $R^{10M}$, $R^{10N}$, $R^{10O}$, $R^{10P}$, $R^{10Q}$, $R^{10R}$, $R^{10S}$, $R^{10T}$, and $R^{10U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. In one particular embodiment, $R^{10A}$ is H; each of $R^{10B}$ and $R^{10C}$ is, independently, selected from H, halide, nitro, $C_{1-4}$ alkyl, $C_{2-4}$ alkenyl, $C_{2-4}$ alkynyl, $OR^{10G}$, $OC(O)R^{10H}$, $NR^{10I}R^{10J}$, $NHC(O)R^{10K}$, $NHC(S)R^{10L}$, $NHC(O)OR^{10M}$, $NHC(S)OR^{10N}$, $NHC(O)NHR^{10O}$, $NHC(S)NHR^{10P}$, $NHC(O)SR^{10Q}$, $NHC(S)SR^{10R}$, $NHS(O)_2R^{10S}$, $C(O)OR^{10T}$, and $C(O)NHR^{10U}$; $X^{10}$ is independently selected from $NR^{10I}R^{10J}$, $NHC(O)R^{10K}$, $NHC(S)R^{10L}$, $NHC(O)OR^{10M}$, $NHC(S)OR^{10N}$, $NHC(O)NHR^{10O}$, $NHC(S)NHR^{10P}$, $NHC(O)SR^{10Q}$, $NHC(S)SR^{10R}$, and $NHS(O)_2R^{10S}$; and each of $R^{10G}$, $R^{10H}$, $R^{10I}$, $R^{10J}$, $R^{10K}$, $R^{10L}$, $R^{10M}$, $R^{10N}$, $R^{10O}$, $R^{10P}$, $R^{10Q}$, $R^{10R}$, $R^{10S}$, $R^{10T}$, and $R^{10U}$ is, independently, selected from H, $C_{1-4}$ alkyl, $C_{2-4}$ alkenyl, $C_{2-4}$ alkynyl, and $C_{1-4}$ heteroalkyl.

The invention further features a pharmaceutical composition including a compound of formula (XI), or a salt thereof, and a pharmaceutically acceptable excipient.

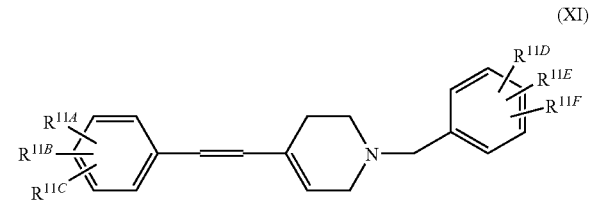

(XI)

In formula (XI) each of $R^{11A}$, $R^{11B}$, $R^{11C}$, $R^{11D}$, $R^{11E}$, and $R^{11F}$ is, independently, selected from H, halide, nitro, $C_{1-4}$ alkyl, $C_{2-4}$ alkenyl, $C_{2-4}$ alkynyl, $OR^{11G}$, $OC(O)R^{11H}$, $NR^{11I}R^{11J}$, $NHC(O)R^{11K}$, $NHC(S)R^{11L}$, $NHC(O)OR^{11M}$, $NHC(S)OR^{11N}$, $NHC(O)NHR^{11O}$, $NHC(S)NHR^{11P}$, $NHC(O)SR^{11Q}$, $NHC(S)SR^{11R}$, $NHS(O)_2R^{11S}$, $C(O)OR^{11T}$, and $C(O)NHR^{11U}$; and each of $R^{11G}$, $R^{11H}$, $R^{11I}$, $R^{11J}$, $R^{11K}$, $R^{11L}$, $R^{11M}$, $R^{11N}$, $R^{11O}$, $R^{11P}$, $R^{11Q}$, $R^{11R}$, $R^{11S}$, $R^{11T}$, and $R^{11U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. In one particular embodiment, $R^{11A}$ and $R^{11D}$ are H; each of $R^{11B}$, $R^{11C}$, $R^{11E}$, and $R^{11F}$ is, independently, selected from H, halide, nitro, $C_{1-4}$ alkyl, $C_{2-4}$ alkenyl, $C_{2-4}$ alkynyl, $OR^{11G}$, $OC(O)R^{11H}$, $NR^{11I}R^{11J}$, $NHC(O)R^{11K}$, $NHC(S)R^{11L}$, $NHC(O)OR^{11M}$, $NHC(S)OR^{11N}$, $NHC(O)NHR^{11O}$, $NHC(S)NHR^{11P}$, $NHC(O)SR^{11Q}$, $NHC(S)SR^{11R}$, $NHS(O)_2R^{11S}$, $C(O)OR^{11T}$, and $C(O)NHR^{11U}$; and each of $R^{11G}$, $R^{11H}$, $R^{11I}$, $R^{11J}$, $R^{11K}$, $R^{11L}$, $R^{11M}$, $R^{11N}$, $R^{11O}$, $R^{11P}$, $R^{11Q}$, $R^{11R}$, $R^{11S}$, $R^{11T}$, and $R^{11U}$ is, independently, selected from H, $C_{1-4}$ alkyl, $C_{2-4}$ alkenyl, $C_{2-4}$ alkynyl, and $C_{1-4}$ heteroalkyl.

The invention also features a pharmaceutical composition including a compound of formula (XII), or a salt thereof, and a pharmaceutically acceptable excipient.

(XII)

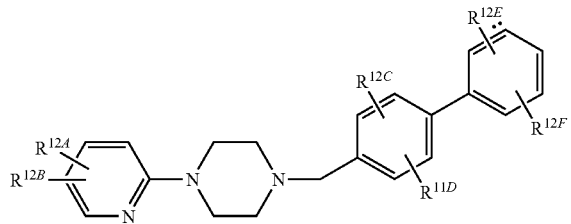

In formula (XII) each of $R^{12A}$, $R^{12B}$, $R^{12C}$, $R^{12D}$, $R^{12E}$, and $R^{12F}$ is, independently, selected from H, halide, nitro, $C_{1-4}$ alkyl, $C_{2-4}$ alkenyl, $C_{2-4}$ alkynyl, $OR^{12G}$, $OC(O)R^{12H}$, $NR^{12I}R^{12J}$, $NHC(O)R^{12K}$, $NHC(S)R^{12L}$, $NHC(O)OR^{12M}$, $NHC(S)OR^{12N}$, $NHC(O)NHR^{12O}$, $NHC(S)NHR^{12P}$, $NHC(O)SR^{12Q}$, $NHC(S)SR^{12R}$, $NHS(O)_2R^{12S}$, $C(O)OR^{12T}$, and $C(O)NHR^{12U}$; and each of $R^{12G}$, $R^{12H}$, $R^{12I}$, $R^{12J}$, $R^{12K}$, $R^{12L}$, $R^{12M}$, $R^{12N}$, $R^{12O}$, $R^{12P}$, $R^{12Q}$, $R^{12R}$, $R^{12S}$, $R^{12T}$, and $R^{12U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. In one particular embodiment, $R^{12A}$, $R^{12C}$, and $R^{12E}$ are H; each of $R^{12B}$, $R^{12D}$, and $R^{12F}$ is, independently, selected from H, halide, nitro, $C_{1-4}$ alkyl, $C_{2-4}$ alkenyl, $C_{2-4}$ alkynyl, $OR^{12G}$, $OC(O)R^{12H}$, $NR^{12I}R^{12J}$, $NHC(O)R^{12K}$, $NHC(S)R^{12L}$, $NHC(O)OR^{12M}$, $NHC(S)OR^{12N}$, $NHC(O)NHR^{12O}$, $NHC(S)NHR^{12P}$, $NHC(O)SR^{12Q}$, $NHC(S)SR^{12R}$, $NHS(O)_2R^{12S}$, $C(O)OR^{12T}$, and $C(O)NHR^{12U}$; and each of $R^{12G}$, $R^{12H}$, $R^{12I}$, $R^{12J}$, $R^{12K}$, $R^{12L}$, $R^{12M}$, $R^{12N}$, $R^{12O}$, $R^{12P}$, $R^{12Q}$, $R^{12R}$, $R^{12S}$, $R^{12T}$, and $R^{12U}$ is, independently, selected from H, $C_{1-4}$ alkyl, $C_{2-4}$ alkenyl, $C_{2-4}$ alkynyl, and $C_{1-4}$ heteroalkyl.

The invention features a pharmaceutical composition including a compound of formula (XIII), or a salt thereof, and a pharmaceutically acceptable excipient.

(XIII)

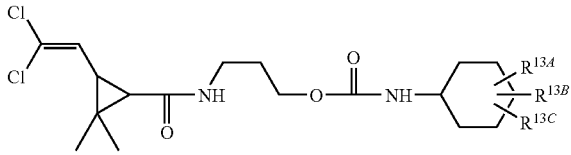

In formula (XIII) each of $R^{13A}$, $R^{13B}$, and $R^{13C}$ is, independently, selected from H, halide, nitro, $C_{1-4}$ alkyl, $C_{2-4}$ alkenyl, $C_{2-4}$ alkynyl, $OR^{13G}$, $OC(O)R^{13H}$, $NR^{13I}R^{13J}$, $NHC(O)R^{13K}$, $NHC(S)R^{13L}$, $NHC(O)OR^{13M}$, $NHC(S)OR^{13N}$, $NHC(O)NHR^{13O}$, $NHC(S)NHR^{13P}$, $NHC(O)SR^{13Q}$, $NHC(S)SR^{13R}$, $NHS(O)_2R^{13S}$, $C(O)OR^{13T}$, and $C(O)NHR^{13U}$; and each of $R^{13G}$, $R^{13H}$, $R^{13I}$, $R^{13J}$, $R^{13K}$, $R^{13L}$, $R^{13M}$, $R^{13N}$, $R^{13O}$, $R^{13P}$, $R^{13Q}$, $R^{13R}$, $R^{13S}$, $R^{13T}$, and $R^{13U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. In one particular embodiment, $R^{13A}$ is H; each of $R^{13B}$ and $R^{13C}$ is, independently, selected from H, halide, nitro, $C_{1-4}$ alkyl, $C_{2-4}$ alkenyl, $C_{2-4}$ alkynyl, $OR^{13G}$, $OC(O)R^{13H}$, $NR^{13I}R^{13J}$, $NHC(O)R^{13K}$, $NHC(S)R^{13L}$, $NHC(O)OR^{13M}$, $NHC(S)OR^{13N}$, $NHC(O)NHR^{13O}$, $NHC(S)NHR^{13P}$, $NHC(O)SR^{13Q}$, $NHC(S)SR^{13R}$, $NHS(O)_2R^{13S}$, $C(O)OR^{13T}$, and $C(O)NHR^{13U}$; and each of $R^{13G}$, $R^{13H}$, $R^{13I}$, $R^{13J}$, $R^{13K}$, $R^{13L}$, $R^{13M}$, $R^{13N}$, $R^{13O}$, $R^{13P}$, $R^{13Q}$, $R^{13R}$, $R^{13S}$, $R^{13T}$, and $R^{13U}$ is, independently, selected from H, $C_{1-4}$ alkyl, $C_{2-4}$ alkenyl, $C_{2-4}$ alkynyl, and $C_{1-4}$ heteroalkyl.

The invention further features a pharmaceutical composition including a compound of formula (XIV), or a salt thereof, and a pharmaceutically acceptable excipient.

(XIV)

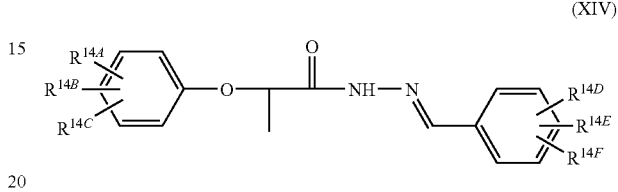

In formula (XIV) each of $R^{14A}$, $R^{14B}$, $R^{14C}$, $R^{14D}$, $R^{14E}$, and $R^{14F}$ is, independently, selected from H, halide, nitro, $C_{1-4}$ alkyl, $C_{2-4}$ alkenyl, $C_{2-4}$ alkynyl, $OR^{14G}$, $OC(O)R^{14H}$, $NR^{14I}R^{14J}$, $NHC(O)R^{14K}$, $NHC(S)R^{14L}$, $NHC(O)OR^{14M}$, $NHC(S)OR^{14N}$, $NHC(O)NHR^{14O}$, $NHC(S)NHR^{14P}$, $NHC(O)SR^{14Q}$, $NHC(S)SR^{14R}$, $NHS(O)_2R^{14S}$, $C(O)OR^{14T}$, and $C(O)NHR^{14U}$; and each of $R^{14G}$, $R^{14H}$, $R^{14I}$, $R^{14J}$, $R^{14K}$, $R^{14L}$, $R^{14M}$, $R^{14N}$, $R^{14O}$, $R^{14P}$, $R^{14Q}$, $R^{14R}$, $R^{14S}$, $R^{14T}$, and $R^{14U}$ is, independently, selected from H, $C_{1-4}$ alkyl, $C_{2-4}$ alkenyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. In one particular embodiment, $R^{14A}$ and $R^{14D}$ are H; each of $R^{14B}$, $R^{14C}$, $R^{14E}$, and $R^{14F}$ is, independently, selected from H, halide, nitro, $C_{1-4}$ alkyl, $C_{2-4}$ alkenyl, $C_{2-4}$ alkynyl, $OR^{14G}$, $OC(O)R^{14H}$, $NR^{14I}R^{14J}$, $NHC(O)R^{14K}$, $NHC(S)R^{14L}$, $NHC(O)OR^{14M}$, $NHC(S)OR^{14N}$, $NHC(O)NHR^{14O}$, $NHC(S)NHR^{14P}$, $NHC(O)SR^{14Q}$, $NHC(S)SR^{14R}$, $NHS(O)_2R^{14S}$, $C(O)OR^{14T}$, and $C(O)NHR^{14U}$; and each of $R^{14G}$, $R^{14H}$, $R^{14I}$, $R^{14J}$, $R^{14K}$, $R^{14L}$, $R^{14M}$, $R^{14N}$, $R^{14O}$, $R^{14P}$, $R^{14Q}$, $R^{14R}$, $R^{14S}$, $R^{14T}$, and $R^{14U}$ is, independently, selected from H, $C_{1-4}$ alkyl, $C_{2-4}$ alkenyl, $C_{2-4}$ alkynyl, and $C_{1-4}$ heteroalkyl.

The invention also features a pharmaceutical composition including a compound of formula (XV), or a salt thereof, and a pharmaceutically acceptable excipient.

(XV)

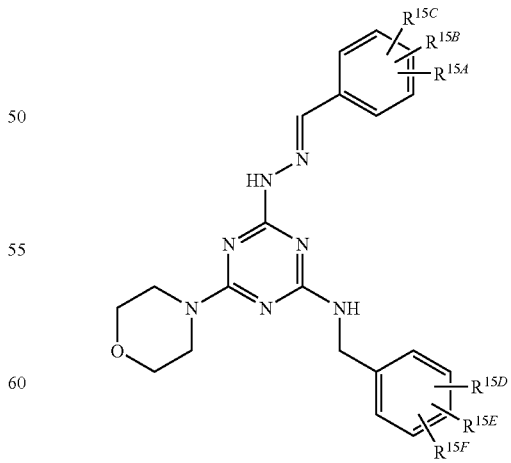

In formula (XV) each of $R^{15A}$, $R^{15B}$, $R^{15C}$, $R^{15D}$, $R^{15E}$, and $R^{15F}$ is, independently, selected from H, halide, nitro, $C_{1-4}$ alkyl, $C_{2-4}$ alkenyl, $C_{2-4}$ alkynyl, $OR^{15G}$, $OC(O)R^{15H}$, NR$^{15I}$R$^{15J}$, NHC(O)R$^{15K}$, NHC(S)R$^{15L}$, NHC(O)OR$^{15M}$, NHC(S)OR$^{15N}$, NHC(O)NHR$^{15O}$, NHC(S)NHR$^{15P}$, NHC(O)SR$^{15Q}$, NHC(S)SR$^{15R}$, NHS(O)$_2$R$^{15S}$, C(O)OR$^{15T}$, and C(O)NHR$^{15U}$; and each of R$^{15G}$, R$^{15H}$, R$^{15I}$, R$^{15J}$, R$^{15K}$, R$^{15L}$, R$^{15M}$, R$^{15N}$, R$^{15O}$, R$^{15P}$, R$^{15Q}$, R$^{15R}$, R$^{15S}$, R$^{15T}$, and R$^{15U}$ is, independently, selected from H, C$_{1-4}$ alkyl, C$_{2-4}$ alkenyl, C$_{2-4}$ alkynyl, C$_{2-6}$ heterocyclyl, C$_{6-12}$ aryl, C$_{7-14}$ alkaryl, C$_{3-10}$ alkheterocyclyl, and C$_{1-4}$ heteroalkyl. In one particular embodiment, R$^{15A}$ and R$^{15D}$ are H; each of R$^{15B}$, R$^{15C}$, R$^{15E}$, and R$^{15F}$ is, independently, selected from H, halide, nitro, C$_{1-4}$ alkyl, C$_{2-4}$ alkenyl, C$_{2-4}$ alkynyl, OR$^{15G}$, OC(O)R$^{15H}$, NR$^{15I}$R$^{15J}$, NHC(O)R$^{15K}$, NHC(S)R$^{15L}$, NHC(O)OR$^{15M}$, NHC(S)OR$^{15N}$, NHC(O)NHR$^{15O}$, NHC(S)NHR$^{15P}$, NHC(O)SR$^{15Q}$, NHC(S)SR$^{15R}$, NHS(O)$_2$R$^{15S}$, C(O)OR$^{15T}$, and C(O)NHR$^{15U}$; and each of R$^{15G}$, R$^{15H}$, R$^{15I}$, R$^{15J}$, R$^{15K}$, R$^{15L}$, R$^{15M}$, R$^{15N}$, R$^{15O}$, R$^{15P}$, R$^{15Q}$, R$^{15R}$, R$^{15S}$, R$^{15T}$, and R$^{15U}$ is, independently, selected from H, C$_{1-4}$ alkyl, C$_{2-4}$ alkenyl, C$_{2-4}$ alkynyl, and C$_{1-4}$ heteroalkyl.

The invention further features a method of treating a microbial or viral infection in a subject (e.g., a host animal or plant) that includes the step of administering to the subject a pharmaceutical composition of the invention in an amount effective to treat the infection. Thus, the present invention can be used to treat a range of disorders associated with infection including; but not limited to, sepsis syndrome, cachexia, circulatory collapse and shock resulting from acute or chronic bacterial infection, acute and chronic parasitic and/or infectious diseases from bacterial, viral or fungal sources, such as a HIV, AIDS (including symptoms of cachexia, autoimmune disorders, AIDS dementia complex and infections) can be treated, as well as Wegners Granulomatosis. In the above method, the infection can be a microbial infection (e.g., a protozoan, bacterial, mycobacterium, or fungal infection) or a viral infection.

In plants, compounds of the invention can be used to prevent or treat a broad range of fungal infections including powdery mildews such as *Erysiphe* spp. and *Sphaerotheca* spp., downy mildews such as *Bremia* spp. and *Peronospora* spp., black spot including *Diplocarpon* spp., blights such as *Alternaria* spp. and *Diplodia* spp., cankers such as *Penicillium* spp. and *Coniothyrium* spp., leaf curl such as *Taphrina* spp., leaf spot such as *Botrytis* spp. and *Rhytisma* spp., rots such as *Aspergillus* spp., *Fusarium* spp., *Rhizoctonia* spp., *Pythium* spp., *Phytophthora* spp. *Sclerotinia* spp., rusts such as soybean rust (e.g., *Phakopsora pachyrhizi*) and *Puccinia* spp., *Cronartium* spp., scabs such as *Venturia* spp., and smuts such as *Urocystis* spp. The compounds of the invention may also be used to prevent or treat various bacterial infections in plants including infections by *Erwinia* spp., *Agrobacterium* spp., *Pseudomonas* spp., and *Xanthomonas* spp.

In one particular embodiment, the infection to be treated is a bacterial infection selected from bacterial pathogens that cause community-acquired pneumonia, upper and lower respiratory tract infections, skin and soft tissue infections, hospital-acquired lung infections, bone and joint infections, respiratory tract infections, acute bacterial otitis media, bacterial pneumonia, urinary tract infections, complicated infections, noncomplicated infections, pyelonephritis, intra-abdominal infections, deep-seated abscesses, bacterial sepsis, central nervous system infections, bacteremia, wound infections, peritonitis, meningitis, infections after burn, urogenital tract infections, gastro-intestinal tract infections, pelvic inflammatory disease, endocarditis, and other intravascular infections. The methods of treating bacterial infections described herein are useful in treating an infection by a Gram-positive bacterium. Desirably, the methods are used to treat infection by a Gram-positive coccus, or by a drug-resistant Gram-positive coccus. Desirably, the Gram-positive coccus is selected from *S. aureus, S. epidermidis, S. pneumoniae, S. pyogenes, M. catarrhalis, H. influenzae,* and *Enterococcus* spp. Alternatively, the bacterial infection to be treated is by *Chlamydia pneumoniae* or *Chlamydia trachomatis*. The methods of treating bacterial infections described herein can also be useful in treating an infection is by a Gram-negative bacterium, including, without limitation, *Pseudonomas aeruginosa, Klebsiella pneumoniae, Escherichia coli, Haemophilus influenzae, Citrobacter freundii* and *Enterobacter* spp. Further, the methods of treating bacterial infections described herein can also be useful for treating agriculturally important bacterial infections such as, for example, *Erwinia* spp., *Agrobacterium tumefaciens, Agrobacterium rhizogenes, Pseudomonas syringae,* or *Xanthomonas* spp. infections in plants.

The methods of the invention can be used to reduce or eliminate the incidence of postoperative infections in subjects undergoing surgical procedures or implantation of prosthetic devices.

The invention further features a method of treating an infection by multi-drug resistant bacteria in a subject (e.g., a host animal or plant). The method includes administering to the subject a pharmaceutical composition of the invention, wherein the compound is administered in an amount effective to treat the multi-drug resistant infection. Resistant strains of bacteria include penicillin-resistant, methicillin-resistant, quinolone-resistant, macrolide-resistant, and/or vancomycin-resistant bacterial strains. The multi-drug resistant bacterial infections to be treated using the methods of the invention include, for example, infections by penicillin-, methicillin-, macrolide-, vancomycin-, and/or quinolone-resistant *Streptococcus pneumoniae*; penicillin-, methicillin-, macrolide-, vancomycin-, and/or quinolone-resistant *Staphylococcus aureus*; penicillin-, methicillin-, macrolide-, vancomycin-, and/or quinolone-resistant *Streptococcus pyogenes*; and penicillin-, methicillin-, macrolide-, vancomycin-, and/or quinolone-resistant enterococci.

In the above method, the infection can be caused by a fungus selected from, without limitation, *Absidia corymbifera, Acremonium falciforme, A. kiliense, A. recifei, Ajellomyces dermatitidis, A. capsulata, Aspergillus* spp., (e.g., *A. flavus, A. fumigatus, A. nidulans, A. niger, A. terreus*), *Candida* spp. (e.g., *C. albicans, C. glabrata, C. guillermondii, C. krusei, C. parapsilosis, C. kefyr, C. tropicalis*), *Crytococcus* spp. (e.g., *C. neoformans, C. gattii, C. grubii*), *Cunninghamella elegans, Emmonsia parva, Epidermophyton floccosum, Exophialia dermitidis, E. werneckii, E. jeanselmei, E. spinifera, E. richardsiae, Filobasidiella neoformans, Fonsecaea compacta, F. pedrosoi, Histoplasma capsulatum, Leptoshaeria senegarlensis, Madurella mycetomatis, M. grisea, Malassezia furfur, Microsporum* spp, *Neotestudina rosatii, Paracoccidioides brasiliensis, Penicillium marneffei, Phialophora verrucosa, Piedraia hortae, Pneumocystis* spp., *Pseudallescheria boydii, Pyrenochaeta romeroi, Rhizomucor pusillus, Sporothrix schenckii, Trichophyton* spp, *Trichosporon beigelii, Wangiella dermatitidis* and *Xylohypha bantiana*. In addition, in plants, the infection can be caused by a fungus selected from, without limitation, *Botrytis* spp., *Fusarium* spp., *Alternaria* spp., *Erysiphe* spp., *Rhytisma* spp., *Thielaviopsis* spp., *Verticillium* spp., *Aspergillus* spp., *Magnaporthe grisea, Rhizoctonia* spp., *Phakospora pachyrhizi, Puccinia* spp., *Diplocarpon* spp., *Sphaerotheca* spp., *Phytophthora* spp., *Venturia* spp., *Taphrina* spp., *Phythium* spp., *Penicillium* spp., *Urocystis* spp., and *Coniothyrium* spp.

Fungal infections that can be treated using the methods of the invention include tinea capitis, tinea corporis, tinea pedis, tinea barbae, tinea cruris, tinea versicolor, onychomycosis, perionychomycosis, pityriasis versicolor, tinea unguium, oral thrush, vaginal candidosis, respiratory tract candidosis, biliary candidosis, esophageal candidosis, urinary tract candidosis, systemic candidosis, mucocutaneous candidosis, mycetoma, cryptococcosis, aspergillosis, mucormycosis, chromoblastomycosis, paracoccidioidomycosis, North American blastomycosis, histoplasmosis, coccidioidomycosis, or sporotrichosis.

In the above method, the infection can be a viral infection, such as, vesicular stomatitis virus, influenza, HIV, or mononucleosis. In plants, the viral infection may be a nepovirus, poytvirus, tymovirus, ilarvirus, potexvirus, caulimovirus, tobravirus, closterovirus, carlavirus, cucumovirus, tobamovirus, comovirus, carmovirus, necrovirus, nucleorhabdovirus, tospovirus, luteovirus, fijivirus, or tenuivirus infection. In particular, the viral infection may be a tobacco mosaic virus infection or a leafroll virus infection.

In a related aspect, the invention features a kit including a pharmaceutical composition of the invention and instructions for administering the composition to a subject (e.g., a host organism or a plant) for the treatment of a microbial or viral infection. The specific infection to be treated and recited in the kit instructions can be any described herein.

Pharmaceutical formulations containing a compound of the invention can include isomers such as diastereomers and enantiomers, mixtures of isomers, including racemic mixtures, salts, solvates, and polymorphs thereof.

In another aspect, the invention features a method for identifying a compound that is capable of inhibiting a pathogen in an invertebrate animal host organism. This method involves (a) exposing the invertebrate host organism to a pathogen; (b) incubating the exposed invertebrate host organism in liquid medium in the presence of at least one candidate compound; and (c) identifying a compound that inhibits the pathogen in the invertebrate host organism. In desirable embodiments, step (b) is performed before step (a). In other desirable embodiments, prior to step (a), the invertebrate animal host organism is exposed to the candidate compound. These desirable embodiments can be used to identify a prophylactic compound.

In other desirable embodiments, identifying of step (c) involves using an automated microscope and identifying desirably involves determining whether the host organism is alive or dead. In further desirable embodiments, the exposed invertebrate host organism is transferred to the liquid medium by a robot. In yet other desirable embodiments the identifying step involves using a fluorescent marker (e.g., green fluorescent protein, Nile Red, or MitoTracker). Desirably, the fluorescent marker selectively stains dead or dying cells and, desirably, is Sytox® green or Sytox® orange.

In additional desirable embodiments of this aspect of the invention, inhibiting kills the pathogen. Desirably, the compound is a low molecular weight chemical compound.

In further desirable embodiment, the invertebrate host organism is a nematode (e.g., a *Caenorhabditis elegans* nematode). The *Caenorhabditis elegans* nematode desirably contains a mutation in the mitogen-activated protein kinase (MAPK) pathway. A desirable example of such a mutation in the MAPK pathway is sek-1. In other desirable embodiments, the *Caenorhabditis elegans* nematode is a temperature sensitive sterile mutant *Caenorhabditis elegans* nematode. Desirably, the temperature sensitive sterile mutant *Caenorhabditis elegans* nematode is a glp-4 mutant.

In additional desirable embodiments, the invertebrate host organism is a *Drosophila* larva (e.g., a *Drosophila melanogaster* larva). In yet other desirable embodiments, the invertebrate host organism is a *Plutella xylostella* larva or a *Galleria mellonella* larva.

In another desirable embodiment of this aspect of the invention, the pathogen is a bacterial pathogen (e.g., *Enterococcus, Pseudomonas, Salmonella*, or *Staphylococcus*). Desirably, the *Enterococcus* is *Enterococcus faecalis*, the *Pseudomonas* is *Pseudomonas aeruginosa*, the *Salmonella* is *Salmonella typhimurium*, or the *Staphylococcus* is *Staphylococcus aureus, Staphylococcus epidermidis*, or *Staphylococcus saprophyticus*.

In yet other desirable embodiments of this aspect of the invention, the pathogen is a fungal pathogen (e.g., *Candida, Cryptococcus, Fusarium, Rhodotorula, Aspergillus*, or *Saccharomyces*). Desirably, the *Candida* is *Candida albicans, Candida glabrata*, or *Candida parapsilosis*, the *Cryptococcus* is *Cryptococcus neoformans, Crytococcus gattii*, or *Crytococcus grubii*, the *Rhodotorula* is *Rhodotorula mucilaginosa*, the *Saccharomyces* is *Saccharomyces cerevisiae*, or the *Aspergillus* is *Aspergillus flavus, Aspergillus fumigatus, Aspergillus nidulans, Aspergillus niger*, or *Aspergillus terreus*.

In further desirable embodiments of this aspect of the invention, the pathogen is a viral pathogen (e.g., vesicular stomatitis virus (VSV)). In another desirable embodiment of this aspect of the invention, the pathogen is a protozoan. In yet another desirable embodiment of this aspect of the invention, the pathogen is a *Mycobacterium* (e.g., *Mycobacterium tuberculosis*).

In another aspect, the invention features a container including (i) an invertebrate animal host organism infected with a pathogen, (ii) liquid media, and (iii) a candidate compound. Desirably, the container is a 24-well plate, a 48-well plate, a 96-well plate, a 384-well plate, a 1536-well plate, or a 3456-well plate. In desirable embodiments, each well of the plate contains a different candidate compound.

Desirably, the liquid medium contains a fluorescent marker, such as a fluorescent marker that selectively stains dead or dying cells. In desirable embodiments, the fluorescent marker is Sytox® green or Sytox® orange.

In other desirable embodiments of this aspect of the invention, the compound is a low molecular weight chemical compound.

In additional desirable embodiments of this aspect of the invention, the invertebrate host organism is a nematode (e.g., a *Caenorhabditis elegans* nematode). Desirably, the *Caenorhabditis elegans* nematode contains a mutation in the mitogen-activated protein kinase (MAPK) pathway. In a desirable embodiment, the mutation in the MAPK pathway is sek-1. In another desirable embodiment of this aspect of the invention, the *Caenorhabditis elegans* nematode is a temperature sensitive sterile mutant *Caenorhabditis elegans* nematode. The temperature sensitive sterile mutant *Caenorhabditis elegans* nematode desirably is a glp-4 mutant.

In another desirable embodiment of this aspect of the invention, the invertebrate host organism is a *Drosophila* larva (e.g., a *Drosophila melanogaster* larva). In other desirable embodiments, the invertebrate host organism is a *Plutella xylostella* larva or a *Galleria mellonella* larva.

In further desirable embodiments of this aspect of the invention, the pathogen is a bacterial pathogen (e.g., *Enterococcus, Pseudomonas, Salmonella*, or *Staphylococcus*). Desirably, the *Enterococcus* is *Enterococcus faecalis*, the *Pseudomonas* is *Pseudomonas aeruginosa*, the *Salmonella* is *Salmonella typhimurium*, or the *Staphylococcus* is *Staphylococcus aureus, Staphylococcus epidermidis*, or *Staphylococcus saprophyticus*.

In other desirable embodiments of this aspect of the invention, the pathogen is a fungal pathogen (e.g., *Candida, Cryptococcus, Fusarium, Rhodotorula, Aspergillus,* or *Saccharomyces*). Desirably, the *Candida* is *Candida albicans, Candida glabrata,* or *Candida parapsilosis,* the *Cryptococcus* is *Cryptococcus neoformans, Crytococcus gattii,* or *Crytococcus grubii,* the *Rhodotorula* is *Rhodotorula mucilaginosa,* the *Saccharomyces* is *Saccharomyces cerevisiae,* or the *Aspergillus* is *Aspergillus flavus, Aspergillus fumigatus, Aspergillus nidulans, Aspergillus niger,* or *Aspergillus terreus.*

In yet another desirable embodiment of this aspect of the invention, the pathogen is a viral pathogen (e.g., vesicular stomatitis virus (VSV)). In a further desirable embodiment, the pathogen is a protozoan. In yet another desirable embodiment of this aspect of the invention, the pathogen is a *Mycobacterium* (e.g., *Mycobacterium tuberculosis*).

In another aspect, the invention features a method for identifying a compound that is capable of inhibiting a pathogen in a plant host organism. This method involves (a) exposing the plant host organism to a pathogen; (b) incubating the exposed plant host organism in liquid medium in the presence of at least one candidate compound; and (c) identifying a compound that inhibits the pathogen in the plant host organism. In desirable embodiments, step (b) is performed before step (a). In other desirable embodiments, the plant is exposed to the candidate compound prior to step (a). In additional desirable embodiments of this aspect of the invention, the identifying step (c) involves using an automated microscope. Desirably, the identifying step (c) involves determining whether the host organism is alive or dead.

In a desirable embodiment, the plant host organism is an *Arabidopsis thaliana* seedling.

In yet another desirable embodiment, the exposed plant host organism is transferred to the liquid medium by a robot. In yet other desirable embodiments of this aspect of the invention, the identifying step (c) involves using a fluorescent or luminescent marker. Desirably, the fluorescent marker is green fluorescent protein, Nile Red, or MitoTracker and the luminescent marker is luciferase.

In other desirable embodiments of this aspect of the invention, the fluorescent marker selectively stains dead or dying cells. Such a fluorescent marker desirably is Sytox® green or Sytox® orange. In additional desirable embodiments of this aspect of the invention, the inhibiting kills the pathogen. In further desirable embodiments, the compound is a low molecular weight chemical compound.

In yet another desirable embodiment of this aspect of the invention, the pathogen is a bacterial pathogen (e.g., *Pseudomonas, Xanthomonas, Erwinia,* or *Agrobacterium*). Desirably, the *Pseudomonas* is *Pseudomonas aeruginosa* or *Pseudomonas syringae.*

In another desirable embodiment of this aspect of the invention, the pathogen is a fungal pathogen. Desirably, the fungal pathogen is *Candida, Cryptococcus, Fusarium, Rhodotorula, Aspergillus, Saccharomyces, Botrytis, Erysiphe, Alternaria, Rhytisma, Thielaviopsis, Verticillium, Aspergillus, Magnaporthe grisea, Rhizoctonia, Phakospora pachyrhizi, Puccinia, Diplocarpon, Sphaerotheca, Phytophthora, Venturia, Taphrina, Phythium, Penicillium, Urocystis,* or *Coniothyrium.* In particularly desirable embodiments, the *Candida* is *Candida albicans, Candida glabrata,* or *Candida parapsilosis,* the *Cryptococcus* is *Cryptococcus neoformans, Crytococcus gattii,* or *Crytococcus grubii,* the *Rhodotorula* is *Rhodotorula mucilaginosa,* the *Saccharomyces* is *Saccharomyces cerevisiae,* or the *Aspergillus* is *Aspergillus flavus, Aspergillus fumigatus, Aspergillus nidulans, Aspergillus niger,* or *Aspergillus terreus,* the *Botrytis* is *Botrytis cinera,* or the *Fusarium* is *Fusarium oxysporum.*

In further desirable embodiments of this aspect of the invention, the pathogen is a viral pathogen. Desirably, the viral pathogen is a nepovirus, poytvirus, tymovirus, ilarvirus, potexvirus, caulimovirus, tobravirus, closterovirus, carlavirus, cucumovirus, tobamovirus, comovirus, carmovirus, necrovirus, nucleorhabdovirus, tospovirus, luteovirus, fijivirus, or tenuivirus. In particularly desirable embodiments, the viral pathogen is tobacco mosaic virus, tobacco necrosis virus, potato leaf roll virus, potato virus X, potato virus Y, tomato spotted wilt virus, or tomato ring spot virus. In yet other desirable embodiments, the pathogen is a protozoan or a *Mycobacterium.*

In yet another aspect, the invention features a container including (i) a plant host organism infected with a pathogen, (ii) liquid media, and (iii) a candidate compound. Desirably, the container is a 24-well plate, a 48-well plate, a 96-well plate, a 384-well plate, a 1536-well plate, or a 3456-well plate. Desirably, each well of the plate contains a different candidate compound. The plant host organism desirably is an *Arabidopsis thaliana* seedling.

In desirable embodiments of this aspect of the invention, the liquid medium contains a fluorescent or luminescent marker. Desirably, the luminescent marker is luciferase. In another desirable embodiment, the fluorescent marker selectively stains dead or dying cells. Desirable examples of such fluorescent markers are Sytox® green and Sytox® orange.

In an additional desirable embodiment, the compound is a low molecular weight chemical compound.

In further desirable embodiments, the pathogen is a bacterial pathogen (e.g., *Pseudomonas, Xanthomonas, Erwinia,* or *Agrobacterium*). Desirably, the *Pseudomonas* is *Pseudomonas aeruginosa* or *Pseudomonas syringae.*

In other desirable embodiments, the pathogen is a fungal pathogen. Desirably, the fungal pathogen is *Candida, Cryptococcus, Fusarium, Rhodotorula, Aspergillus, Saccharomyces, Botrytis, Erysiphe, Alternaria, Rhytisma, Thielaviopsis, Verticillium, Aspergillus, Magnaporthe grisea, Rhizoctonia, Phakospora pachyrhizi, Puccinia, Diplocarpon, Sphaerotheca, Phytophthora, Venturia, Taphrina, Phythium, Penicillium, Urocystis,* or *Coniothyrium.* In particularly desirable embodiments, the *Candida* is *Candida albicans, Candida glabrata,* or *Candida parapsilosis,* the *Cryptococcus* is *Cryptococcus neoformans, Crytococcus gattii, Crytococcus grubii,* the *Rhodotorula* is *Rhodotorula mucilaginosa,* the *Saccharomyces* is *Saccharomyces cerevisiae,* or the *Aspergillus* is *Aspergillus flavus, Aspergillus fumigatus, Aspergillus nidulans, Aspergillus niger,* or *Aspergillus terreus,* the *Botrytis* is *Botrytis cinera,* or the *Fusarium* is *Fusarium oxysporum.*

In yet other desirable embodiments, the pathogen is a viral pathogen. Desirably, the viral pathogen is a nepovirus, poytvirus, tymovirus, ilarvirus, potexvirus, caulimovirus, tobravirus, closterovirus, carlavirus, cucumovirus, tobamovirus, comovirus, carmovirus, necrovirus, nucleorhabdovirus, tospovirus, luteovirus, fijivirus, or tenuivirus. In particularly desirable embodiments, the viral pathogen is tobacco mosaic virus, tobacco necrosis virus, potato leaf roll virus, potato virus X, potato virus Y, tomato spotted wilt virus, or tomato ring spot virus.

In further desirable embodiments, the pathogen is a protozoan or a *Mycobacterium.*

In yet another aspect, the invention features a method for identifying a compound that increases the lifespan of an invertebrate organism. This method involves (a) incubating an invertebrate organism in liquid medium in the presence of at least one candidate compound; and (b) identifying a compound that increases the lifespan of the invertebrate organism relative to a control organism not contacted with the candidate compound.

In desirable embodiments of this aspect of the invention, the identifying of step (c) involves using an automated microscope. In other desirable embodiments, the exposed invertebrate organism is transferred to the liquid medium by a robot.

In yet another desirable embodiment of this aspect of the invention, the identifying of step (c) involves using a fluorescent marker. Desirable, the fluorescent marker is green fluorescent protein, Nile Red, or MitoTracker. In other desirable embodiments, the fluorescent marker selectively stains dead or dying cells. Such a fluorescent marker desirably is Sytox® green or Sytox® orange.

In additional desirable embodiments, the identifying of step (c) involves determining whether the host organism is alive or dead. In yet another desirable embodiment of this aspect of the invention, the compound is a low molecular weight chemical compound.

In further desirable embodiments, the invertebrate host organism is a nematode (e.g., a *Caenorhabditis elegans* nematode). In yet further desirable embodiments of this aspect of the invention, the invertebrate host organism is a *Drosophila* larva (e.g., a *Drosophila melanogaster* larva). In other desirable embodiments the invertebrate host organism is a *Plutella xylostella* larva or a *Galleria mellonella* larva.

As used herein, the term "pharmaceutical composition" refers to a composition containing a compound of the invention (i.e., a compound of any of formulas (I)-(XV)), formulated with a pharmaceutically acceptable excipient, and manufactured or sold with the approval of a governmental regulatory agency as part of a therapeutic regimen for the treatment or prevention of disease in a mammal. Pharmaceutical compositions can be formulated, for example, for oral administration in unit dosage form (e.g., a tablet, capsule, caplet, gelcap, or syrup), for topical administration (e.g., as a cream, gel, lotion, or ointment), for intravenous administration (e.g., as a sterile solution free of particulate emboli and in a solvent system suitable for intravenous use), or any other formulation described herein.

As used herein, the term "treating" refers to administering a pharmaceutical composition for prophylactic and/or therapeutic purposes. To "prevent disease" refers to prophylactic treatment of a subject (e.g., a host organism or a plant) who is not yet ill or diseased, but who is susceptible to, or otherwise at risk of, a particular disease. To "treat disease" or use for "therapeutic treatment" refers to administering treatment to a subject already suffering from a disease to improve or stabilize the subject's condition. Thus, in the claims and embodiments, treating is the administration to a subject either for therapeutic or prophylactic purposes.

By "effective" amount is meant the amount of a pharmaceutical composition of the invention required to treat or prevent an infection or a disease associated with an infection, such as peripheral artery disease. The effective amount of a pharmaceutical composition of the invention used to practice the invention for therapeutic or prophylactic treatment of conditions caused by or contributed to by an infection varies depending upon the manner of administration, the age, body weight, and general health of the subject. Ultimately, the attending physician or veterinarian will decide the appropriate amount and dosage regimen. Such amount is referred to as an "effective" amount.

By "infection" is meant the invasion of a host by a pathogen (e.g., bacteria, fungi, protozoa, mycobacteria, or viruses). For example, the infection may include the excessive growth of microbes or viruses that are normally present in or on the body of a mammal or growth of microbes or viruses that are not normally present in or on a mammal or plant More generally, a microbial or viral infection can be any situation in which the presence of a microbial or viral population(s) is damaging to a host body. Thus, a mammal is "suffering" from an infection when an excessive amount of a microbial or viral population is present in or on the mammal's body, or when the presence of a microbial or viral population(s) is damaging the cells or other tissue of the mammal.

By a "pathogen" is meant a bacterium, *Mycobacterium*, protozoan, fungus, or virus that can cause an infection of a host organism. Examples of pathogenic bacteria include, without limitation, *Aerobacter, Aeromonas, Acinetobacter, Agrobacterium, Bacillus, Bacteroides, Bartonella, Bortella, Brucella, Calymmatobacterium, Campylobacter, Citrobacter, Clostridium, Cornyebacterium, Enterobacter, Erwinia, Escherichia, Francisella, Haemophilus, Hafnia, Helicobacter, Klebsiella, Legionella, Listeria, Morganella, Moraxella, Proteus, Providencia, Pseudomonas, Salmonella, Serratia, Shigella, Staphylococcus, Streptococcus, Treponema, Xanthomonas, Vibrio*, and *Yersinia*. In desirable embodiments, the bacterial pathogen is at Gram-positive coccus such as *Staphylococcus aureus, Staphylococcus epidermidis, Streptococcus pneumoniae, Streptococcus pyogenes, Moraxella catarrhalis, Haemophilus influenzae*, or *Enterococcus* spp. In other desirable embodiments the bacterial pathogen is a Gram-negative bacterium, such as, without limitation, *Pseudonomas aeruginosa, Klebsiella pneumoniae, Escherichia coli, Haemophilus influenzae, Citrobacter freundii*, or *Enterobacter* spp. In other desirable embodiments the bacterial pathogen is *Chlamydia pneumoniae* or *Chlamydia trachomatis*. In particularly desirable embodiments, the bacterial pathogen is *Enterococcus faecalis, Pseudomonas aeruginosa, Pseudomonas syringae, Salmonella typhimurium, Staphylococcus aureus, Staphylococcus epidermidis*, or *Staphylococcus saprophyticus*. In other particularly desirable embodiments, the bacterial pathogen is *Rickettsia prowazekii, Rickettsia rickettsii, Vibrio alginolyticus, Yersinia pestis, Bacillus anthracis, Clostridium botulinum, Brucella abortus, Brucella melitensis, Brucella suis, Burkholderia mallei, Burkholderia pseudomallei, Clostridium perfringens, Coxiella burnetii, Francisella tularensis, Shigella dysenteriae, Staphylococcus lugdunensis, Staphylococcus schleiferi, Staphylococcus caprae, Cowdria ruminantium, Mycoplasma capricolum, Mycoplasma mycoides mycoides, Candidatus Liberobacter africanus, Candidatus Liberobacter asiaticus, Ralstonia solanacearum, Xanthomonas oryzae* pv. *oryzicola*, or *Xylella fastidiosa*.

In desirable embodiments, a fungal pathogen is, without limitation, *Absidia corymbifera, Acremonium falciforme, A. kiliense, A. recifei, Ajellomyces dermatitidis, A. capsulata, Aspergillus* spp., (e.g., *A. flavus, A. fumigatus, A. nidulans, A. niger, A. terreus*), *Candida* spp. (e.g., *C. albicans, C. glabrata, C. guillermondii, C. krusei, C. parapsilosis, C. kefyr, C. tropicalis*), *Crytococcus* spp. (e.g., *C. neoformans, C. gattii, C. grubii*), *Cunninghamella elegans, Emmonsia parva, Epidermophyton floccosum, Exophialia dermitidis, E. werneckii, E. jeanselmei, E. spinifera, E. richardsiae, Filobasidiella neoformans, Fonsecaea compacta, F. pedrosoi, Histoplasma capsulatum, Leptoshaeria senegarlensis, Madurella mycetomatis, M. grisea, Malassezia furfur, Microsporum* spp, *Neotestudina rosatii, Paracoccidioides brasiliensis, Penicillium marneffei, Phialophora verrucosa, Piedraia hortae, Pneumocystis* spp., *Pseudallescheria boydii, Pyrenochaeta romeroi, Rhizomucor pusillus, Sporothrix schenckii, Trichophyton* spp, *Trichosporon beigelii, Wangiella dermatitidis*, or *Xylohypha bantiana*. In particularly desirable embodiments, the fungal pathogen is *Coccidioides posadasii, Coccidioides immitis, Fusarium sporotrichioides, Peronosclerospora philippinensis, Schlerophthora rayssiae* var *zeae*, or *Synchytrium endobioticum.*

In plants, in desirable embodiments, a fungal pathogen is, without limitation *Alternaria* spp. (for example, *A. brassicola* and *A. solani*), *Ascochyta* spp. (for example, *A. pisi*), *Aspergillus* spp., *Botrytis* spp. (for example, *B. cinerea*), *Cercospora* spp. (for example, *C. kikuchii* and *C. zaea-maydis*), *Colletotrichum* spp. (for example, *C. lindemuthianum*), *Coniothyrium* spp., *Diplocarpon* spp., *Diplodia* spp. (for example, *D. maydis*), *Erysiphe* spp. (for example, *E. graminis* f. sp. *graminis* and *E. graminis* f. sp. *hordei*), *Fusarium* spp. (for example, *F. nivale* and *F. oxysporum, F. graminearum, F. solani, F. monilforme*, and *F. roseum*), *Gaeumanomyces* spp. (for example, *G. graminis* f. sp. *tritici*), *Helminthosporium* spp. (for example, *H. turcicum, H. carbonum*, and *H. maydis*), *Macrophomina* spp. (for example, *M. phaseolina* and *Maganaporthe grisea*), *Nectria* spp. (for example, *N. heamatococca*), *Penicillium* spp., *Phakospora pachyrhizi, Peronospora* spp. (for example, *P. manshurica, P. tabacina*), *Phoma* spp. (for example, *P. betae*), *Phymatotrichum* spp. (for example, *P. omnivorum*), *Phytophthora* spp. (for example, *P. cinnamomi, P. cactorum, P. phaseoli, P. parasitica, P. citrophthora, P. megasperma* f. sp. *sojae*, and *P. infestans*), *Plasmopara* (for example, *P. viticola*), *Podosphaera* spp. (for example, *P. leucotricha*), *Puccinia* spp. (for example, *P. sorghi, P. striiformis, P. graminis* f. sp. *tritici, P. asparagi, P. recondita*, and *P. arachidis*), *Puthium* spp. (for example, *P. aphanidermatum*), *Pyrenophora* spp. (for example, *P. tritici-repentens*), *Pyricularia* spp. (for example, *P. oryzea*), *Pythium* spp. (for example, *P. ultimum*), *Rhizoctonia* spp. (for example, *R. solani* and *R. cerealis*), *Rhytisma* spp., *Scerotium* spp. (for example, *S. rolfsii*), *Sclerotinia* spp. (for example, *S. sclerotiorum*), *Septoria* spp. (for example, *S. lycopersici, S. glycines, S. nodorum* and *S. tritici*), *Sphaerotheca* spp., *Taphrina* spp., *Thielaviopsis* spp. (for example, *T. basicola*), *Uncinula* spp. (for example, *U. necator*), *Urocystis* spp., *Venturia* spp. (for example, *V. inaequalis*), or *Verticillium* spp. (for example, *V. dahliae* and *V. albo-atrum*).

In desirable embodiments, the viral pathogen is vesicular stomatitis virus (VSV). In particularly desirable embodiments, the viral pathogen is cercopithecine herpesvirus 1 (herpes B virus), Crimean-Congo haemorrhagic fever virus, Ebola virus, Lassa fever virus, Marburg virus, monkeypox virus, reconstructed 1918 influenza virus, South American haemorrhagic fever viruses (e.g., Flexal, Guanarito, Junin, Machupo, and Sabia), tick-borne encephalitis (e.g., Central European tick-borne encephalitis, Far Eastern tick-borne encephalitis, Kyasanur Forest disease, Omsk hemorrhagic fever, and Russian spring-summer encephalitis), variola major virus (e.g., smallpox virus), variola minor virus (e.g., alastrim), Eastern equine encephalitis virus, Hendra virus, Nipah virus, Rift Valley fever virus, Venezuelan equine encephalitis virus, African horse sickness virus, African swine fever virus, Akabane virus, avian influenza virus, Bluetongue virus, bovine spongiform encephalitis, camelpox virus, classical swine fever virus, foot-and-mouth disease virus, goat pox virus, Japanese encephalitis virus, lumpy skin disease virus, malignant catarrhal fever virus (alcelaphine herpesvirus type 1), Menangle virus, Newcastle disease virus, Peste des petits ruminants virus, rinderpest virus, sheep pox virus, or swine vesicular disease virus.

In plants, the viral pathogen desirably is a nepovirus, poytvirus, tymovirus, ilarvirus, potexvirus, caulimovirus, tobravirus, closterovirus, carlavirus, cucumovirus, tobamovirus, comovirus, carmovirus, necrovirus, nucleorhabdovirus, tospovirus, luteovirus, tenuivirus, tobacco mosaic virus, or leafroll virus. In particular desirable embodiments, the viral pathogen is tobacco mosaic virus, tobacco necrosis virus, potato leaf roll virus, potato virus X, potato virus Y, tomato spotted wilt virus, or tomato ring spot virus.

In other desirable embodiments, the *Mycobacterium* is *Mycobacterium tuberculosis.*

By a "compound," "candidate compound," or "factor" is meant a chemical, be it naturally-occurring or artificially-derived. Compounds may include, for example, peptides, polypeptides, synthetic organic molecules, naturally-occurring organic molecules, nucleic acid molecules, and components or combinations thereof. Desirably, a candidate compound is a low molecular weight chemical compound.

By "increases the lifespan of an organism" is meant an increase of at least 10% in the average age attained at the time of death of a population of organisms relative to a control population of the same organism. In desirable embodiments, the increase in age is at least 20%, 50%, 75%, 100%, or even 200%.

By "inhibiting a pathogen" is meant the ability of a candidate compound to decrease, suppress, attenuate, diminish, or arrest the development or progression of a pathogen-mediated disease or an infection in a eukaryotic host organism. Preferably, such inhibition decreases pathogenicity by at least 5%, more preferably by at least 25%, and most preferably by at least 50%, as compared to symptoms in the absence of candidate compound in any appropriate pathogenicity assay (for example, those assays described herein). In one particular example, inhibition may be measured by monitoring pathogenic symptoms in a host organism exposed to a test compound or extract, a decrease in the level of symptoms relative to the level of pathogenic symptoms in a host organism not exposed to the compound indicating compound-mediated inhibition of the pathogen. In other desirable embodiments, inhibiting a pathogen kills the pathogen.

By a "low molecular weight chemical compound" as used herein is meant a molecule of less than about 10 kDa molecular weight. The compound desirably is a synthetic organic or inorganic compound or a natural organic compound. Desirably, the molecular weight is less than about 1000 Da, more desirably less than about 750 Da, and most desirably less than about 500 Da. Nucleic acid molecules are specifically excluded from the definition of a low molecular weight chemical compound.

The invention features 15 lead compounds and, in some instances, their structural homologues for use as antimicrobials, antifungals, and antivirals. A compound is identified as a structural homologue of a lead compound if it has a significant number of substructures in common with that lead compound, such that the Tanimoto coefficient measuring structural similarity between those two compounds has a value of 0.85 or greater. The Tanimoto coefficient between two compounds is determined by calculating the ratio of the number of substructures held in common by the two compounds to the number of total substructures present in at least one of the two compounds. Tanimoto coefficients can also be calculated using hashed binary fingerprints wherein each fingerprint encodes the substructure composition of one compound and the Tanimoto coefficient is the ratio of the number of bits set to "1" in both compounds' fingerprints divided by the number of bits set to "1" in either compound's fingerprint using methods known in the art, e.g., such as Patterson et al. 1996 J. Med. Chem. 39:3049-3059; Matter et al. 1997 J. Med. Chem. 40:1219-1229; Potter et al. J. Med. Chem. 1998 41:478-488; Taylor et al. 1995 J. Chem. Inf. Comp. Sci. 35:59-67; Delaney et al., 1996 Mol. Diversity. 1:217-222. In the present invention, one such method using Daylight fingerprints is used to calculate Tanimoto coefficients and thus identify compounds present in publicly available chemical databases, e.g., such as PubChem and Chembank, that are structural homologues of a lead compound (Martin et al., 2002 J. Med. Chem. 45:4350-4358; Daylight Chemical Information Systems Inc.: Irvine, Calif.). A lead compound and structurally homologous compound having a Tanimoto coefficient of 0.85 or greater as calculated using Daylight fingerprints are known to have a probability of 30% or greater, e.g., such as 50% or 75%, of having the same biological activity, depending in part on the potency of the lead compound, e.g., having an IC50 less than 10 micromolar or having an IC50 between 10 micromolar and 100 micromolar, and in part on the biological activity under consideration, as known in the art, e.g., as described in Martin et al., 2002 J. Med. Chem. 45:4350-4358 and Klekota et al. 2005 J. Chem. Info. Model. 45:1824-1836.

In the generic descriptions of compounds of this invention, the number of atoms of a particular type in a substituent group is generally given as a range, e.g., an alkyl group containing from 1 to 4 carbon atoms or $C_{1-4}$ alkyl. Reference to such a range is intended to include specific references to groups having each of the integer number of atoms within the specified range. For example, an alkyl group from 1 to 4 carbon atoms includes each of $C_1$, $C_2$, $C_3$, and $C_4$. A $C_{1-4}$ heteroalkyl, for example, includes from 1 to 3 carbon atoms in addition to one or more heteroatoms. Other numbers of atoms and other types of atoms may be indicated in a similar manner.

As used herein, the terms "alkyl" and the prefix "alk-" are inclusive of both straight chain and branched chain groups and of cyclic groups, i.e., cycloalkyl. Exemplary cyclic groups include cyclopropyl, cyclobutyl, cyclopentyl, and cyclohexyl groups. The $C_{1-4}$ alkyl group may be substituted or unsubstituted. Exemplary substituents include alkoxy, aryloxy, sulfhydryl, alkylthio, arylthio, halide, hydroxyl, fluoroalkyl, perfluoroalkyl, amino, aminoalkyl, disubstituted amino, quaternary amino, hydroxyalkyl, carboxyalkyl, and carboxyl groups. $C_{1-4}$ alkyls include, without limitation, methyl; ethyl; n-propyl; isopropyl; cyclopropyl; cyclopropylmethyl; cyclopropylethyl; n-butyl; iso-butyl; sec-butyl; tert-butyl; and cyclobutyl.

By "$C_{2-4}$ alkenyl" is meant a branched or unbranched hydrocarbon group containing one or more double bonds and having from 2 to 4 carbon atoms. The $C_{2-4}$ alkenyl group may be substituted or unsubstituted. Exemplary substituents include alkoxy, aryloxy, sulfhydryl, alkylthio, arylthio, halide, hydroxyl, fluoroalkyl, perfluoroalkyl, amino, aminoalkyl, disubstituted amino, quaternary amino, hydroxyalkyl, carboxyalkyl, and carboxyl groups. $C_{2-4}$ alkenyls include, without limitation, vinyl; allyl; 2-cyclopropyl-1-ethenyl; 1-propenyl; 1-butenyl; 2-butenyl; 3-butenyl; 2-methyl-1-propenyl; and 2-methyl-2-propenyl.

By "$C_{2-4}$ alkynyl" is meant a branched or unbranched hydrocarbon group containing one or more triple bonds and having from 2 to 4 carbon atoms. The $C_{2-4}$ alkynyl group may be substituted or unsubstituted. Exemplary substituents include alkoxy, aryloxy, sulfhydryl, alkylthio, arylthio, halide, hydroxy, fluoroalkyl, perfluoroalkyl, amino, aminoalkyl, disubstituted amino, quaternary amino, hydroxyalkyl, carboxyalkyl, and carboxyl groups. $C_{2-4}$ alkynyls include, without limitation, ethynyl, 1-propynyl, 2-propynyl, 1-butynyl, 2-butynyl, and 3-butynyl.

By "$C_{2-6}$ heterocyclyl" is meant a stable 5- to 7-membered monocyclic or 7- to 14-membered bicyclic heterocyclic ring which is saturated partially unsaturated or unsaturated (aromatic), and which consists of 2 to 6 carbon atoms and 1, 2, 3 or 4 heteroatoms independently selected from the group consisting of N, O, and S and including any bicyclic group in which any of the above-defined heterocyclic rings is fused to a benzene ring. The heterocyclyl group may be substituted or unsubstituted. Exemplary substituents include alkoxy, aryloxy, sulfhydryl, alkylthio, arylthio, halide, hydroxy, fluoroalkyl, perfluoralkyl, amino, aminoalkyl, disubstituted amino, quaternary amino, hydroxyalkyl, carboxyalkyl, and carboxyl groups. The nitrogen and sulfur heteroatoms may optionally be oxidized. The heterocyclic ring may be covalently attached via any heteroatom or carbon atom which results in a stable structure, e.g., an imidazolinyl ring may be linked at either of the ring-carbon atom positions or at the nitrogen atom. A nitrogen atom in the heterocycle may optionally be quaternized. Preferably when the total number of S and O atoms in the heterocycle exceeds 1, then these heteroatoms are not adjacent to one another. Heterocycles include, without limitation, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, without limitation, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl.

By "$C_{6-12}$ aryl" is meant an aromatic group having a ring system comprised of carbon atoms with conjugated π electrons (e.g., phenyl). The aryl group has from 6 to 12 carbon atoms. Aryl groups may optionally include monocyclic, bicyclic, or tricyclic rings, in which each ring desirably has five or six members. The aryl group may be substituted or unsubstituted. Exemplary substituents include alkyl, hydroxy, alkoxy, aryloxy, sulfhydryl, alkylthio, arylthio, halide, fluoroalkyl, carboxyl, hydroxyalkyl, carboxyalkyl, amino, aminoalkyl, monosubstituted amino, disubstituted amino, and quaternary amino groups.

By "C$_{7-14}$ alkaryl" is meant an alkyl substituted by an aryl group (e.g., benzyl, phenethyl, or 3,4-dichlorophenethyl) having from 7 to 14 carbon atoms.

By "C$_{3-10}$ alkheterocyclyl" is meant an alkyl substituted heterocyclic group having from 7 to 14 carbon atoms in addition to one or more heteroatoms (e.g., 3-furanylmethyl, 2-furanylmethyl, 3-tetrahydrofuranylmethyl, or 2-tetrahydrofuranylmethyl).

By "C$_{1-4}$ heteroalkyl" is meant a branched or unbranched alkyl, alkenyl, or alkynyl group having from 1 to 4 carbon atoms in addition to 1, 2, or 3 heteroatoms independently selected from the group consisting of N, O, S, and P. Heteroalkyls include, without limitation, tertiary amines, secondary amines, ethers, thioethers, amides, thioamides, carbamates, thiocarbamates, hydrazones, imines, phosphodiesters, phosphoramidates, sulfonamides, and disulfides. A heteroalkyl may optionally include monocyclic, bicyclic, or tricyclic rings, in which each ring desirably has three to six members. The heteroalkyl group may be substituted or unsubstituted. Exemplary substituents include alkoxy, aryloxy, sulfhydryl, alkylthio, arylthio, halide, hydroxyl, fluoroalkyl, perfluoroalkyl, amino, aminoalkyl, disubstituted amino, quaternary amino, hydroxyalkyl, hydroxyalkyl, carboxyalkyl, and carboxyl groups.

By "acyl" is meant a chemical moiety with the formula R—C(O)—, wherein R is selected from C$_{1-4}$ alkyl, C$_{2-4}$ alkenyl, C$_{2-4}$ alkynyl, C$_{2-6}$ heterocyclyl, C$_{6-12}$ aryl, C$_{7-14}$ alkaryl, C$_{3-10}$ alkheterocyclyl, or C$_{1-4}$ heteroalkyl.

By "halide" is meant bromine, chlorine, iodine, or fluorine.

By "fluoroalkyl" is meant an alkyl group that is substituted with a fluorine.

By "perfluoroalkyl" is meant an alkyl group consisting of only carbon and fluorine atoms.

By "carboxyalkyl" is meant a chemical moiety with the formula —(R)—COOH, wherein R is selected from C$_{1-4}$ alkyl, C$_{2-4}$ alkenyl, C$_{2-4}$ alkynyl, C$_{2-6}$ heterocyclyl, C$_{6-12}$ aryl, C$_{7-14}$ alkaryl, C$_{3-10}$ alkheterocyclyl, or C$_{1-4}$ heteroalkyl.

By "hydroxyalkyl" is meant a chemical moiety with the formula —(R)—OH, wherein R is selected from C$_{1-4}$ alkyl, C$_{2-4}$ alkenyl, C$_{2-4}$ alkynyl, C$_{2-6}$ heterocyclyl, C$_{6-12}$ aryl, C$_{7-14}$ alkaryl, C$_{3-10}$ alkheterocyclyl, or C$_{1-4}$ heteroalkyl.

By "alkoxy" is meant a chemical substituent of the formula —OR, wherein R is selected from C$_{1-4}$ alkyl, C$_{2-4}$ alkenyl, C$_{2-4}$ alkynyl, C$_{2-6}$ heterocyclyl, C$_{6-12}$ aryl, C$_{7-14}$ alkaryl, C$_{3-10}$ alkheterocyclyl, or C$_{1-4}$ heteroalkyl.

By "aryloxy" is meant a chemical substituent of the formula —OR, wherein R is a C$_{6-12}$ aryl group.

By "alkylthio" is meant a chemical substituent of the formula —SR, wherein R is selected from C$_{1-4}$ alkyl, C$_{2-4}$ alkenyl, C$_{2-4}$ alkynyl, C$_{2-6}$ heterocyclyl, C$_{6-12}$ aryl, C$_{7-14}$ alkaryl, C$_{3-10}$ alkheterocyclyl, or C$_{1-4}$ heteroalkyl.

By "arylthio" is meant a chemical substituent of the formula —SR, wherein R is a C$_{6-12}$ aryl group.

By "quaternary amino" is meant a chemical substituent of the formula —(R)—N(R')(R")(R''')$^+$, wherein R, R', R", and R''' are each independently an alkyl, alkenyl, alkynyl, or aryl group. R may be an alkyl group linking the quaternary amino nitrogen atom, as a substituent, to another moiety. The nitrogen atom, N, is covalently attached to four carbon atoms of alkyl and/or aryl groups, resulting in a positive charge at the nitrogen atom.

Other features and advantages of the invention will be apparent from the following Detailed Description, the Drawings, and the Claims.

BRIEF DESCRIPTION OF THE DRAWINGS

FIG. 11A is a graph depicting the Kaplan-Meier survival curves of wild-type N2 *C. elegans* feeding continuously on lawns of *E. faecalis* (Efs) V583 (▲) or *E. faecium* (Efm) DO (▼). Nematodes feeding for 24 hours on *E. faecalis* and subsequently transferred to lawns of *E. faecium* (■) die with an LT50 of 14.9 days. Error bars equal SEM. FIG. 11B is a graph depicting the Kaplan-Meier survival curves of *E. faecalis* infected N2 *C. elegans* transferred to lawns of *E. faecium* on media containing tetracycline at 10 µg/ml (▲, $p<0.0001$), 2 µg/ml (▼, $p<0.0014$), 0.4 µg/ml (♦, $p<0.06$), 0.08 µg/ml (●, $p=0.56$), or no tetracycline (■). FIG. 11C is a graph showing the antibiotic concentrations required to promote rescue of *E. faecalis* infected N2 nematodes. Survival was measured 13 days post-infection after treatment with tetracycline, vancomycin, or ciprofloxacin. Error bars are standard deviations. FIG. 11D is a graph depicting the Kaplan-Meier survival curve of glp-4;sek-1 nematodes infected for 12 hours on *E. faecalis* OG1RF and transferred to BHI media containing 20 µg/ml tetracycline (▲), 40 µg/ml vancomycin (▼), or no additional antibiotic (■). Error bars equal SEM.

FIG. 12A is a graph depicting the Kaplan-Meier survival curves of glp-4;sek-1 nematodes that were infected with *E. faecalis* OG1RF (■, ▲) or the two component quorum sensing regulator mutant OG1RF ΔfsrB (▼) or with the *E. faecium* strain 11M12 (●). OG1RF infected nematodes were treated with 0 (■) or 20 µg/ml (▲) tetracycline. Error bars equal SEM. FIG. 12B is a graph depicting the Kaplan-Meier survival curves of glp-4;sek-1 nematodes that were infected with the cytolysin (Cyl) producing *E. faecalis* strain MMH594 (▲,♦) or the *E. faecium* strain 11M12 (●). Cyl infected nematodes were treated with 0 (▲) or 20 µg/ml (♦) tetracycline. FIG. 12C is a bar chart showing the bacterial load in the nematode intestinal tract after antibiotic treatment. *E. faecalis* infected nematodes were treated in liquid media containing 20 µg/ml ampicillin or tetracycline and the number of CFU per worm was determined. Error bars equal standard deviations.

FIG. 16A shows that killing of 60-70 *C. elegans* N2 wild type nematodes takes place mostly on approximately day 3 of the assay, and in over one third of the nematodes, killing is associated with matricidal effect involving the premature hatching of eggs in the *C. elegans* uterus. Survival of 60-70 *C. elegans* glp-4;sek-1 nematodes in liquid pathogen-free media, after feeding on lawns of *C. albicans* strain DAY185 is significantly shorter compared to the strain glp-4 (P<0.001). 30-40 control N2 nematodes were exposed to *E. coli* OP50. FIG. 16B shows survival of *C. elegans* glp-4;sek-1 feeding on lawns of *C. albicans* ATCC#90028, *C. parapsilosis* ATCC#20019 or *C. krusei* ATCC#6258. P<0.001 for each of the yeast strains compared to control nematodes that were exposed to *E. coli* OP50. 60-70 worms were exposed to each pathogen or *E. coli*.

FIG. 17A shows that addition of caspofungin (8 μg/ml), amphotericin B (16 μg/ml) and fluconazole (32 μg/ml) were effective against the fluconazole-susceptible *C. albicans* strain MLR62. FIG. 17B shows that only caspofungin and amphotericin B were effective against *C. krusei* strain ATCC#6258, the most fluconazole-resistant strain tested (P<0.001). FIG. 17C shows that caspofungin (8 μg/ml), amphotericin B (16 μg/ml), and fluconazole (32 μg/ml) prolonged the survival of *C. elegans* glp-4;sek-1 nematodes (P<0.001) against *C. parasilosis* ATCC#20019. FIG. 17D shows that the life span of nematodes was significantly longer in 4 μg/mL and 32 μg/mL fluconazole compared to those in no antifungal (P=0.0001 and P<0.0001, respectively) against *C. parasilosis* ATCC#20019. However, at very high concentrations (100 μg/mL) nematodes died faster, probably because of toxicity (P=0.01, compared to those in no antifungal). 60-70 nematodes were used for each condition.

DETAILED DESCRIPTION

Figure 1:
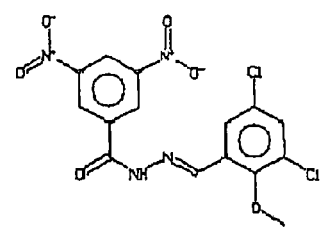
FIG. 1 depicts the structure of compound A1 and compounds A2-A9, which are homologues of A1.
Figure 1:
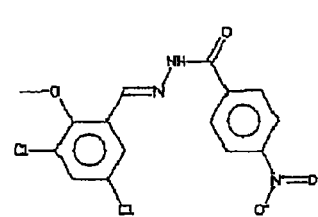
Figure 1:
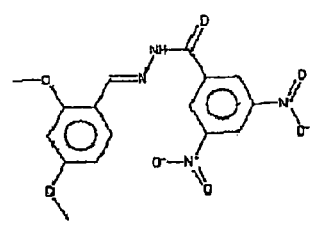
Figure 1:
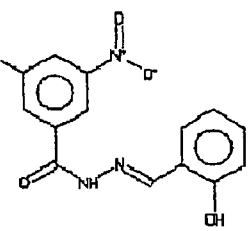
Figure 1:
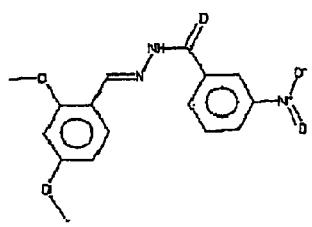
Figure 1:
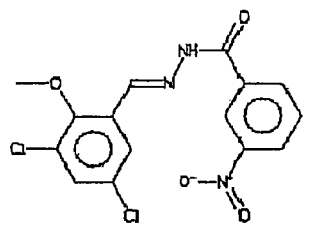
Figure 1:
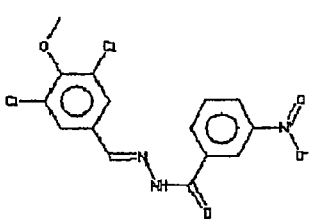
Figure 1:
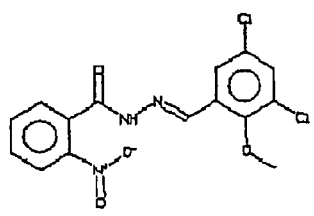
Figure 1:
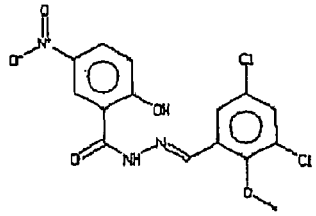

To discover novel antimicrobial, antifungal, and antiviral compounds we devised screens to identify compounds that promote the survival of the model laboratory nematode *Caenorhabditis elegans* infected with the human opportunistic pathogen *Enterococcus faecalis* and with *Candida* strains. The screening methods can also be used to identify compounds that increase the lifespan of an organism.

*E. faecalis* colonizes the nematode intestinal tract forming a persistent lethal infection. Death of infected nematodes was prevented by antibiotic treatment in a dose-dependent manner and antibiotic treatment markedly reduced the number of bacteria colonizing the nematode intestine. To facilitate high throughput screening of compound libraries, we adapted the traditional agar-based *C. elegans*-*E. faecalis* infection assay so that it could be carried out in liquid medium in standard microtiter plates. An important feature of the assay is that the first assay endpoint is nematode survival, which automatically eliminates highly toxic compounds that affect nematode viability. We used this simple infection system to screen 6000 synthetic compounds. We identified 16 compounds that promoted nematode survival. Some of the compounds inhibited *E. faecalis* growth in vitro, but in contrast to traditional antibiotics, the in vivo effective dose of many of these compounds was significantly lower than the minimum inhibitory concentration needed to prevent the growth of *E. faecalis* in vitro. Moreover, many of the compounds had little or no affect on in vitro bacterial growth. Our findings indicate that the whole-animal *C. elegans* screen not only identifies traditional antibiotics, but also compounds that target bacterial virulence or stimulate host defense.

We have also found that *Candida albicans*, as well as other *Candida* strains, form persistent infections in the *C. elegans* intestine and can kill *C. elegans*. We used these findings to develop a *C. elegans*-based infection model that can be performed in standard 96-well plates in liquid media, thereby enabling automated addition of compounds. An important feature of the assay is that the first assay endpoint is nematode survival, which automatically eliminates highly toxic compounds that affect nematode viability. Moreover, important components of *Candida* pathogenesis in mammals, such as filament formation, are involved in nematode killing and filamentation becomes apparent as the nematode dies, providing a second clinically relevant endpoint. As described herein, we screened a total of 1,266 compounds and identified 15 that prolonged nematode survival and completely or almost completely inhibited filamentation. An additional 52 of the compounds prolonged nematode survival but had no or minimal effect on filamentation.

High-Throughput Screening

Whole-organism (e.g., *C. elegans* or plant seedling) screens have several advantages compared to in vitro screens that use planktonic cells. Some virulence traits are induced only in the host and, therefore, the identification of compounds that are effective against these virulence traits may require detection in vivo. Also, the whole-organism approach provides relatively unambiguous assay endpoints (e.g., survival or death of the animal or plant), allows the use of liquid handling robots for filling assay plates and for pin transfer of compounds from library stock plates to assay plates, and permits automated or semi-automated readout using plate readers or automated imaging microscopes. The whole-organism assays using, e.g., invertebrates, also have many advantages compared to screens using mammalian models. The study of pathogenesis in mammals is complicated by difficulty of handling, long reproductive cycles, small brood sizes, complexity of mammalian hosts, high cost, and ethical considerations.

Despite the potential value of live animals (e.g., *C. elegans* or *Drosophila* or moth larvae) or plant seedlings for gene, drug, or drug-target discovery, screens using whole animals, prior to the present invention, were generally carried out manually and, therefore, were extremely labor intensive. In the laboratory, for example, *C. elegans* assays are typically carried out by transferring nematodes from lawns of *Escherichia coli* strain OP50 (their normal laboratory food) to lawns of pathogenic bacteria or yeast grown on solid agar media. However, screening chemical libraries using an agar-based *C. elegans* killing assay is not readily compatible with the use of robots for filling assay plates and pin transfer of compounds, homogeneous distribution of chemicals in the medium, or the use of automated plate readers or automated screening microscopes to monitor host (e.g., nematode) survival. The previously available liquid assays also had their deficiencies, as these assays used volumes that were incompatible with high-throughput screens of chemical libraries. The methods for identifying candidate compounds described herein are automated, performed in a small volume of liquid (e.g., 20-100 μl), and the scoring of the compounds is automated and quantitative.

The methods for identifying a candidate compound described herein feature exposing a host organism to a pathogen and incubating the exposed invertebrate animal or plant host organism in a liquid medium in the presence of at least one candidate compound. In desirable embodiments, the invertebrate animal or plant host is contacted with the candidate compound prior to being exposed to the pathogen. A candidate compound that inhibits the pathogen in the host organism may be identified depending on the survival or death of the host organism. The host organism may be, e.g., a nematode (e.g., *C. elegans*). The nematode may have a mutation in the mitogen-activated protein kinase (MAPK) pathway (e.g., a sek-1 mutation) or may have a temperature-sensitive sterile mutation (e.g., a glp-4 mutation). The invertebrate host organisms may also be, e.g., *Drosophila* larvae, *Plutella xylostella* larvae, *Galleria mellonella* larvae, or a plant seedling (e.g., a *Arabidopsis thaliana* seedling). The pathogen that infects the host organism may be, e.g., a bacterial pathogen (e.g., *Enterococcus faecalis, Pseudomonas aeruginosa, Pseudomonas syringae, Salmonella typhimurium*, or *Staphylococcus aureus* or *epidermidis*), a fungal pathogen (e.g., *Candida albicans, Candida glabrata, Candida parapsilosis, Crytococcus* spp. (e.g., *C. neoformans, C. gattii, C. grubii*), *Rhodotorula mucilaginosa, Fusarium oxysporum, Botrytis cinerea*, or *Saccharomyces cerevisiae*), a viral pathogen (e.g., vesicular stomatitis virus), a protozoan, or a mycobacterium. The exposed invertebrate host organism may be incubated with at least one candidate compound in a liquid medium. The liquid medium may include, e.g., a buffer (e.g., M9 buffer), brain heart infusion media, MS (Murashige and Skoog) medium, cholesterol, and an antibiotic (e.g., kanamycin).

The invention also features a container that includes an invertebrate animal or a plant host organism that is infected with a pathogen, liquid media, and a candidate compound. The container may be, e.g., a 24-well, 48-well, 96-well plate, a 384-well plate, a 1536-well plate, a 3456-well plate, or any other suitable container. Each well of the container may contain a different candidate compound.

The methods of screening described herein may also be used to enable quantitative analysis of a wide range of biological processes such as the response to different types of biotic (e.g. pathogens) or abiotic (e.g., exposure to heavy metals, ultraviolet radiation, or heat) stresses that affect viability. Traditional longevity studies may be performed using the methods described herein, which would allow for the automated screening of any phenotypic read-out based on fluorescent markers (e.g., green fluorescent protein, Nile Red, MitoTracker (Invitrogen), or Sytox® green or orange). Automated screening of ectopic fluorescent and luminescent markers such as GFP and luciferase could facilitate the finding of genes that affect, e.g., reproduction, cell proliferation, cell death, fat accumulation, insulin signaling, pathogen resistance, and neurotransmission. In addition, the study of chemical or genetic perturbations that affect growth rate or body size could be performed using the methods described herein.

Using these screens, we have identified compounds that are useful for the treatment of infections (compounds of formulas (I)-(XV), below).

Test Extracts and Candidate Compounds

In general, novel antimicrobial, antifungal, or antiviral drugs are identified from large libraries of both natural-product or synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their antimicrobial, antifungal, or antiviral activity should be employed whenever possible.

When a crude extract is found to have antimicrobial, antifungal, or antiviral activity, further fractionation of the positive lead extract is necessary to isolate chemical constituents responsible for the observed effect. Thus, the goal of the extraction, fractionation, and purification process is the careful characterization and identification of a chemical entity within the crude extract having antimicrobial, antifungal, or antiviral activity. Methods of fractionation and purification of such heterogenous extracts are known in the art. If desired, compounds shown to be useful agents for the treatment of pathogenicity are chemically modified according to methods known in the art.

Synthesis of Compounds

The synthesis of the compounds of the invention may involve selective protection and deprotection of alcohols, amines, sulfhydryls and carboxylic acid functional groups in one or more reactants. For example, commonly used protecting groups for amines include carbamates, such as tert-butyl, benzyl, 2,2,2-trichloroethyl, 2-trimethylsilylethyl, 9-fluorenylmethyl, allyl, and m-nitrophenyl. Other commonly used protecting groups for amines include amides, such as formamides, acetamides, trifluoroacetamides, sulfonamides, trifluoromethanesulfonyl amides, trimethylsilylethanesulfonamides, and tert-butylsulfonyl amides. Examples of commonly used protecting groups for carboxylic acids include esters, such as methyl, ethyl, tert-butyl, 9-fluorenylmethyl, 2-(trimethylsilyl)ethoxy methyl, benzyl, diphenylmethyl, O-nitrobenzyl, ortho-esters, and halo-esters. Examples of commonly used protecting groups for alcohols include ethers, such as methyl, methoxymethyl, methoxyethoxymethyl, methylthiomethyl, benzyloxymethyl, tetrahydropyranyl, ethoxyethyl, benzyl, 2-napthylmethyl, O-nitrobenzyl, P-nitrobenzyl, P-methoxybenzyl, 9-phenylxanthyl, trityl (including methoxy-trityls), and silyl ethers. Examples of commonly used protecting groups for sulfhydryls include many of the same protecting groups used for hydroxyls. In addition, sulfhydryls can be protected in a reduced form (e.g., as disulfides) or an oxidized form (e.g., as sulfonic acids, sulfonic esters, or sulfonic amides). Protecting groups can be chosen such that selective conditions (e.g., acidic conditions, basic conditions, catalysis by a nucleophile, catalysis by a lewis acid, or hydrogenation) are required to remove each, exclusive of other protecting groups in a molecule. The conditions required for the addition of protecting groups to amine, alcohol, sulfhydryl, and carboxylic acid functionalities and the conditions required for their removal are provided in detail in "T. W. Green and P. G. M. Wuts: Protective Groups in Organic Synthesis" (2$^{nd}$ ed., 1991, John Wiley & Sons) and "P. J. Kocienski: Protecting Groups" (1994 Georg Thieme Verlag); each of which is hereby incorporated by reference.

In the synthetic schemes provided herein, the use of protecting groups is indicated in a structure by the letter P, where P for any amine, aldehyde, carboxylic acid, sulfhydryl, or alcohol may be any of the protecting groups listed above.

Compounds of Formula I

Compounds of the invention include compounds of formula (I).

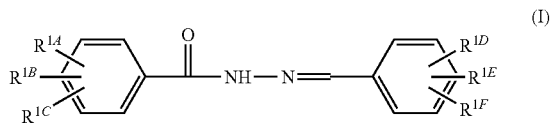

In formula (I) each of $R^{1A}$, $R^{1B}$, $R^{1C}$, $R^{1D}$, $R^{1E}$, and $R^{1F}$ is, independently, selected from H, halide, nitro, $C_{1-4}$ alkyl, $C_{2-4}$ alkenyl, $C_{2-4}$ alkynyl, $OR^{1G}$, $OC(O)R^{1H}$, $NR^{1I}R^{1J}$, $NHC(O)R^{1K}$, $NHC(S)R^{1L}$, $NHC(O)OR^{1M}$, $NHC(S)OR^{1N}$, $NHC(O)NHR^{1O}$, $NHC(S)NHR^{1P}$, $NHC(O)SR^{1Q}$, $NHC(S)SR^{1R}$, $NHS(O)_2R^{1S}$, $C(O)OR^{1T}$, and $C(O)NHR^{1U}$; and each of $R^{1G}$, $R^{1H}$, $R^{1I}$, $R^{1J}$, $R^{1K}$, $R^{1L}$, $R^{1M}$, $R^{1N}$, $R^{1O}$, $R^{1P}$, $R^{1Q}$, $R^{1R}$, $R^{1S}$, $R^{1T}$, and $R^{1U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. Compounds of formula (I) include compounds A1-A9 (see FIG. 1).

Compounds of formula (I) can by prepared by hydrazinolysis of an activated benzoic acid derivative with hydrazine hydrate, followed by condensation with a benzaldehyde derivative to give the desired hydrazide (see Scheme 1).

Scheme 1

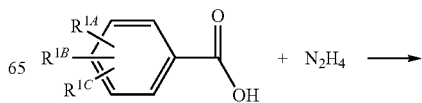

-continued

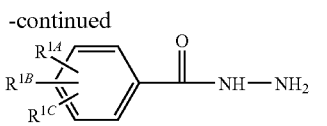

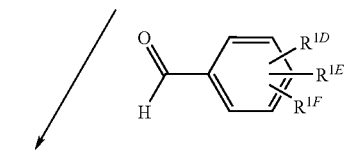

Compounds of Formula II
Compounds of the invention include compounds of formula (II).

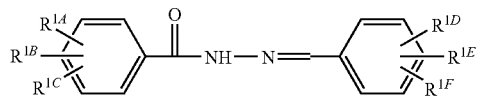
(II)

Figure 2:
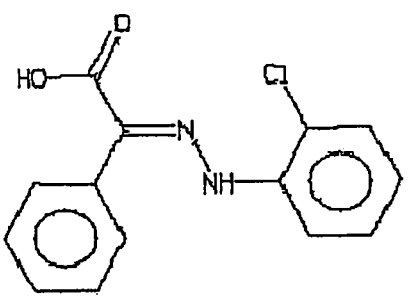
FIG. 2 depicts the structure of compound B1 and compound B2, which is a homologue of B1.
Figure 2:
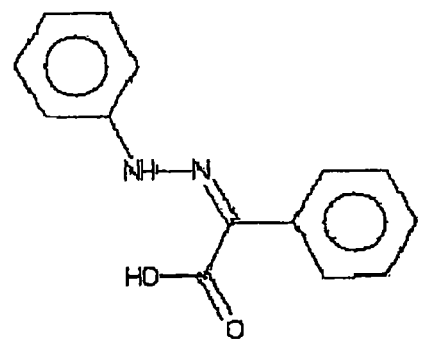

In formula (II) each of $R^{2A}$, $R^{2B}$, $R^{2C}$, $R^{2D}$, $R^{2E}$, $R^{2F}$ is, independently, selected from H, halide, nitro, $C_{1-4}$ alkyl, $C_{2-4}$ alkenyl, $C_{2-4}$ alkynyl, $OR^{2G}$, $OC(O)R^{2H}$, $NR^{2I}R^{2J}$, $NHC(O)R^{2K}$, $NHC(S)R^{2L}$, $NHC(O)OR^{2M}$, $NHC(S)OR^{2N}$, $NHC(O)NHR^{2O}$, $NHC(S)NHR^{2P}$, $NHC(O)SR^{2Q}$, $NHC(S)SR^{2R}$, $NHS(O)_2R^{2S}$, $C(O)OR^{2T}$, and $C(O)NHR^{2U}$; $X^2$ is independently selected from $OR^{2G}$, $OC(O)R^{2H}$, $NR^{2I}R^{2J}$, $NHC(O)R^{2K}$, $NHC(S)R^{2L}$, $NHC(O)OR^{2M}$, $NHC(S)OR^{2N}$, $NHC(O)NHR^{2O}$, $NHC(S)NHR^{2P}$, $NHC(O)SR^{2Q}$, $NHC(S)SR^{2R}$, and $NHS(O)_2R^{2S}$; and each of $R^{2G}$, $R^{2H}$, $R^{2I}$, $R^{2J}$, $R^{2K}$, $R^{2L}$, $R^{2M}$, $R^{2N}$, $R^{2O}$, $R^{2P}$, $R^{2Q}$, $R^{2R}$, $R^{2S}$, $R^{2T}$, and $R^{2U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. Compounds of formula (II) include compounds B1 and B2 (see FIG. 2).

Compounds of formula (II) can be prepared by condensation of a phenylglyoxylic acid derivative with a phenylhydrazine derivative to form the desired hydrazone (see Scheme 2).

Scheme 2

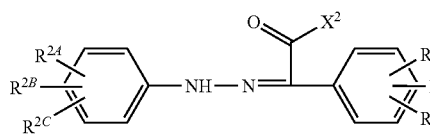

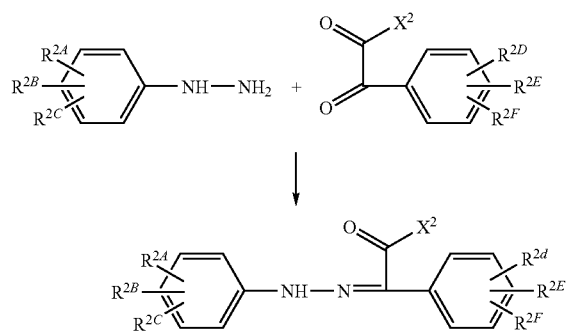

Phenylglyoxylic acid derivatives can be prepared by oxidation of the corresponding mandelic acid derivative or styrene derivative (see, for example, Hurd et al., J. Am. Chem. Soc. 61:2979 (1939)).

Compounds of Formula III
Compounds of the invention include compounds of formula (III).

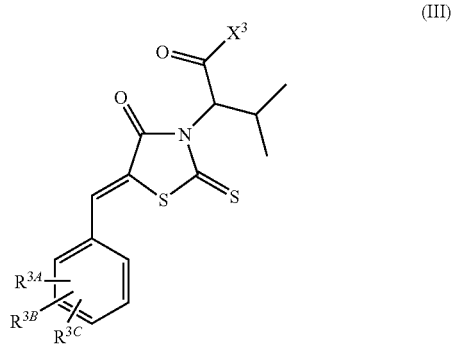
(III)

Figure 3:
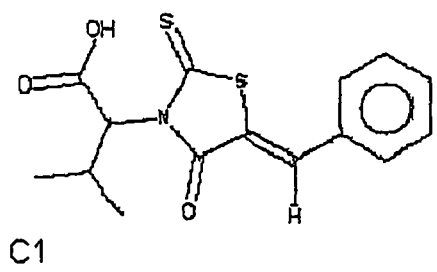
FIG. 3 depicts the structure of compound C1 and compounds C2-C7, which are homologues of C1.
Figure 3:
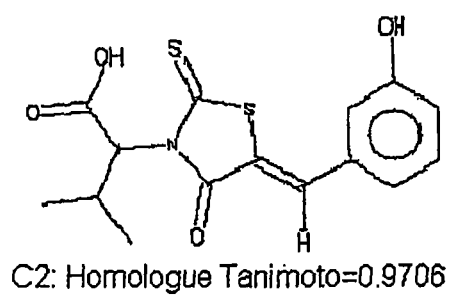
Figure 3:
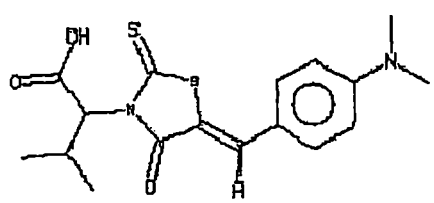
Figure 3:
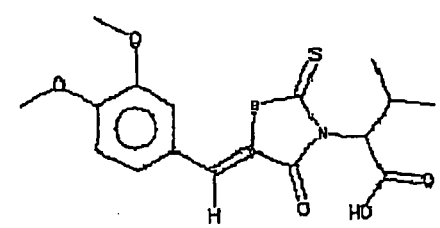
Figure 3:
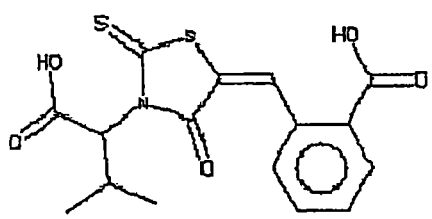
Figure 3:
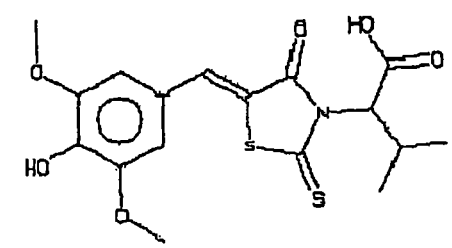
Figure 3:
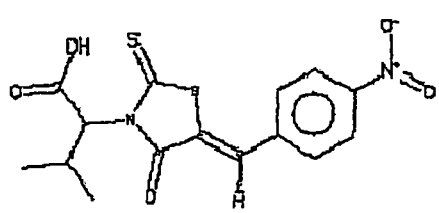

In formula (III) each of $R^{3A}$, $R^{3B}$, and $R^{3C}$ is, independently, selected from H, halide, nitro, $C_{1-4}$ alkyl, $C_{2-4}$ alkenyl, $C_{2-4}$ alkynyl, $OR^{3G}$, $OC(O)R^{3H}$, $NR^{3I}R^{3J}$, $NHC(O)R^{3K}$, $NHC(S)R^{3L}$, $NHC(O)OR^{3M}$, $NHC(S)OR^{3N}$, $NHC(O)NHR^{3O}$, $NHC(S)NHR^{3P}$, $NHC(O)SR^{3Q}$, $NHC(S)SR^{3R}$, $NHS(O)_2R^{3S}$, $C(O)OR^{3T}$, and $C(O)NHR^{3U}$; $X^3$ is independently selected from $OR^{3G}$, $OC(O)R^{3H}$, $NR^{3I}R^{3J}$, $NHC(O)R^{3K}$, $NHC(S)R^{3L}$, $NHC(O)OR^{3M}$, $NHC(S)OR^{3N}$, $NHC(O)NHR^{3O}$, $NHC(S)NHR^{3P}$, $NHC(O)SR^{3Q}$, $NHC(S)SR^{3R}$, and $NHS(O)_2R^{3S}$; and each of $R^{3G}$, $R^{3H}$, $R^{3I}$, $R^{3J}$, $R^{3K}$, $R^{3L}$, $R^{3M}$, $R^{3N}$, $R^{3O}$, $R^{3P}$, $R^{3Q}$, $R^{3R}$, $R^{3S}$, $R^{3T}$, and $R^{3U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. Formula (III) includes compound C1-C7 (see FIG. 3).

Compounds of formula III can be synthesized using methods analogous to those described by Kopiichuk I. I., Med. Inst., Lvov, Farmatsevtichnii Zhurnal (Kiev) 21:7-10 (1966). First, 3-(1-Carboxy-2-methylpropyl)rhodanine can be prepared by mixing 0.3 mole valine in 1 portion of KOH solution (3 moles in 80 ml $H_2O$) with 0.3 mole $CS_2$ in the same amount of KOH solution. After 3 hours of mixing, 0.3 mole $ClCH_2CO_2H$ neutralized by $K_2CO_3$ is added to the mixture and the reaction is stirred for 20-30 minutes, followed by neutralization with concentration HCl. The reaction is heated at 90° for 20-30 minutes and the 3-(1-Carboxy-2-methylpropyl)rhodanine can be isolated as a crystalline solid. Subsequent condensation with aromatic aldehydes can yield compounds of formula (III).

Compounds of Formula IV
Compounds of the invention include compounds of formula (IV).

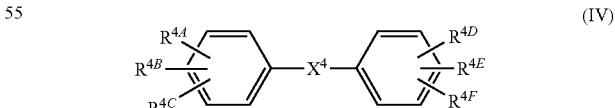
(IV)

Figure 4:
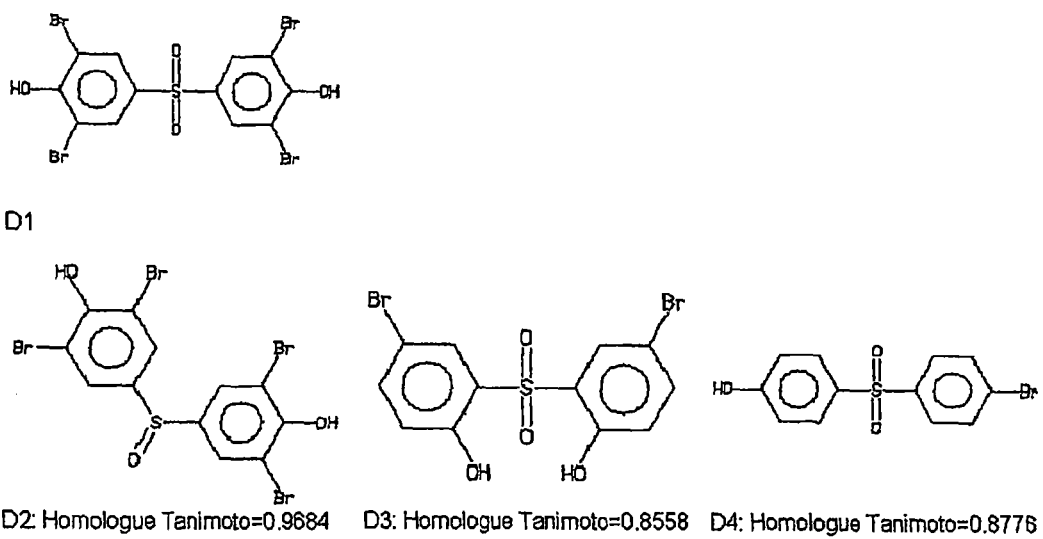
FIG. 4 depicts the structure of compound D1 and compounds D2-D4, which are homologues of D1.

In formula (IV) each of $R^{4A}$, $R^{4B}$, $R^{4C}$, $R^{4D}$, $R^{4E}$, and $R^{4F}$ is, independently, selected from H, halide, nitro, $C_{1-4}$ alkyl, $C_{2-4}$ alkenyl, $C_{2-4}$ alkynyl, $OR^{4G}$, $OC(O)R^{4H}$, $NR^{4I}R^{4J}$, $NHC(O)R^{4K}$, $NHC(S)R^{4L}$, $NHC(O)OR^{4M}$, $NHC(S)OR^{4N}$, $NHC(O)NHR^{4O}$, $NHC(S)NHR^{4P}$, $NHC(O)SR^{4Q}$, $NHC(S)SR^{4R}$, $NHS(O)_2R^{4S}$, $C(O)OR^{4T}$, and $C(O)NHR^{4U}$; $X^4$ is —S(O)— or —S(O)$_2$—; and each of $R^{4G}$, $R^{4H}$, $R^{4I}$, $R^{4J}$, $R^{4K}$, $R^{4L}$, $R^{4M}$, $R^{4N}, R^{4O}, R^{4P}, R^{4Q}, R^{4R}, R^{4S}, R^{4T},$ and $R^{4U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. Compounds of formula (IV) include compounds D1-D4 (see FIG. 4).

Compounds of formula (IV) can be synthesized using existing methodology. For example, a simple, unsymmetrical diaryl sulfones can be prepared from aryl boronic acids and arylsulfonyl chlorides (see Bandgar et al., Org. Lett., 6:2105-2108 (2004)) and from sulfinic acid salts and aryl halides or triflates (see Cacchi et al., J. Org. Chem. 69:5608-5614 (2004)). These approaches are depicted in Schemes 4a and 4b, respectively.

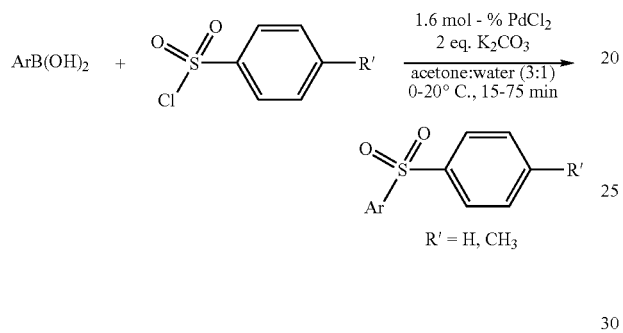

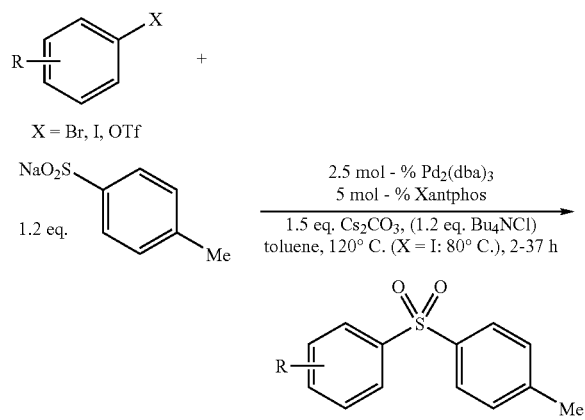

Sulfoxides of formula (IV) can be synthesized from their corresponding sulfide by hydrogen peroxide monooxidation (see, for example, Matteucci et al., Org. Lett., 5:235-237 (2003) and Scheme 4c, below).

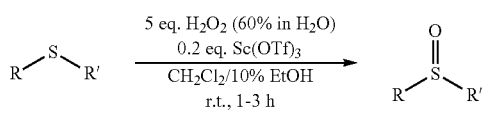

Compounds of Formula V

Compounds of the invention include compounds of formula (V).

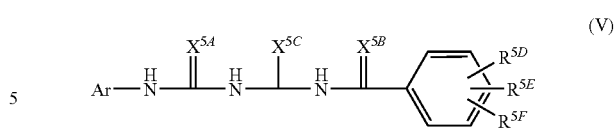

wherein Ar is described by any of formulas (Va), (Vb), or (Vc).

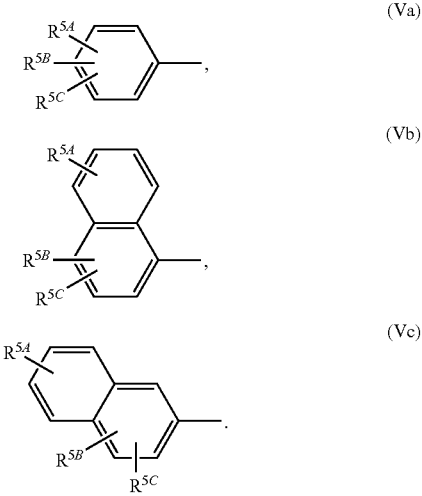

Figure 5A:
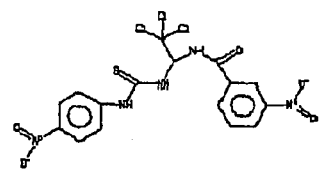
FIGS. 5A and 5B depict the structure of compound E1 and compounds E2-E25, which are homologues of E1.
Figure 5A:
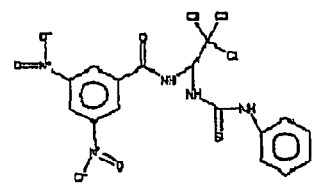
Figure 5A:
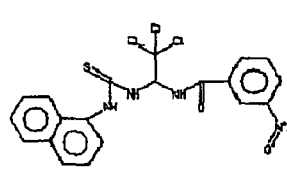
Figure 5A:
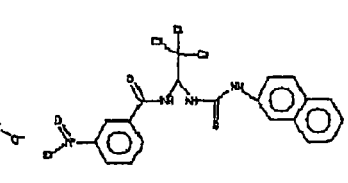
Figure 5A:
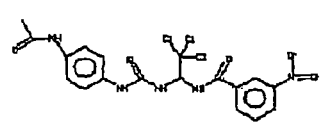
Figure 5A:
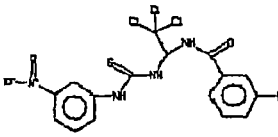
Figure 5A:
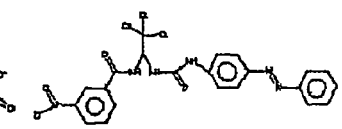
Figure 5A:
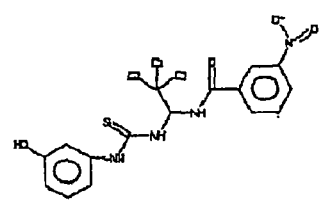
Figure 5A:
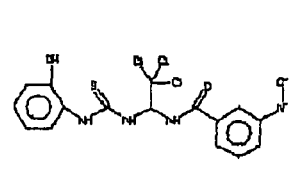
Figure 5A:
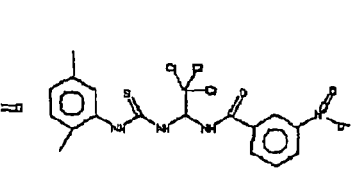
Figure 5A:
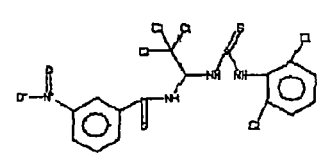
Figure 5A:
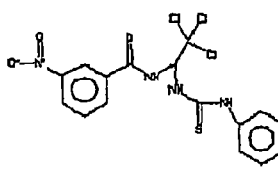
Figure 5A:
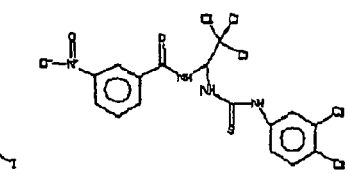
Figure 5B:
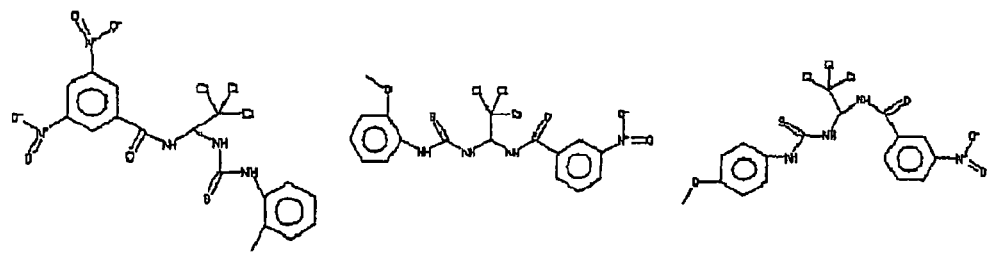
Figure 5B:
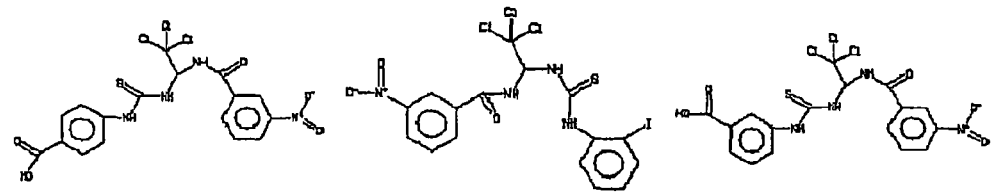
Figure 5B:
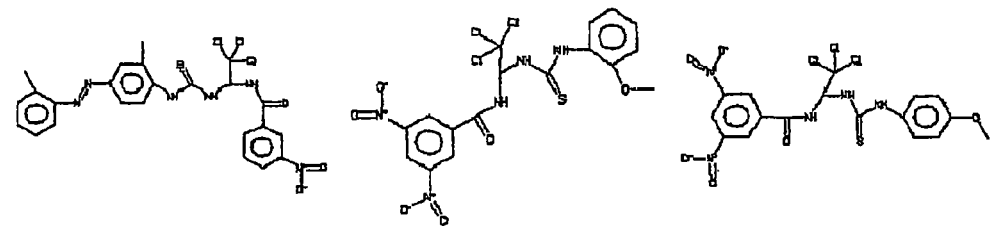
Figure 5B:
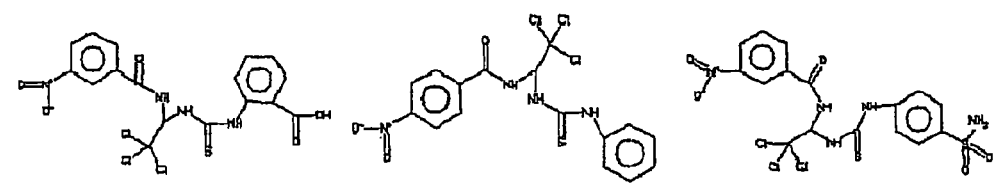
Figure 6A:
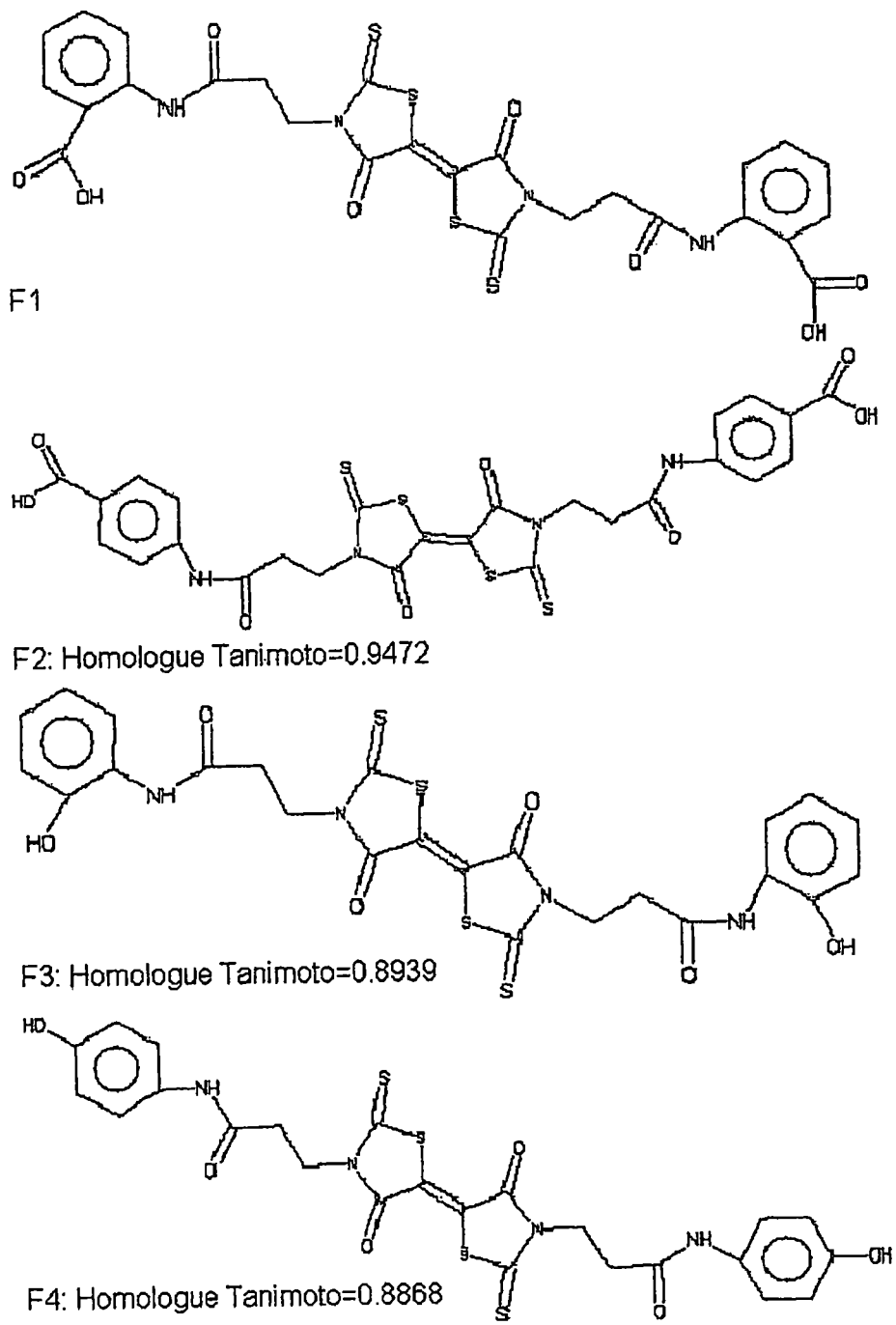
FIGS. 6A and 6B depict the structure of compound F1 and compounds F2-F7, which are homologues of F1.
Figure 6B:
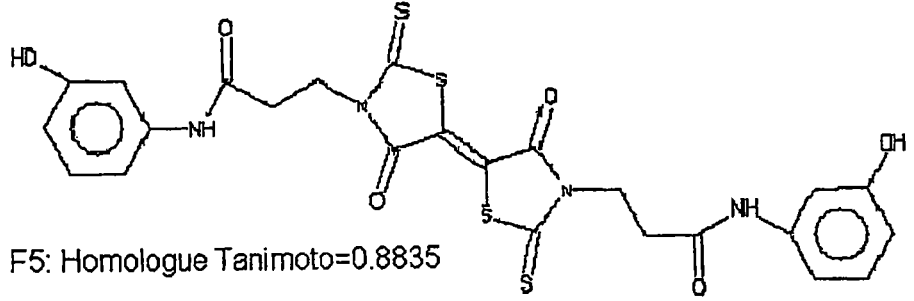
Figure 6B:
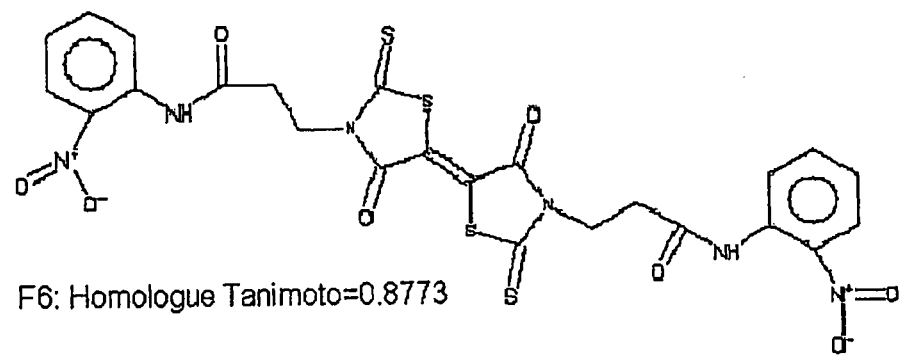
Figure 6B:
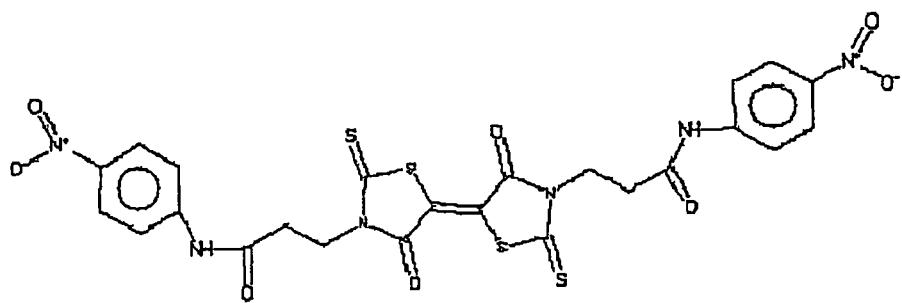

In formula (V), each of $R^{5A}, R^{5B}, R^{5C}, R^{5D}, R^{5E},$ and $R^{5F}$ is independently, selected from H, halide, nitro, $C_{1-4}$ alkyl, $C_{2-4}$ alkenyl, $C_{2-4}$ alkynyl, $OR^{5G}, OC(O)R^{5H}, NR^{5I}R^{5J}, NHC(O)R^{5K}, NHC(S)R^{5L}, NHC(O)OR^{5M}, NHC(S)OR^{5N}, NHC(O)NHR^{5O}, NHC(S)NHR^{5P}, NHC(O)SR^{5Q}, NHC(S)SR^{5R}, NHS(O)_2R^{5S}, C(O)OR^{5T},$ and $C(O)NHR^{5U}$; each of $X^{5A}$ and $X^{5B}$ is, independently, selected from O and S; $X^{5C}$ is selected from $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl; and each of $R^{5G}, R^{5H}, R^{5I}, R^{5J}, R^{5K}, R^{5L}, R^{5M}, R^{5N}, R^{5O}, R^{5P}, R^{5Q}, R^{5R}, R^{5S}, R^{5T},$ and $R^{5U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. Compounds of formula (V) include compounds E1-E25 (see FIGS. 5A and 5B) and compound E30 (see FIG. 15).

Compounds of formula (V) can be synthesized using the approach outlined in Scheme 5 for compound E1. Substituted arylureas and arylthioureas can be employed (e.g., to produce compounds described by formulas Va-Vc and to produce compounds in which $X^{5A}$ is O or S). The synthesis can be completed by amide coupling with any desired benzoic acid derivative.

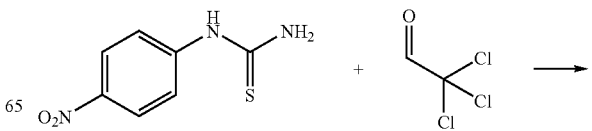

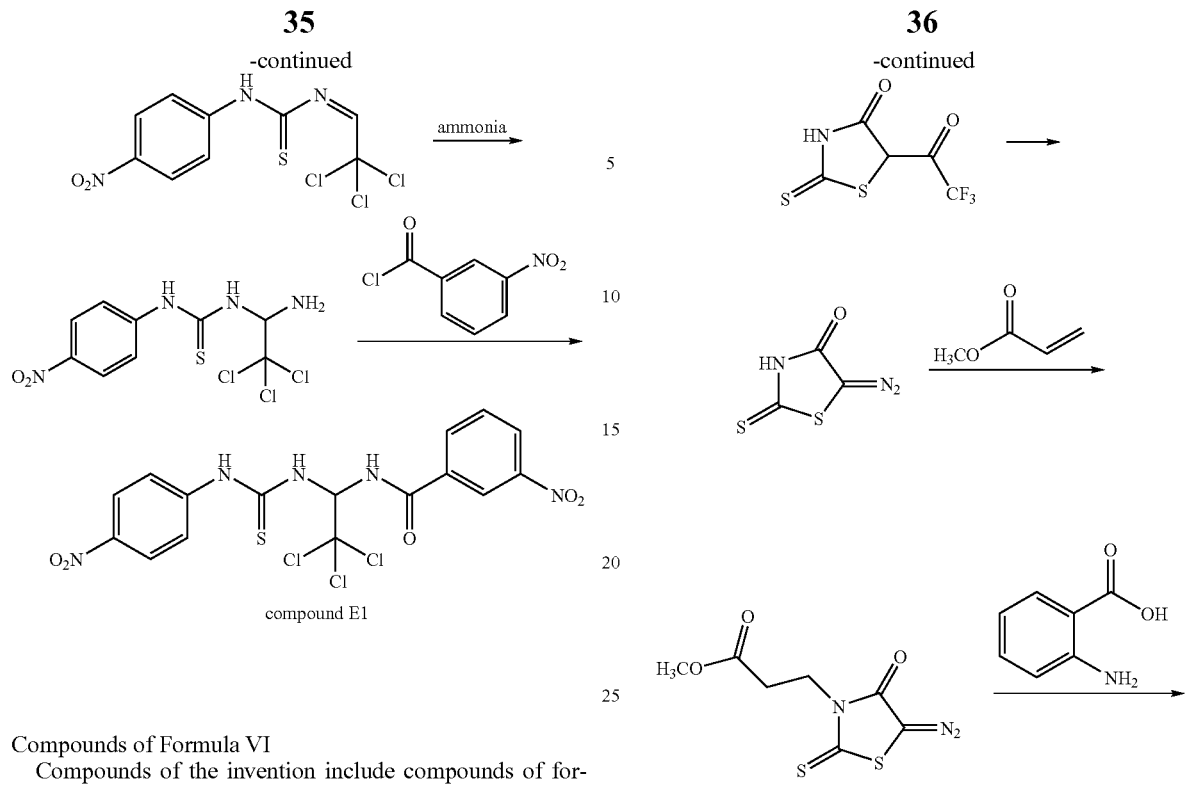

compound E1

Compounds of Formula VI

Compounds of the invention include compounds of formula (VI).

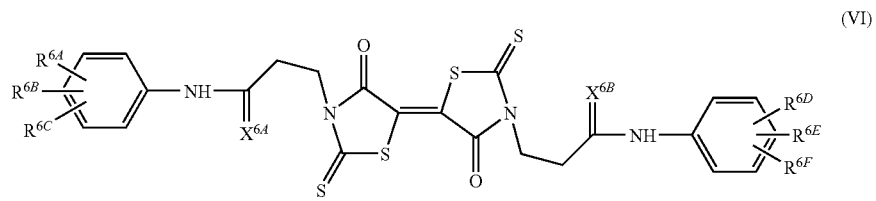

(VI)

In formula (VI), each of $R^{6A}$, $R^{6B}$, $R^{6C}$, $R^{6D}$, $R^{6E}$, and $R^{6F}$ is selected, independently, from H, halide, nitro, $C_{1-4}$ alkyl, $C_{2-4}$ alkenyl, $C_{2-4}$ alkynyl, $OR^{6G}$, $OC(O)R^{6H}$, $NR^{6I}R^{6J}$, $NHC(O)R^{6K}$, $NHC(S)R^{6L}$, $NHC(O)OR^{6M}$, $NHC(S)OR^{6N}$, $NHC(O)NHR^{6O}$, $NHC(S)NHR^{6P}$, $NHC(O)SR^{6Q}$, $NHC(S)SR^{6R}$, $NHS(O)_2R^{6S}$, $C(O)OR^{6T}$, and $C(O)NHR^{6U}$; each of $X^{6A}$ and $X^{6B}$ is, independently, selected from O and S; and each of $R^{6G}$, $R^{6H}$, $R^{6I}$, $R^{6J}$, $R^{6K}$, $R^{6L}$, $R^{6M}$, $R^{6N}$, $R^{6O}$, $R^{6P}$, $R^{6Q}$, $R^{6R}$, $R^{6S}$, $R^{6T}$, and $R^{6U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. Compounds of formula (VI) include compounds F1-F7 (see FIG. 6).

Compounds of formula (VI) can be synthesized using the approach outlined in Scheme 5 for compound F1.

Scheme 6

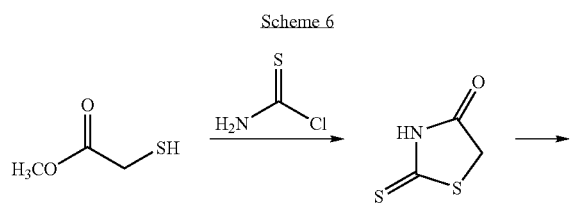

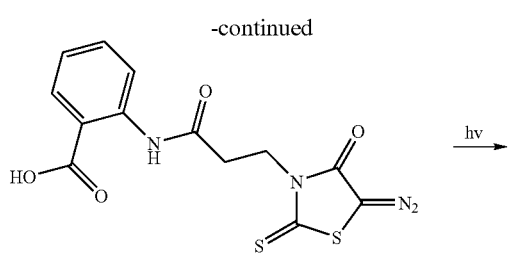

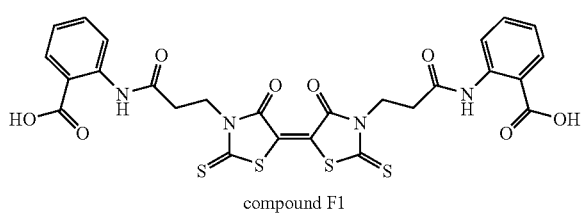

compound F1

Compounds of Formula VII

Compounds of the invention include compounds of formula (VII).

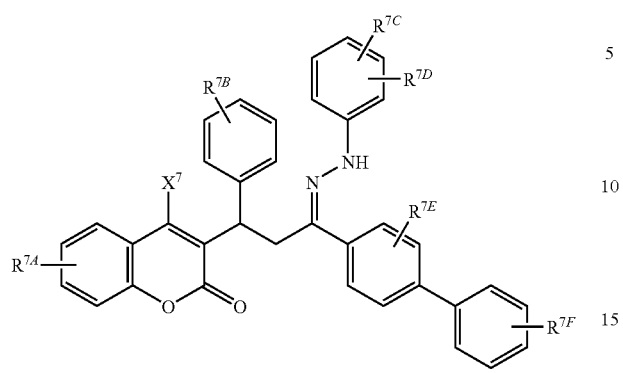

(VII)

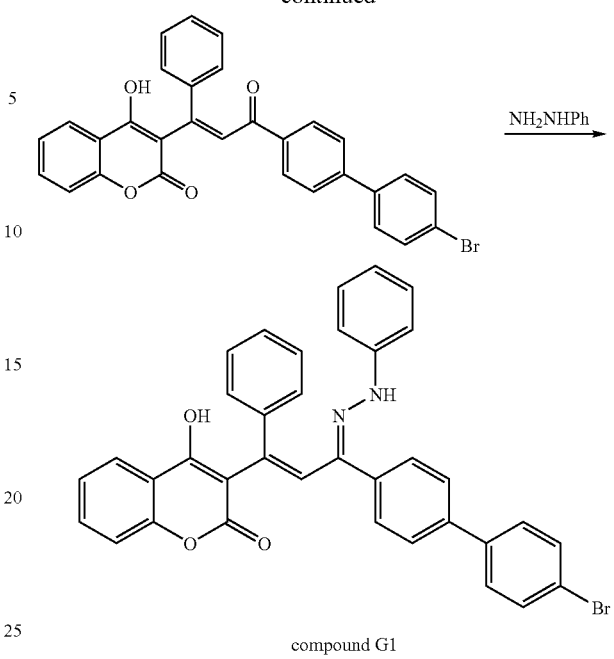

compound G1

Compounds of Formula VIII

Compounds of the invention include compounds of formula (VIII).

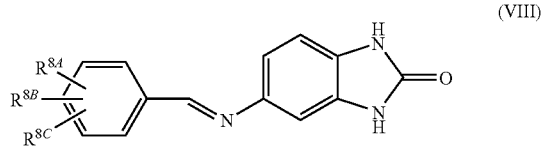

(VIII)

Figure 7:
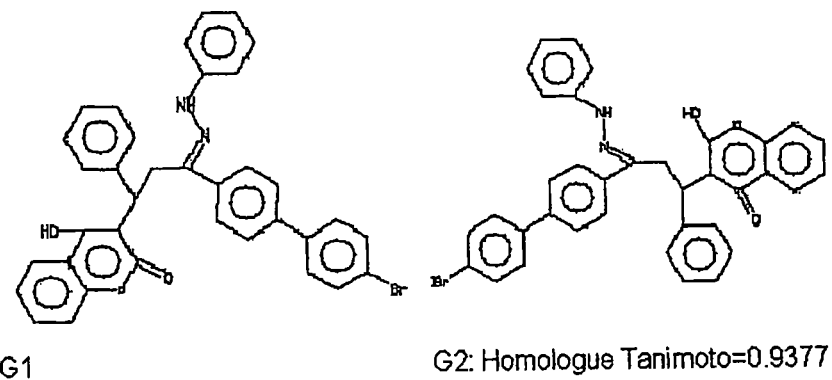
FIG. 7 depicts the structure of compound G1 and compound G2, which is a homologue of G1.

In formula (VII), each of $R^{7A}$, $R^{7B}$, $R^{7C}$, $R^{7D}$, $R^{7E}$, and $R^{7F}$ is, independently, selected from H, halide, nitro, $C_{1-4}$ alkyl, $C_{2-4}$ alkenyl, $C_{2-4}$ alkynyl, $OR^{7G}$, $OC(O)R^{7H}$, $NR^{7I}R^{7J}$, $NHC(O)R^{7K}$, $NHC(S)R^{7L}$, $NHC(O)OR^{7M}$, $NHC(S)OR^{7N}$, $NHC(O)NHR^{7O}$, $NHC(S)NHR^{7P}$, $NHC(O)SR^{7Q}$, $NHC(S)SR^{7R}$, $NHS(O)_2R^{7S}$, $C(O)OR^{7T}$, and $C(O)NHR^{7U}$; $X^7$ is independently selected from $OR^{7G}$, $OC(O)R^{7H}$, $NR^{7I}R^{7J}$, $NHC(O)R^{7K}$, $NHC(S)R^{7L}$, $NHC(O)OR^{7M}$, $NHC(S)OR^{7N}$, $NHC(O)NHR^{7O}$, $NHC(S)NHR^{7P}$, $NHC(O)SR^{7Q}$, $NHC(S)SR^{7R}$, and $NHS(O)_2R^{7S}$; and each of $R^{7G}$, $R^{7H}$, $R^{7I}$, $R^{7J}$, $R^{7K}$, $R^{7L}$, $R^{7M}$, $R^{7N}$, $R^{7O}$, $R^{7P}$, $R^{7Q}$, $R^{7R}$, $R^{7S}$, $R^{7T}$, and $R^{7U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. Compounds of formula (VII) include compounds G1 and G2 (see FIG. 7).

Compounds of formula (VII) can be synthesized using the approach outlined in Scheme 7 for compound G1.

Scheme 7

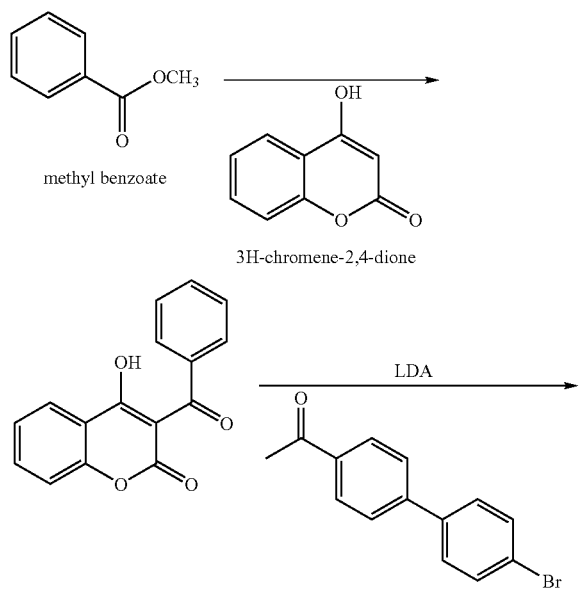

methyl benzoate 3H-chromene-2,4-dione

Figure 8:
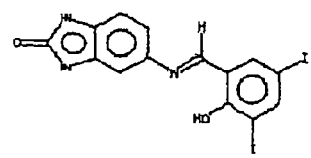
FIG. 8 depicts the structure of compound H1 and compounds H2-H8, which are homologues of H1.
Figure 8:
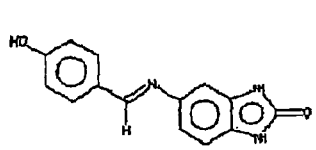
Figure 8:
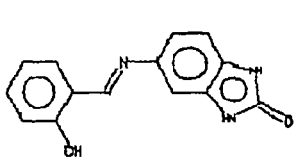
Figure 8:
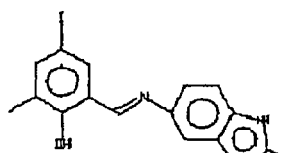
Figure 8:
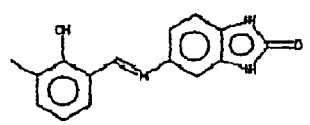
Figure 8:
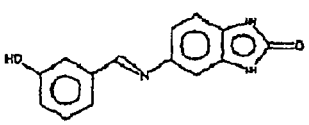
Figure 8:
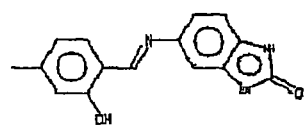
Figure 8:
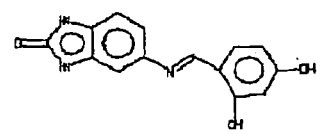

In formula (VIII), each of $R^{8A}$, $R^{8B}$, and $R^{8C}$ is, independently, selected from H, halide, nitro, $C_{1-4}$ alkyl, $C_{2-4}$ alkenyl, $C_{2-4}$ alkynyl, $OR^{8G}$, $OC(O)R^{8H}$, $NR^{8I}R^{8J}$, $NHC(O)R^{8K}$, $NHC(S)R^{8L}$, $NHC(O)OR^{8M}$, $NHC(S)OR^{8N}$, $NHC(O)NHR^{8O}$, $NHC(S)NHR^{8P}$, $NHC(O)SR^{8Q}$, $NHC(S)SR^{8R}$, $NHS(O)_2R^{8S}$, $C(O)OR^{8T}$, and $C(O)NHR^{8U}$; and each of $R^{8G}$, $R^{8H}$, $R^{8I}$, $R^{8J}$, $R^{8K}$, $R^{8L}$, $R^{8M}$, $R^{8N}$, $R^{8O}$, $R^{8P}$, $R^{8Q}$, $R^{8R}$, $R^{8S}$, $R^{8T}$, and $R^{8U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. Compounds of formula (VIII) include compounds H1-H8 (see FIG. 8).

Compounds of formula (VIII) can by prepared by condensation of 5-amino-2-benzimidazolinone (aka 5-Amino-2-hydroxybenzimidazole, CAS 95-23-8; Pfaltz & Bauer Cat. No. A17950) with a benzaldehyde derivative (see Scheme 8a). Compound H1 can be prepared as described in Scheme 8b.

Scheme 8a

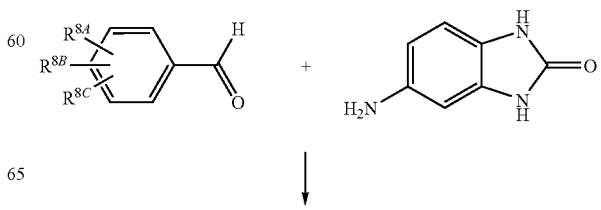

-continued

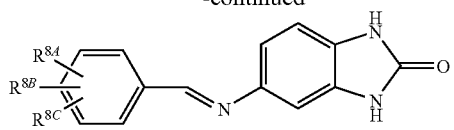

Scheme 8b

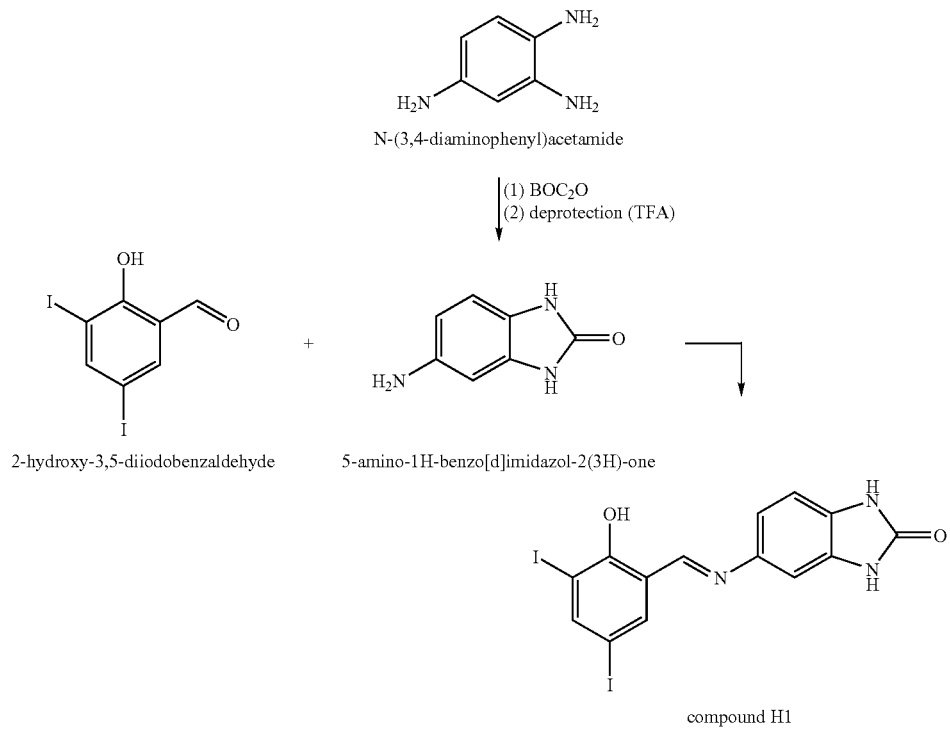

compound H1

Compounds of Formula IX

Compounds of the invention include compounds of formula (IX).

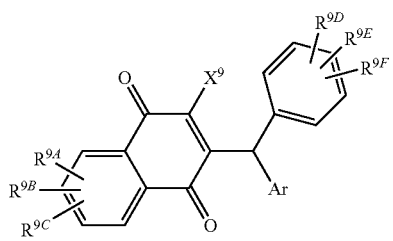
(IX)

Figure 9:
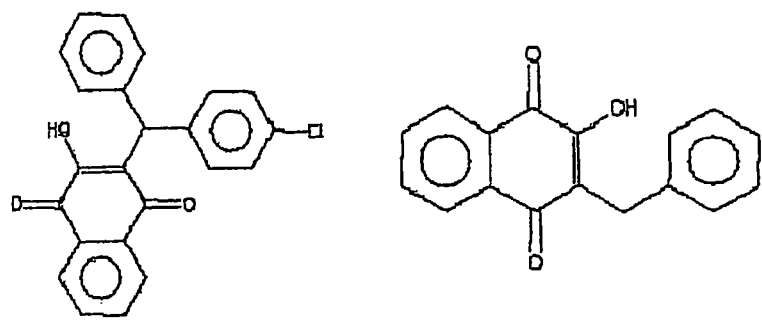
FIG. 9 depicts the structure of compound I1 and compound I2, which is a homologue of I1.

In formula (IX), each of $R^{9A}$, $R^{9B}$, $R^{9C}$, $R^{9D}$, $R^{9E}$, and $R^{9F}$ is independently, selected from H, halide, nitro, $C_{1-4}$ alkyl, $C_{2-4}$ alkenyl, $C_{2-4}$ alkynyl, $OR^{9G}$, $OC(O)R^{9H}$, $NR^{9I}R^{9J}$, $NHC(O)R^{9K}$, $NHC(S)R^{9L}$, $NHC(O)OR^{9M}$, $NHC(S)OR^{9N}$, $NHC(O)NHR^{9O}$, $NHC(S)NHR^{9P}$, $NHC(O)SR^{9Q}$, $NHC(S)SR^{9R}$, $NHS(O)_2R^{9S}$, $C(O)OR^{9T}$, and $C(O)NHR^{9U}$; $X^9$ is independently selected from $OR^{9G}$, $OC(O)R^{9H}$, $NR^{9I}R^{9J}$, $NHC(O)R^{9K}$, $NHC(S)R^{9L}$, $NHC(O)OR^{9M}$, $NHC(S)OR^{9N}$, $NHC(O)NHR^{9O}$, $NHC(S)NHR^{9P}$, $NHC(O)SR^{9Q}$, $NHC(S)SR^{9R}$, and $NHS(O)_2R^{9S}$; Ar is selected from $C_{2-6}$ heterocyclyl and $C_{6-12}$ aryl; and each of $R^{9G}$, $R^{9H}$, $R^{9I}$, $R^{9J}$, $R^{9K}$, $R^{9L}$, $R^{9M}$, $R^{9N}$, $R^{9O}$, $R^{9P}$, $R^{9Q}$, $R^{9R}$, $R^{9S}$, $R^{9T}$, and $R^{9U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. Compounds of formula (IX) include compounds I1 and I2 (see FIG. 9).

Compounds of formula (IX) can be prepared by boiling 2-Hydroxy-1,4-naphthoquinone (Aldrich Cat. No. H46805) in sulfuric acid with alcohols of the formula Aryl-CH(OH)-Aryl' as described by Zalukaev et al., Voronezh. Gos. Univ., Voronezh, USSR. Izvestiya Vysshikh Uchebnykh Zavedenii, Khimiya i Khimicheskaya Tekhnologiya 16:1599-600 (1973).

Compounds of Formula X

Compounds of the invention include compounds of formula (X).

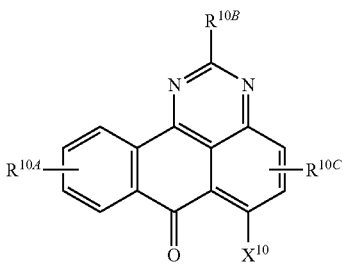
(X)

Figure 10:
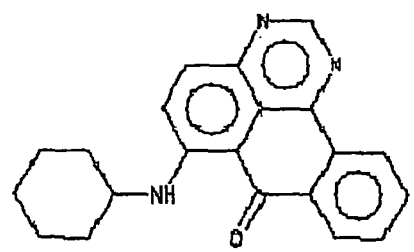
FIG. 10 depicts the structure of compound J1 and compounds J2-J6, which are homologues of J1.
Figure 10:
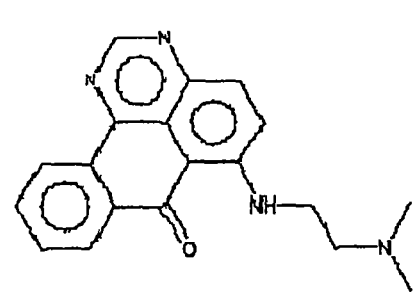
Figure 10:
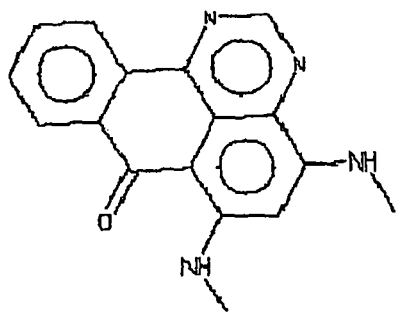
Figure 10:
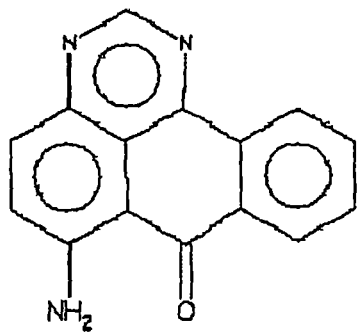
Figure 10:
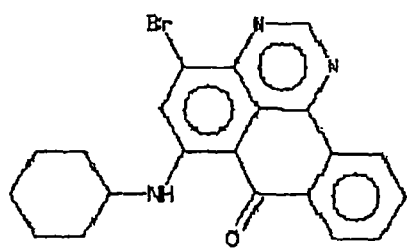
Figure 10:
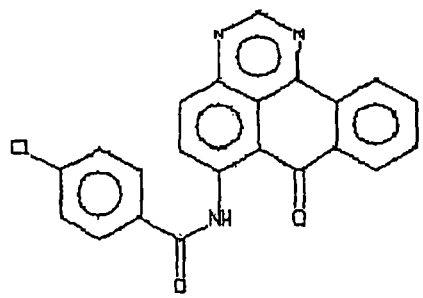
Figure 11:
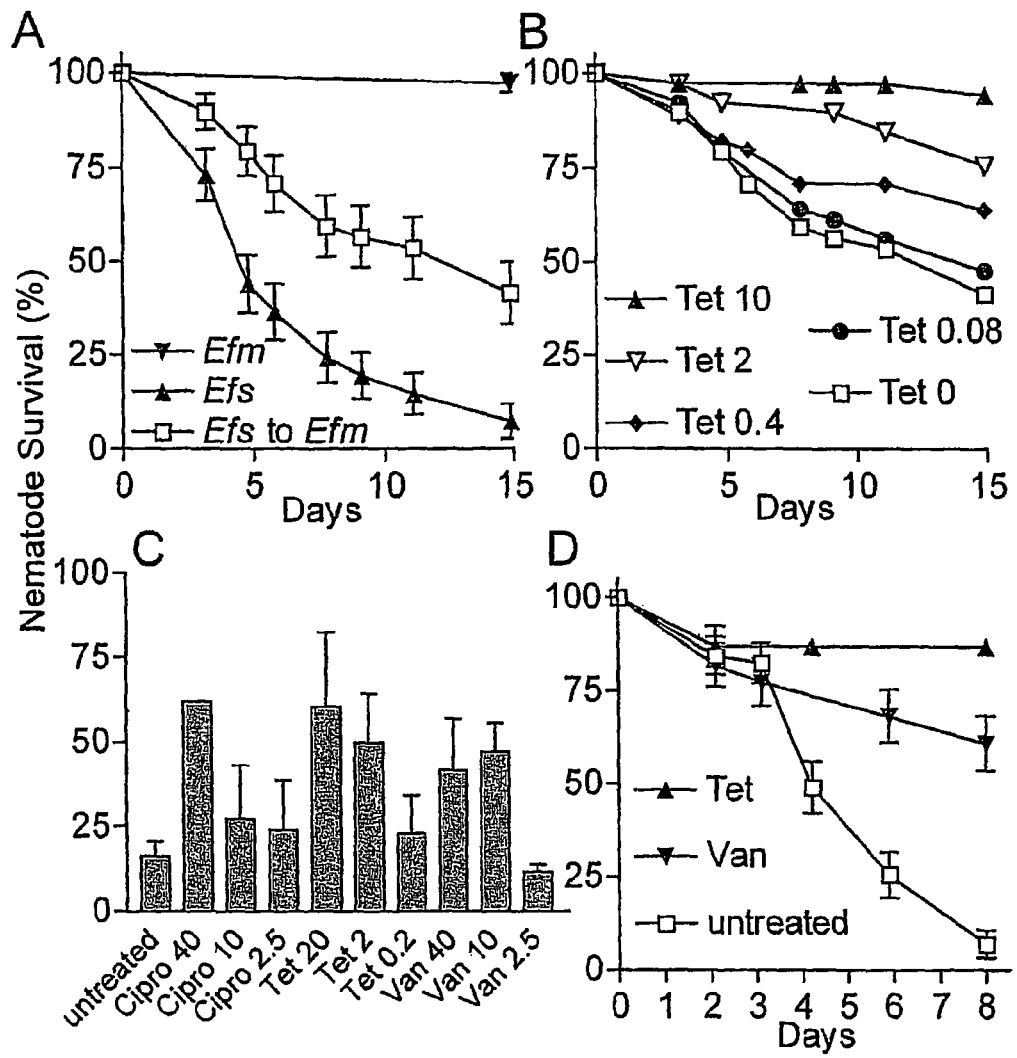
FIGS. 11A-11D show the curing of a nematode *E. faecalis* infection on solid medium by antibiotic treatment.
Figure 12:
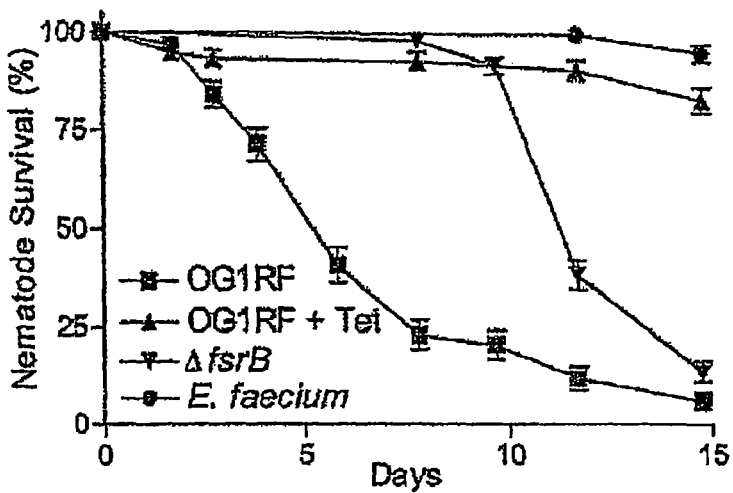
FIGS. 12A-12C show the liquid infection assay gauges differences in nematode killing due to *E. faecalis* strains with varying degrees of pathogenicity or due to antibiotic treatment.
Figure 12:
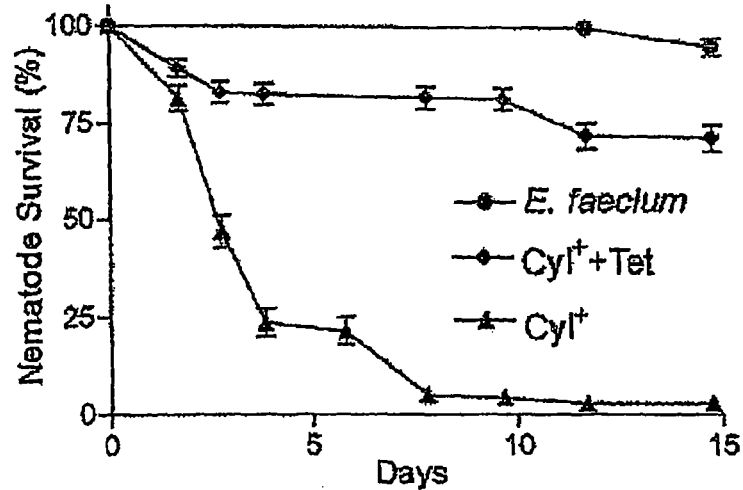
Figure 12:
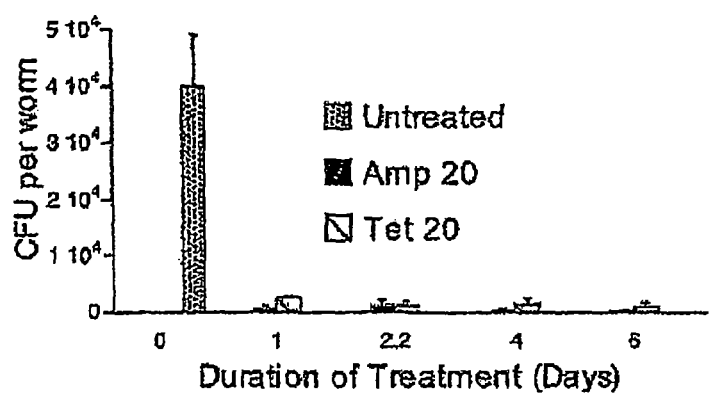
Figure 13:
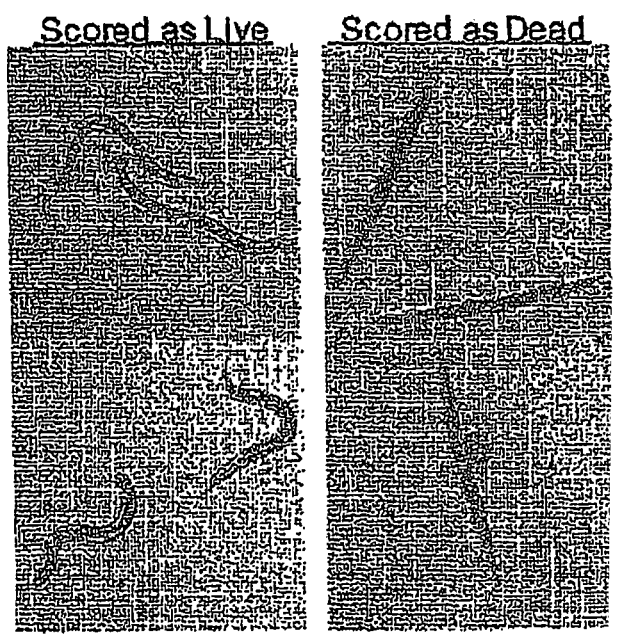
FIG. 13 is a series of pictures depicting the scoring live/dead worms in the liquid killing assay. Living nematodes in the liquid infection assay maintain a sinusoidal shape, whereas dead nematodes in the liquid infection assay appear as straight, rigid rods as the corpse becomes filled with bacteria.
Figure 14:
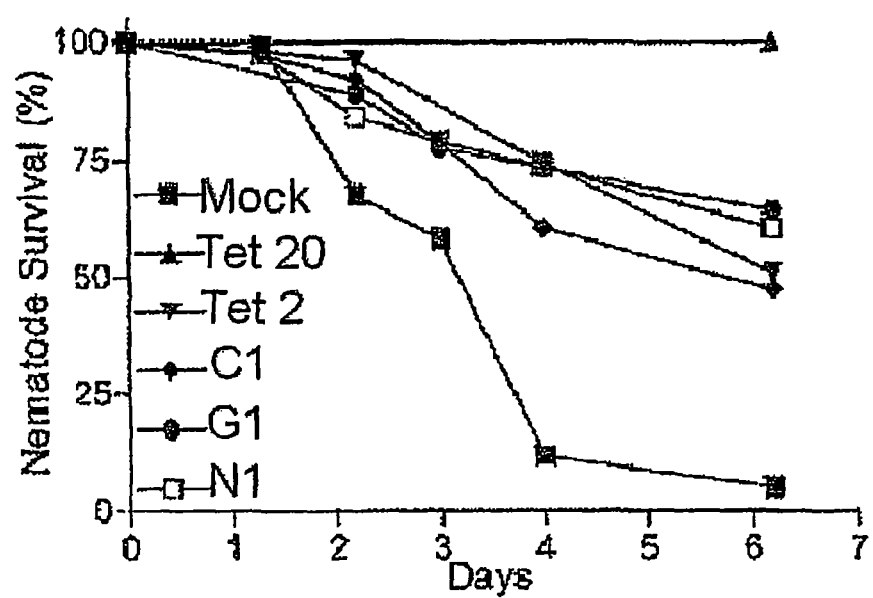
FIG. 14 is a graph depicting the curing kinetics of selected hit compounds. The Kaplan-Meier survival curves of infected nematodes treated with 25 μg/ml of compound C1 (♦), 50 μg/ml of compound G1 (●), 25 μg/ml of compound N1 (□), 2 μg/ml tetracycline (▼), 20 μg/ml tetracycline (▲), or mock treatment (■). In pairwise comparisons to mock treatment using log-rank tests, the difference for all of the treatments was significant with p<0.0001.
Figure 15A:
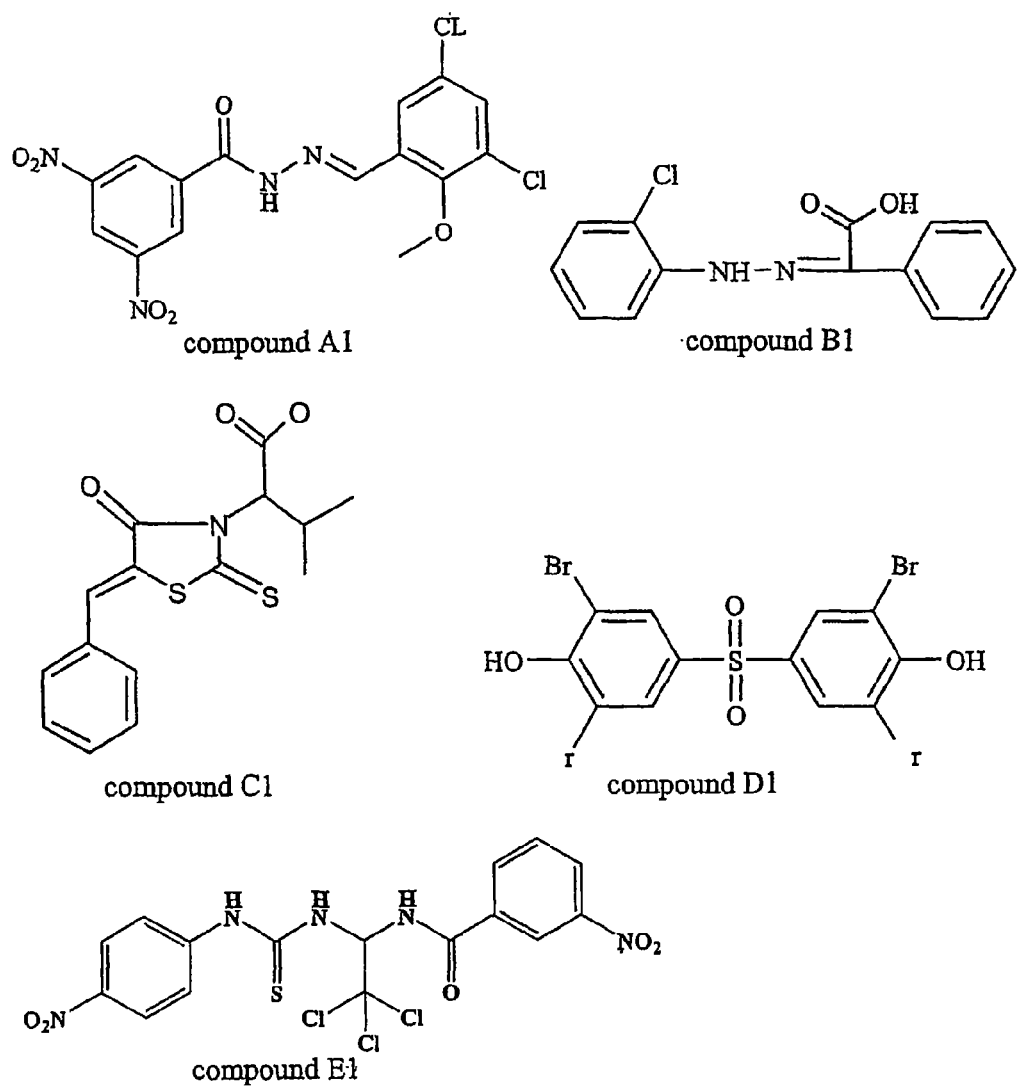
FIGS. 15A-15C show the structures of the lead compounds A1, B1, C1, D1, E1, E30, F1, G1, H1, I1, J1, K1, L1, M1, N1, and O1.
Figure 15B:
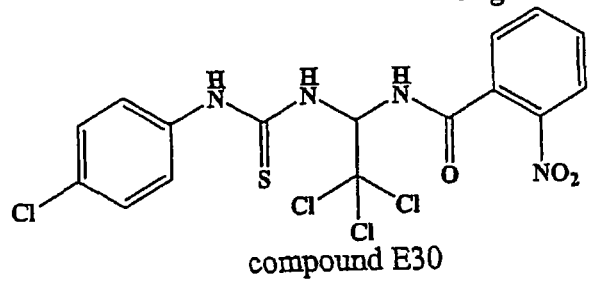
Figure 15B:
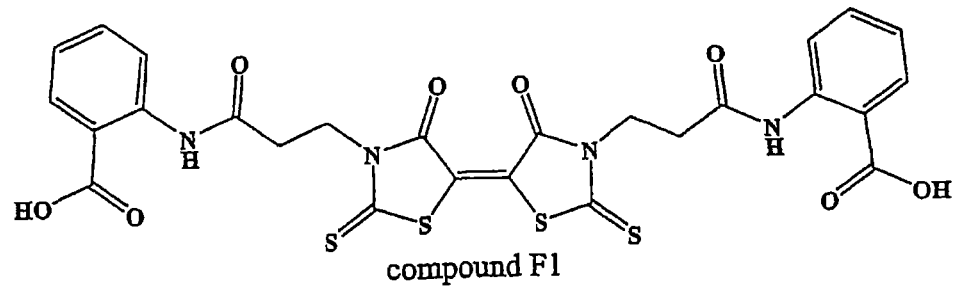
Figure 15B:
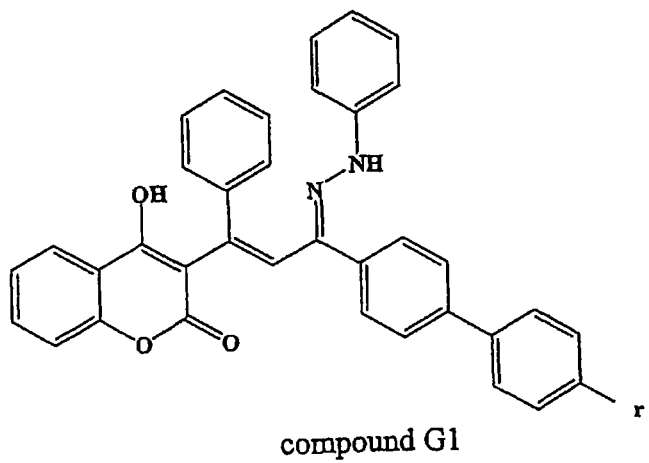
Figure 15B:
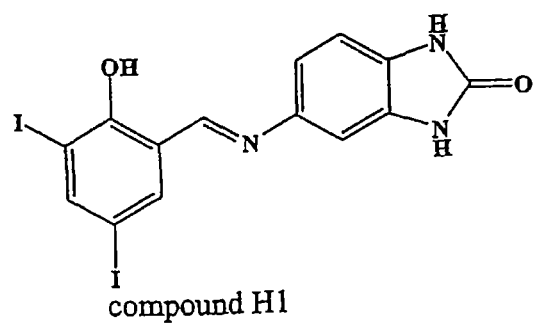
Figure 15B:
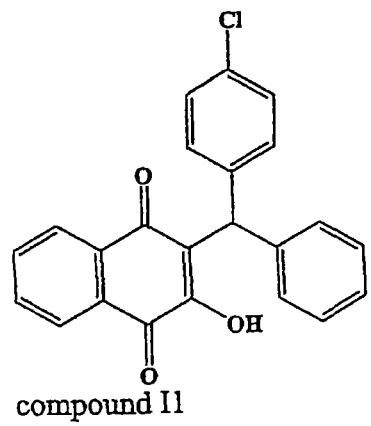
Figure 15C:
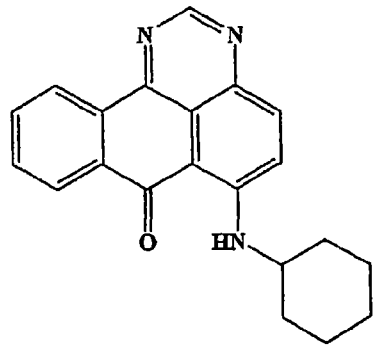
Figure 15C:
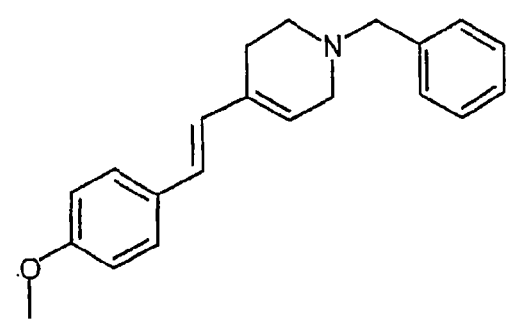
Figure 15C:
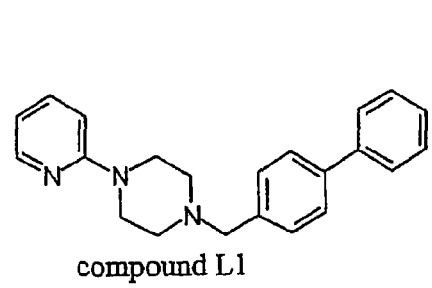
Figure 15C:
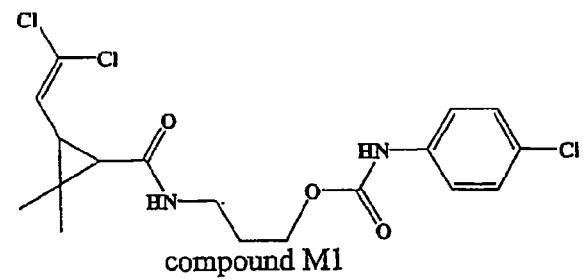
Figure 15C:
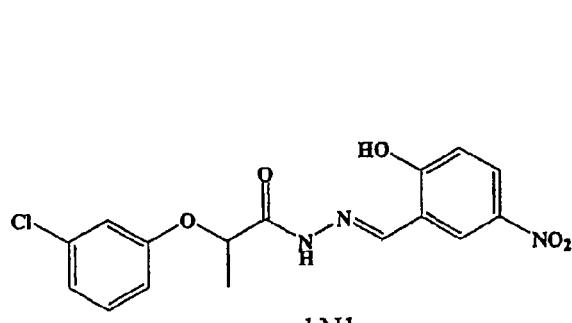
Figure 15C:
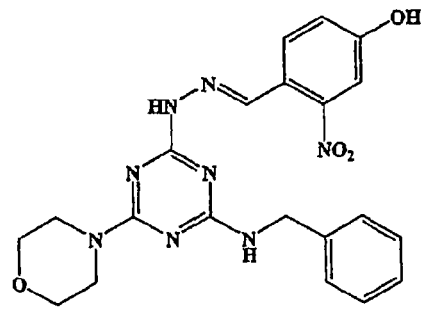

In formula (X), each of $R^{10A}$, $R^{10B}$, and $R^{10C}$ is, independently, selected from H, halide, nitro, $C_{1-4}$ alkyl, $C_{2-4}$ alkenyl, $C_{2-4}$ alkynyl, $OR^{10G}$, $OC(O)R^{10H}$, $NR^{10I}R^{10J}$, $NHC(O)R^{10K}$, $NHC(S)R^{10L}$, $NHC(O)OR^{10M}$, $NHC(S)OR^{10N}$, $NHC(O)NHR^{10O}$, $NHC(S)NHR^{10P}$, $NHC(O)SR^{10Q}$, $NHC(S)SR^{10R}$, $NHS(O)_2R^{10S}$, $C(O)OR^{10T}$, and $C(O)NHR^{10U}$; $X^{10}$ is independently selected from $OR^{10G}$, $OC(O)R^{10H}$, $NR^{10I}R^{10J}$, NHC(O)$R^{10K}$, NHC(S)$R^{10L}$, NHC(O)O$R^{10M}$, NHC(S) O$R^{10N}$, NHC(O)NH$R^{10O}$, NHC(S)NH$R^{10P}$, NHC(O)S$R^{10Q}$, NHC(S)S$R^{10R}$, and NHS(O)$_2R^{10S}$; and each of $R^{10G}$, $R^{10H}$, $R^{10I}$, $R^{10J}$, $R^{10K}$, $R^{10L}$, $R^{10M}$, $R^{10N}$, $R^{10O}$, $R^{10P}$, $R^{10Q}$, $R^{10R}$, $R^{10S}$, $R^{10T}$, and $R^{10U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. Compounds of formula (X) include compounds J1-J6 (see FIG. 10).

Compounds of formula (X) can be synthesized using the approach outlined in Scheme 10 for compound J1.

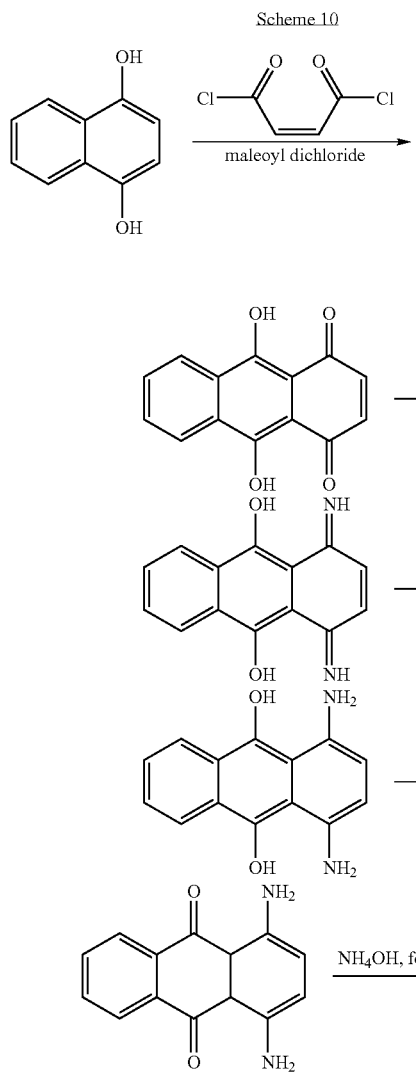

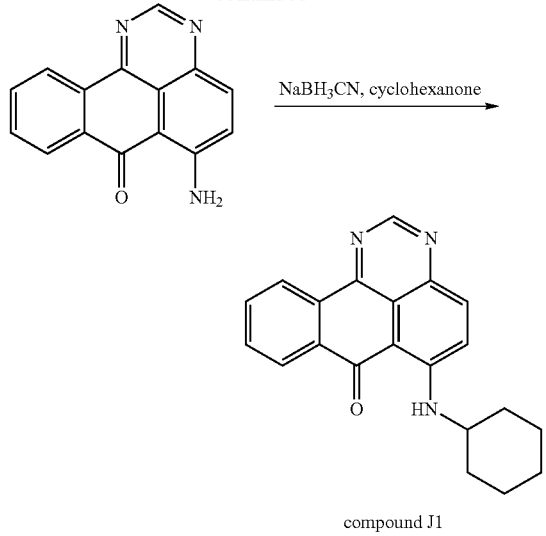

compound J1

Compounds of Formula XI

Compounds of the invention include compounds of formula (XI).

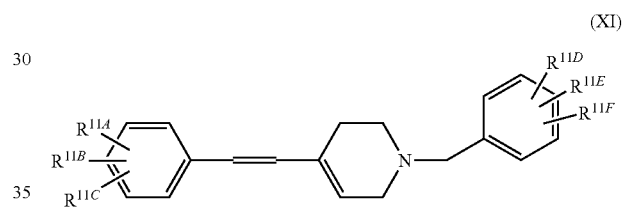

(XI)

In formula (XI), each of $R^{11A}$, $R^{11B}$, $R^{11C}$, $R^{11D}$, $R^{11E}$, and $R^{11F}$ is, independently, selected from H, halide, nitro, $C_{1-4}$ alkyl, $C_{2-4}$ alkenyl, $C_{2-4}$ alkynyl, O$R^{11G}$, OC(O)$R^{11H}$, N$R^{11I}R^{11J}$, NHC(O)$R^{11K}$, NHC(S)$R^{11L}$, NHC(O)O$R^{11M}$, NHC(S)O$R^{11N}$, NHC(O)NH$R^{11O}$, NHC(S)NH$R^{11P}$, NHC(O)S$R^{11Q}$, NHC(S)S$R^{11R}$, NHS(O)$_2R^{11S}$, C(O)O$R^{11T}$, and C(O)NH$R^{11U}$; and each of $R^{11G}$, $R^{11H}$, $R^{11J}$, $R^{11K}$, $R^{11L}$, $R^{11M}$, $R^{11N}$, $R^{11O}$, $R^{11P}$, $R^{11Q}$, $R^{11R}$, $R^{11S}$, $R^{11T}$, and $R^{11U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. Formula (XI) includes compound K1 (see FIG. 15).

Compounds of formula (XI) can be synthesized using the approach outlined in Scheme 11 for compound K1.

Scheme 11

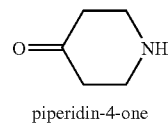

piperidin-4-one

↓ BnBr

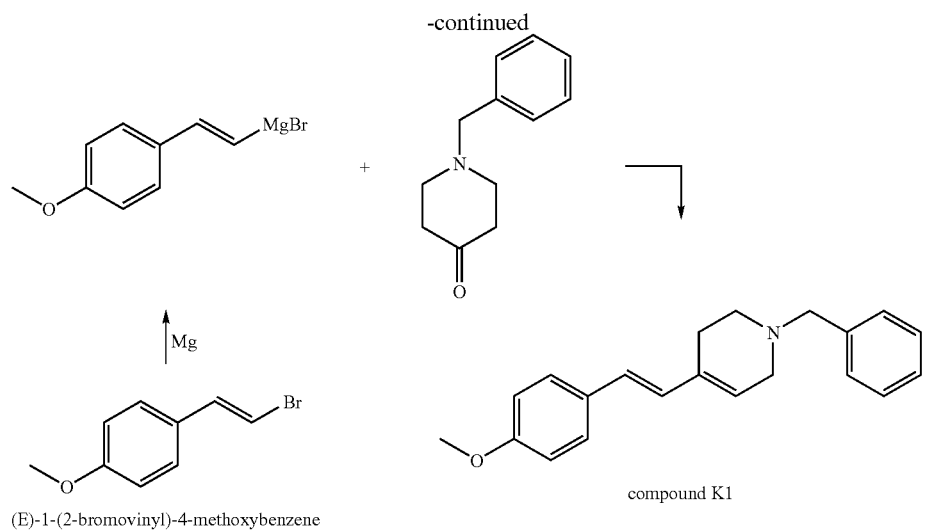

(E)-1-(2-bromovinyl)-4-methoxybenzene compound K1

Compounds of Formula XII

Compounds of the invention include compounds of formula (XII).

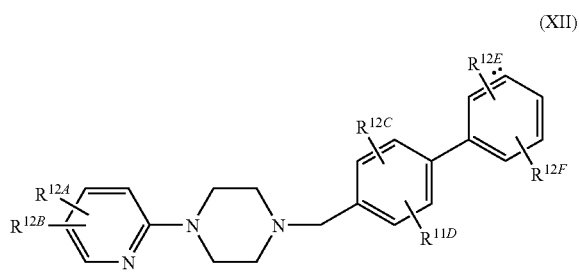

(XII)

In formula (XII), each of $R^{12A}$, $R^{12B}$, $R^{12C}$, $R^{12D}$, $R^{12E}$, and $R^{12F}$ is, independently, selected from H, halide, nitro, $C_{1-4}$ alkyl, $C_{2-4}$ alkenyl, $C_{2-4}$ alkynyl, $OR^{12G}$, $OC(O)R^{12H}$, $NR^{12I}R^{12J}$, $NHC(O)R^{12K}$, $NHC(S)R^{12L}$, $NHC(O)OR^{12M}$, $NHC(S)OR^{12N}$, $NHC(O)NHR^{12O}$, $NHC(S)NHR^{12P}$, $NHC(O)SR^{12Q}$, $NHC(S)SR^{12R}$, $NHS(O)_2R^{12S}$, $C(O)OR^{12T}$, and $C(O)NHR^{12U}$; and each of $R^{12G}$, $R^{12H}$, $R^{12I}$, $R^{12J}$, $R^{12K}$, $R^{12L}$, $R^{12M}$, $R^{12N}$, $R^{12O}$, $R^{12P}$, $R^{12Q}$, $R^{12R}$, $R^{12S}$, $R^{12T}$, and $R^{12U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. Formula (XII) includes compound L1 (see FIG. 15).

Compounds of formula (XII) can by prepared by the sequential alkylation of piperazine (see Scheme 12a below, X is a leaving group (e.g., a halide) and P is a protecting group). Compound L1 can be synthesized as described in Scheme 12b.

Scheme 12a

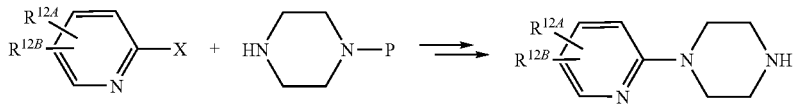

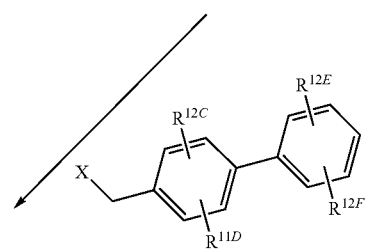

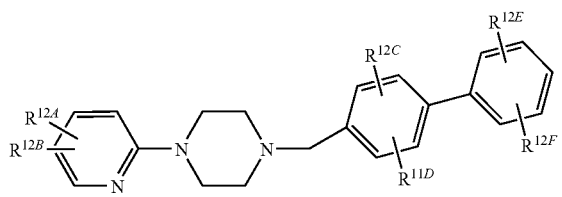

Scheme 12b

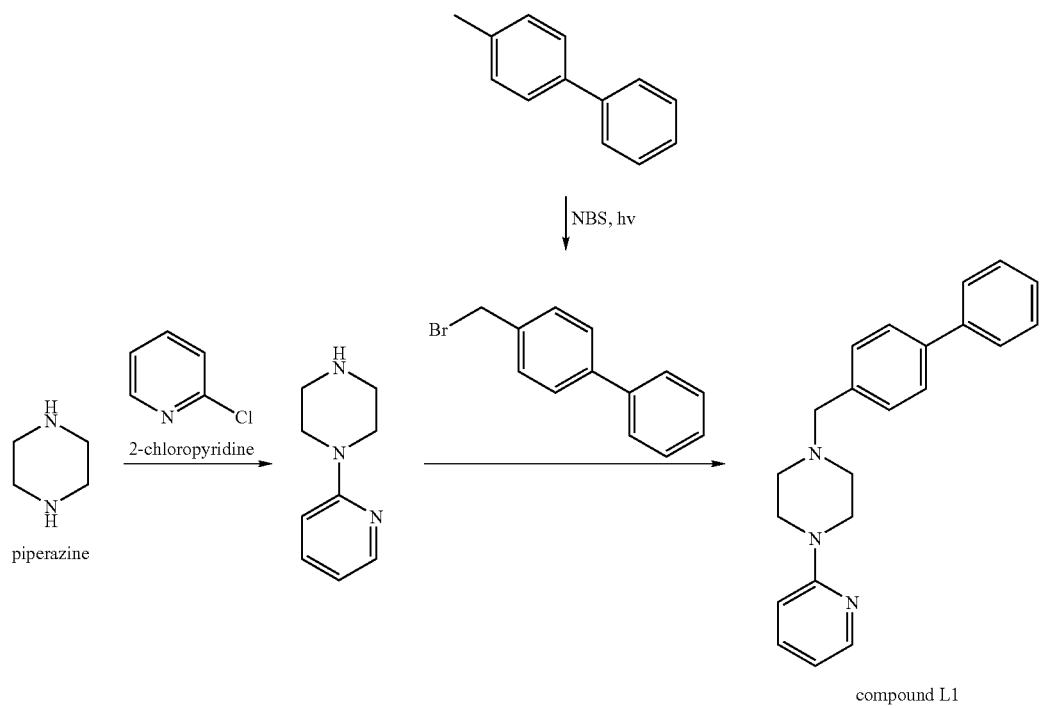

compound L1

Alternatively, piperazines of formula (XII) can be prepared by condensation of piperazine, or a derivative thereof, with the desired biphenyl aldehyde, followed by reduction of the resulting imine as described by Forsee et al., J. Am. Chem. Soc. 57:1788 (1935).

Compounds of Formula XIII

Compounds of the invention include compounds of formula (XIII).

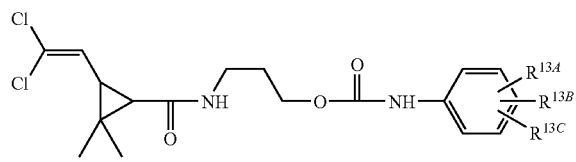

(XIII)

In formula (XIII), each of $R^{13A}$, $R^{13B}$, and $R^{13C}$ is, independently, selected from H, halide, nitro, $C_{1-4}$ alkyl, $C_{2-4}$ alkenyl, $C_{2-4}$ alkynyl, $OR^{13G}$, $OC(O)R^{13H}$, $NR^{13I}R^{13J}$, $NHC(O)R^{13K}$, $NHC(S)R^{13L}$, $NHC(O)OR^{13M}$, $NHC(S)OR^{13N}$, $NHC(O)NHR^{13O}$, $NHC(S)NHR^{13P}$, $NHC(O)SR^{13Q}$, $NHC(S)SR^{13R}$, $NHS(O)_2R^{13S}$, $C(O)OR^{13T}$, and $C(O)NHR^{13U}$; and each of $R^{13G}$, $R^{13H}$, $R^{13I}$, $R^{13J}$, $R^{13K}$, $R^{13L}$, $R^{13M}$, $R^{13N}$, $R^{13O}$, $R^{13P}$, $R^{13Q}$, $R^{13R}$, $R^{13S}$, $R^{13T}$, and $R^{13U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. Formula (XIII) includes compound M1 (see FIG. 15).

Compounds of formula (XIII) can by prepared by activation of 3-(2,2-dichlorovinyl)-2,2-dimethylcyclopropane carboxylic acid (CAS 55701-05-8) and reaction with 3-amino-1-propanol (Aldrich Cat. No. 23, 984-4), followed by reaction with the appropriately substituted phenyl isocyanate to form the carbamate of formula (XII) (see Scheme 13a). Compound M1 can be prepared as described in Scheme 13b.

Scheme 13a

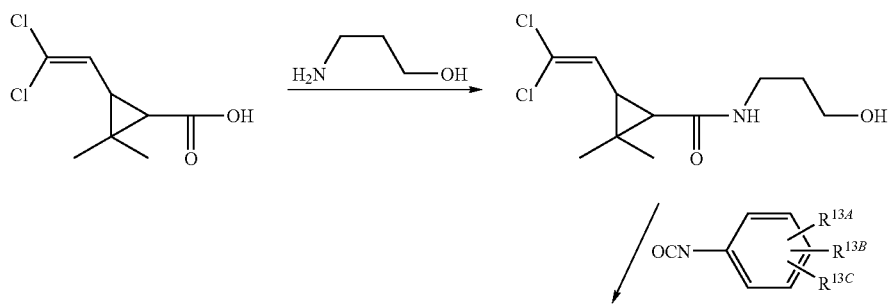

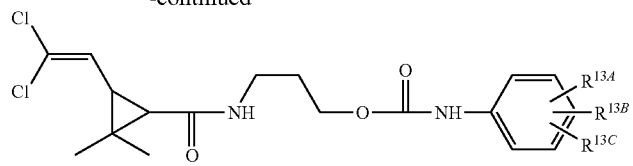

Scheme 13b

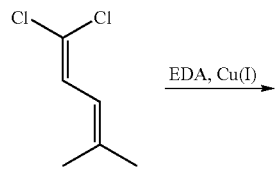

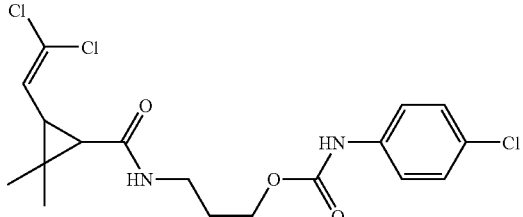

compound M1

Compounds of Formula XIV

Compound's of the invention include compounds of formula (XIV).

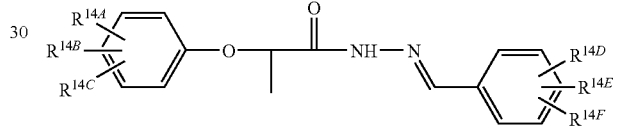

In formula (XIV), each of $R^{14A}$, $R^{14B}$, $R^{14C}$, $R^{14D}$, $R^{14E}$, and $R^{14F}$ is, independently, selected from H, halide, nitro, $C_{1-4}$ alkyl, $C_{2-4}$ alkenyl, $C_{2-4}$ alkynyl, $OR^{14G}$, $OC(O)R^{14H}$, $NR^{14I}R^{14J}$, $NHC(O)R^{14K}$, $NHC(S)R^{14L}$, $NHC(O)OR^{14M}$, $NHC(S)OR^{14N}$, $NHC(O)NHR^{14O}$, $NHC(S)NHR^{14P}$, $NHC(O)SR^{14Q}$, $NHC(S)SR^{14R}$, $NHC(O)_2R^{14S}$, $C(O)OR^{14T}$, and $C(O)NHR^{14U}$; and each of $R^{14G}$, $R^{14H}$, $R^{14I}$, $R^{14J}$, $R^{14K}$, $R^{14L}$, $R^{14M}$, $R^{14N}$, $R^{14O}$, $R^{14P}$, $R^{14Q}$, $R^{14R}$, $R^{14S}$, $R^{14T}$, and $R^{14U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. Formula (XIV) includes compound N1 (see FIG. 15).

Compounds of formula (XIV) can by prepared, for example, by coupling an aryl iodide derivative with carboxy-protected lactic acid. Hydrazinolysis of the resulting product, followed by condensation with a benzaldehyde derivative can yield the desired hydrazide (see Scheme 14a).

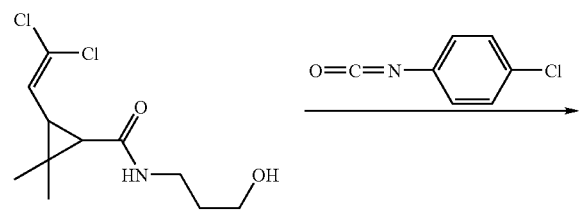

Scheme 14a

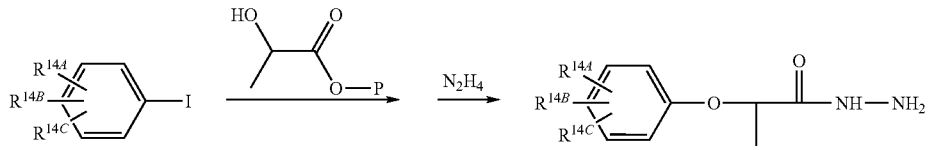

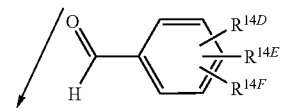

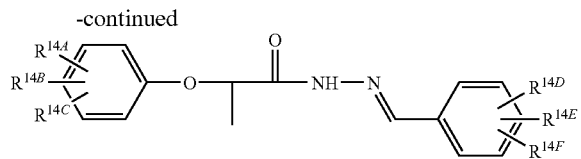
Conditions for coupling aryl iodides and alcohols are described by Manbeck et al., J. Org. Chem. 70:244 (2005) and Wolter et al., Org. Lett. 4:973 (2002), schemes 14b and 14c, respectively.
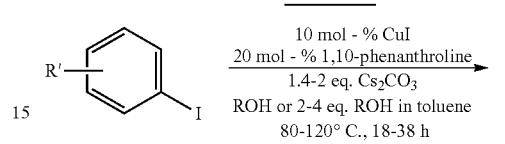
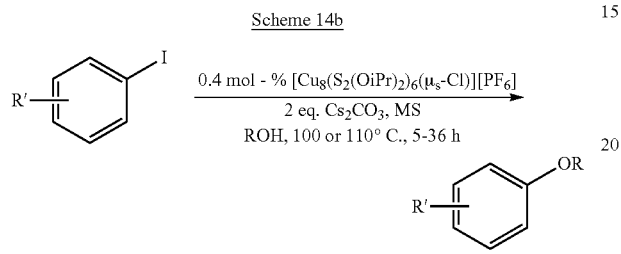
Compound N1 can be prepared as described in Scheme 14d.
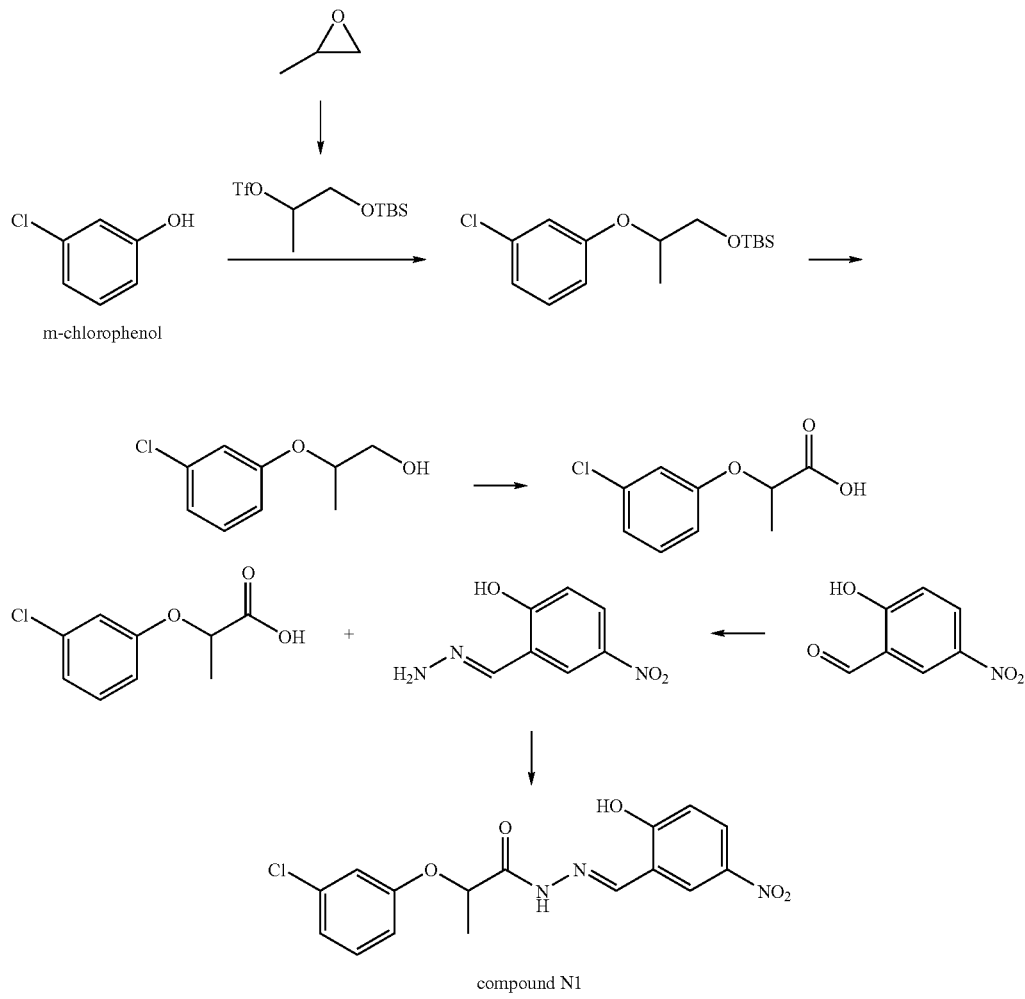

Compounds of Formula XV

Compounds of the invention include compounds of formula (XV).

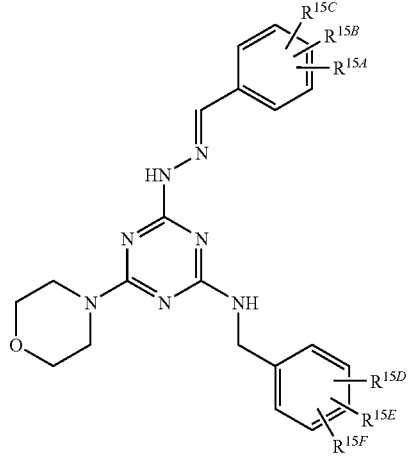

(XV)

In formula (XV), each of $R^{15A}$, $R^{15B}$, $R^{15D}$, $R^{15E}$, and $R^{15F}$ is, independently, selected from H, halide, nitro, $C_{1-4}$ alkyl, $C_{2-4}$ alkenyl, $C_{2-4}$ alkynyl, $OR^{15G}$, $OC(O)R^{15H}$, $NR^{15I}R^{15J}$, $NHC(O)R^{15K}$, $NHC(S)R^{15L}$, $NHC(O)OR^{15M}$, $NHC(S)OR^{15N}$, $NHC(O)NHR^{15O}$, $NHC(S)NHR^{15P}$, $NHC(O)SR^{15Q}$, $NHC(S)SR^{15R}$, $NHS(O)_2R^{15S}$, $C(O)OR^{15T}$, and $C(O)NHR^{15U}$; and each of $R^{15G}$, $R^{15H}$, $R^{15I}$, $R^{15J}$, $R^{15K}$, $R^{15L}$, $R^{15M}$, $R^{15N}$, $R^{15O}$, $R^{15P}$, $R^{15Q}$, $R^{15R}$, $R^{15S}$, $R^{15T}$, and $R^{15U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl. Formula (XV) includes compound O1 (see FIG. 15).

Compounds of formula (XV) can by prepared, for example, by sequential condensation of morpholine, a benzyl amine derivative, and hydrazine with cyanuric acid (Aldrich Cat. No. C9, 550-1). Subsequent condensation with a benzaldehyde derivative can yield the desired hydrazone (see Scheme 15a). Compound O1 can be prepared as described in Scheme 15b.

Scheme 15a

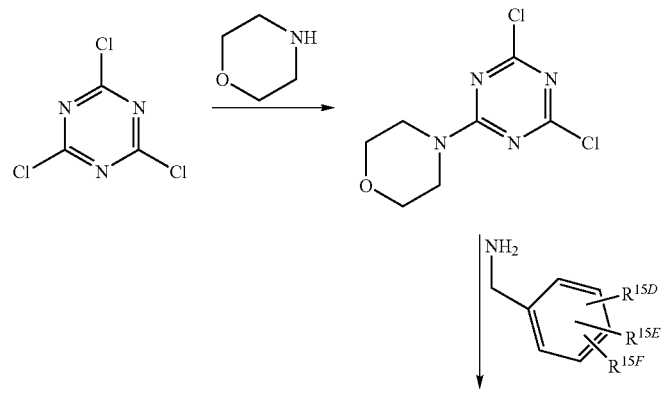

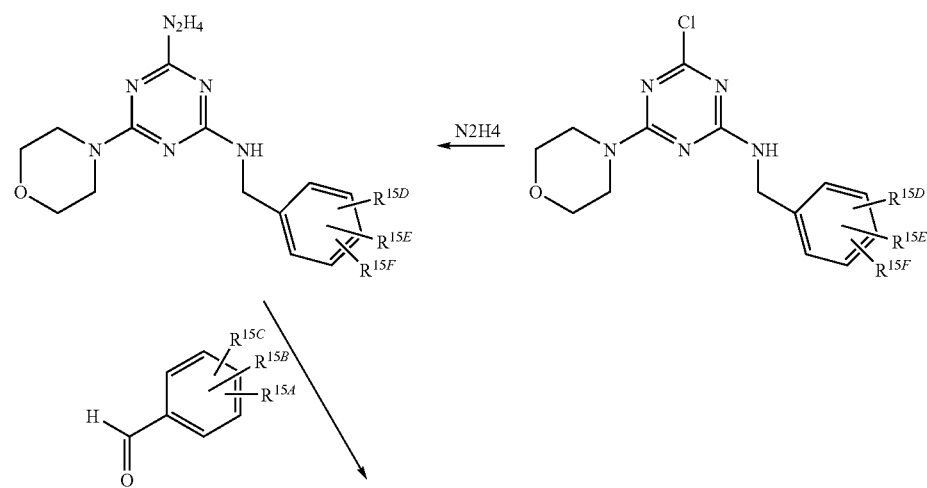

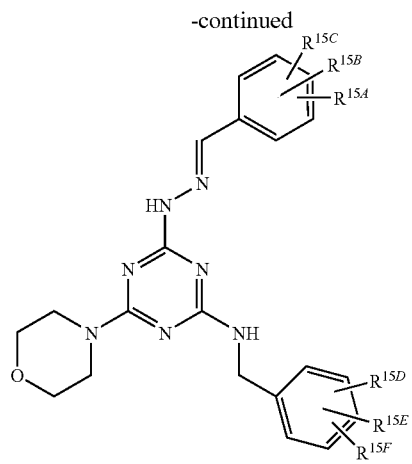

Scheme 15b

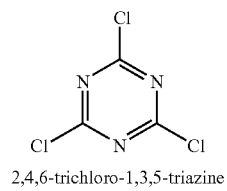

2,4,6-trichloro-1,3,5-triazine

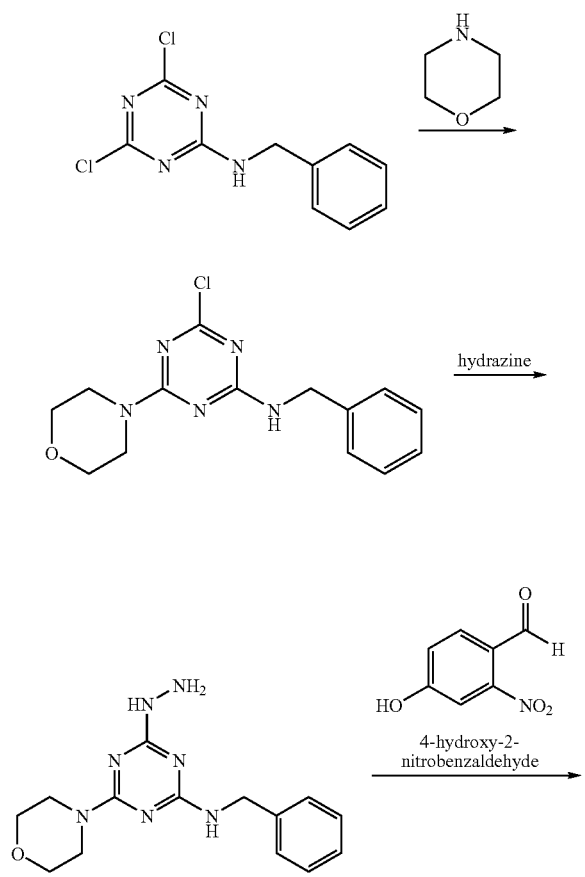

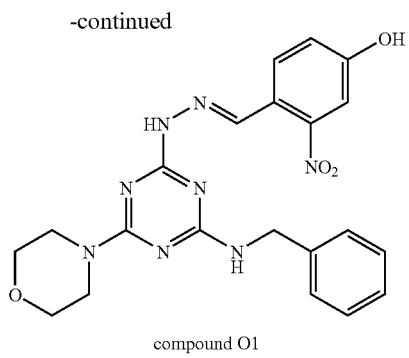

compound O1

Biological Activity

Our screen of a synthetic compound library for substances that cure *C. elegans* of a persistent *E. faecalis* infection suggests that in contrast to a traditional antibiotic screen, the *E. faecalis* assay not only identifies compounds that block pathogen replication in vitro but also identifies compounds that may be prodrugs, that affect the virulence of the pathogen, that suppress pathogen survival, or that enhance the immune response of the host. Because some of the identified compounds only have significant activity in vivo in the whole-animal assay, this provides proof-of-principle for using a whole-animal screen in a drug discovery program to identify novel antimicrobial, antifungal, and antiviral compounds.

One of the most interesting features of many of the identified compounds is their unusual ability to promote nematode survival at concentrations that were much lower than their MIC value in vitro. In contrast, the effective dose in the *C. elegans* curing assay of all of the known antibiotics that we tested was several fold higher than the in vitro MIC. The effective dosage in the nematode model is similar to the therapeutic concentration of most antibiotics in human blood serum, which is typically 5-20 fold higher than the MIC (Schulz et al., Pharmazie 58:447-474 (2003)). A plausible explanation for this observation is that the *C. elegans* curing assay specifically identifies compounds that target functions only important for in vivo survival or virulence, or activators of innate immunity and that compounds with these activities may be more common than traditional antibiotics.

Compounds that inhibit *E. faecalis* virulence could potentially target expression or function of cytolysin, serine protease, gelatinase; the quorum sensing pathway, or colonization of the bacteria in the worm gut. A possible mode of action for these compounds is the inhibition of bacterial colonization, but this activity is difficult to distinguish from antibiotic activity, which also reduces bacterial colonization.

Compounds that function as immune enhancers may activate the C. elegans immune pathway downstream of a conserved p38 MAPK cascade. A cascade consisting of the C. elegans PMK-1, SEK-1, and NSY-1 proteins, corresponding to the p38 MAP Kinase (MAPK), and upstream MAPKK and MAPKKK, is required for the response to a variety of bacterial and fungal pathogens and loss of any of these signaling components results in nematodes that have enhanced susceptibility to the pathogens (Kim et al., Science 297:623-626 (2002)). The C. elegans-E. faecalis curing assay utilized a sek-1 mutant worm strain that dies more quickly when exposed to E. faecalis and a potential activity of a hit would be an activator of the downstream p38 MAP kinase. Restoring the activity of the p38 MAP kinase in the sek-1;glp-4 strain that we used would be detectable in the killing assay since this results in the doubling of the survival time from the E. faecalis infection, as illustrated by comparing the killing kinetics of the glp-4;sek-1 and glp-4 mutants.

Natural or synthetic compounds that block the virulence of pathogens ("virulence anti-infectives") are a largely unexplored class of antimicrobial, antifungal, and antiviral agents. The successful targeting of a virulence product is demonstrated in a recent paper by Hung et al. (Science 310:670-674 (2005)), in which a high throughput screen was used to identify compounds that inhibit the activity of the Vibrio cholerae transcriptional regulator ToxT that is required for expression of cholera toxin and the toxin coregulated pilus. A small molecule identified in this screen, 4-[N-(1,8-naphthalimide)]-n-butyric acid, protected infant mice from intestinal colonization by V. cholerae. Although cholera is effectively treated with a simple fluid-replacement regime, targeting a key toxin or particularly potent virulence factor may be an effective therapeutic in the case of other pathogens.

Therapy

The invention features compositions and methods for treating or preventing a disease or condition in an animal or a plant associated with a microbial or viral infection by administering a compound of formula I-XV.

Compounds of the present invention may be administered by any appropriate route for treatment or prevention of a disease or condition associated with a microbial or viral infection. These may be administered to humans, domestic pets, livestock, or other animals with a pharmaceutically acceptable diluent, carrier, or excipient, in unit dosage form. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

Therapeutic formulations may be in the form of liquid solutions or suspensions; for oral administration, formulations may be in the form of tablets or capsules; and for intranasal formulations, in the form of powders, nasal drops, ear drops, or aerosols.

Methods well known in the art for making formulations are found, for example, in "Remington: The Science and Practice of Pharmacy" (20th ed., ed. A. R. Gennaro, 2000, Lippincott Williams & Wilkins). Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycholate and deoxycholate, or may be oily solutions for administration in the form of nasal drops, or as a gel. The concentration of the compound in the formulation will vary depending upon a number of factors, including the dosage of the drug to be administered, and the route of administration.

The compound may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like.

Administration of compounds in controlled release formulations is useful where the compound of formula I has (i) a narrow therapeutic index (e.g., the difference between the plasma concentration leading to harmful side effects or toxic reactions and the plasma concentration leading to a therapeutic effect is small; generally, the therapeutic index, TI, is defined as the ratio of median lethal dose ($LD_{50}$) to median effective dose ($ED_{50}$)); (ii) a narrow absorption window in the gastro-intestinal tract; or (iii) a short biological half-life, so that frequent dosing during a day is required in order to sustain the plasma level at a therapeutic level.

Many strategies can be pursued to obtain controlled release in which the rate of release outweighs the rate of metabolism of the therapeutic compound. For example, controlled release can be obtained by the appropriate selection of formulation parameters and ingredients, including, e.g., appropriate controlled release compositions and coatings. Examples include single or multiple unit tablet or capsule compositions, oil solutions, suspensions, emulsions, microcapsules, microspheres, nanoparticles, patches, and liposomes.

Formulations for oral use include tablets containing the active ingredient(s) in a mixture with non-toxic pharmaceutically acceptable excipients. These excipients may be, for example, inert diluents or fillers (e.g., sucrose and sorbitol), lubricating agents, glidants, and antiadhesives (e.g., magnesium stearate, zinc stearate, stearic acid, silicas, hydrogenated vegetable oils, or talc).

Formulations for oral use may also be provided in unit dosage form as chewable tablets, tablets, caplets, or capsules (i.e., as hard gelatin capsules wherein the active ingredient is mixed with an inert solid diluent, or as soft gelatin capsules wherein the active ingredient is mixed with water or an oil medium).

The formulations can be administered to human subjects in therapeutically effective amounts. Typical dose ranges are from about 0.01 µg/kg to about 2 mg/kg of body weight per day. The preferred dosage of drug to be administered is likely to depend on such variables as the type and extent of the disorder, the overall health status of the particular subject, the specific compound being administered, the excipients used to formulate the compound, and its route of administration. Standard clinical trials maybe used to optimize the dose and dosing frequency for any particular compound.

For agricultural uses, the compounds described herein and additional compounds identified using the methods disclosed herein may be used as chemicals applied as sprays or dusts on the foliage of plants to treat, for example, cankers, rots (e.g., stalk or root rot), rusts, blights (e.g., potato blight), downey or powdery mildew, scabs, smuts, leaf spot, black spot, vascular wilt disease, crown gall, leaf curl, or hairy root. Typically, such agents are to be administered on the surface of the plant in advance of the pathogen in order to prevent infection. Seeds, bulbs, roots, tubers, and corms are also treated to prevent pathogenic attack after planting by controlling pathogens carried on them or existing in the soil at the planting site. Soil to be planted with vegetables, ornamentals, shrubs, or trees can also be treated with chemical fumigants for control of a variety of microbial pathogens. Treatment is preferably done several days or weeks before planting. The chemicals can be applied by either a mechanized route, e.g., a tractor or with hand applications. In addition, chemicals identified using the methods of the assay can be used as disinfectants.

The formulation of the compounds described herein for agricultural chemical compositions may be an emulsifiable concentrate, a wettable powder, granule, a dust formulation, a suspension concentrate or plowable, as well as a liquid formulation. Accordingly, other additives such as an emulsifier, a dispersing agent, and a carrier may be optionally contained depending on the formulation. Such agricultural chemical compositions may be prepared using standard methods in the art.

The compounds described herein and additional compounds identified using the methods of the invention may also be used to increase growth rate or feed conversion in an animal (e.g., a cow, pig, sheep, goat, duck, chicken, goose, or turkey). For example, the compounds may be administered to the animal by means of an injection, in the feed, or in the drinking water.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

EXAMPLES

Example 1

High-Throughput *C. elegans* Chemical Screens

We developed protocols to perform automated, high-throughput (HT) whole-animal chemical screens. The described methods enable quantitative analyses of a wide range of biological processes such as the response to different types of biotic (pathogens) or abiotic (heavy metals, ultraviolet radiation, heat) stresses that affect viability, as well as traditional longevity studies. We optimized methods to perform screens in liquid media. In particular, for 96- and 384-well format, small perturbations such as salt concentration, amount of food, and the number of animals has a greater effect than in an assay using a larger format.

Exemplary assays described herein were designed to screen for compounds (e.g., low molecular weight compounds) that prevent the lethal effect of the infection of *C. elegans* by a pathogen such as the bacterial pathogen *Enterococcus faecalis*. *C. elegans* were first grown to the young adult stage and then infected on lawns of *Enterococcus faecalis*. The infected worms were washed and transferred to 384-well plates, each well containing liquid media and the compound or compounds to be tested. The plates were incubated until the infection killed untreated worms. The worms were washed and stained with a fluorescent dye such as Nile Red or MitoTracker or a fluorescent dye such as Sytox® orange that specifically stains dead worms. Images of the wells were captured with an automated microscope and analyzed to quantify worm survival.

In particular, the below protocol allows the screening of twenty 384-well plates per experiment. The rate limiting steps are worm dispensing and imaging. Each of these steps takes approximately 15 minutes per plate.

Amplify Worm Stocks (1) Inoculate one colony of *E. coli* HB101 into a 2 Liter flask containing 500 ml LB supplemented with 200 µg/ml streptomycin sulfate. Incubate for 16 hours at 37° C. and 250 rpm. Centrifuge the saturated culture at 5,000×g for 10 minutes and resuspend in LB (Luria Broth; 10 g Bacto-tryptone, 5 g yeast extract, 10 g NaCl, water to 1 liter, pH to 7.5 with NaOH) to concentrate the bacteria 20 fold. Spread 100 µl of the concentrated bacteria onto 90 mm plates of NGM (3 g NaCl, 2.5 g peptone, 17 g agar, 975 ml water, autoclaved, cooled to 55° C. and supplemented with sterile solutions of (i) 1 ml of 5 mg/ml cholesterol dissolved in ethanol (ii) 1 ml 1M $CaCl_2$, (iii) 1 ml 1M $MgSO_4$, and (iv) 25 ml 1M potassium phosphate pH 6.0 (108.3 g $KH_2PO_4$, 35.6 g $K_2HPO_4$, water to 1 liter)), or SK-NS agar (3 g NaCl, 3.5 g peptone, 20 g agar, 975 ml water, autoclaved, cooled to 55° C. and supplemented with sterile solutions of (i) 1 ml of 5 mg/ml cholesterol dissolved in ethanol (ii) 1 ml 1M $CaCl_2$, (iii) 1 ml 1M $MgSO_4$, (iv) 25 ml 1M potassium phosphate pH 6.0, (v) 1 ml 100 mg/ml streptomycin sulfate, and (vi) 1 ml 62.5 U/µl nystatin). (Nystatin and streptomycin are added to inhibit fungal and bacterial contamination, respectively.) Incubate the plates at RT (room temperature) for 1 day to produce the lawns of *E. coli* that will serve as the food source for the worms. Plates can be stored at RT for up to 1 week.

(2) Grow approximately 1,000 glp-4(bn2ts);sek-1(km4) L1 worms on each 90 mm plate of HB101 on NGM at 15° C. for 5 days until the worms become gravid adults.

(i) Harvest the gravid adults by washing the plates with 10 ml of M9 buffer (6 g $Na_2HPO_4$, 3 g $KH_2PO_4$, 5 g NaCl, 0.25 g $MgSO_4.7H_2O$, water to 1 liter) and transfer them into 15 ml conical tubes. Centrifuge the tubes at 1,500×g for 30 seconds to pellet the worms. Remove the supernatant leaving behind 0.5 ml of liquid and the sedimented worms. Immediately before use, prepare a solution consisting of 0.1 ml 5 M NaOH and 0.4 ml bleach, and add the 0.5 ml solution to the tube. Continuously agitate and vortex the tube for 3-5 minutes, until most of the adult worms have ruptured. Do not overexpose to the bleach solution because this will result in damaged embryos. An average of ten to fifteen progeny per glp-4 (bn2ts);sek-1 (km4) adult can be obtained.

(ii) Wash the eggs 3 times with 14 ml M9 buffer.

(iii) Resuspend the eggs in 5 ml M9 buffer and let them hatch at RT for 20 hours with gentle rocking. The hatched worms arrest at the L1 larval stage in the M9 buffer. Seed approximately 4,000 L1 s onto each HB101 on SK-NS plate and grow the worms at 25° C. for approximately 54 hours until the worms become young adults.

Prepare *E. faecalis* Lawns

To prepare *E. faecalis* lawns for the pathogenic *E. faecalis* bacteria as the source of the infection, inoculate one colony of *E. faecalis* strain MMH594 in BHI (Brain-Heart Infusion; BD, Sparks, Md.) liquid media and incubate at 37° C. for 6 hours. Spread 100 µl of the culture over the entire surface of 90 mm plates containing BHI agar. Incubate the plates at 25° C. overnight to grow the lawns and then cool the plates at 15° C.

Infect Adult Worms (1) To each plate of sterile, adult worms, add 15 ml of M9 buffer and resuspend the worms by gently shaking the plate for 10 seconds. Transfer the worms into sterile 50 ml tubes by pouring. Allow the worms to settle to the bottom of the tubes and remove the supernatant. Wash worms twice with M9 buffer to remove the E. coli.

(2) Using large orifice pipette tips, seed the worms onto the lawns of E. faecalis MMH594 on BHI agar. Transfer up to 8,000 animals per plate. Incubate the plates for 15 hours at 15° C. to allow the infection to become established. The worms are infected on lawns of pathogen for a period of time that allows persistent intestinal colonization but at which symptoms of the infection are not yet observed.

Seed Infected Worms in Screening Plates (1) Using a multiplate dispenser, dispense 20 µl of 1.75× media to each well of the 384-well plate. 1.75× media consists of 35% BHI, 63.4% M9 buffer, 1.25% DMSO, 109 U/ml nystatin, and 175 µg/ml kanamycin sulfate.

(2) Pin transfer 100 nl of a 5 mg/ml compound stock dissolved in DMSO into each well of a 384-well plate (final DMSO concentration is 1% and compound concentration is 14 µg/ml).

(3) Sterilize and prepare COPAS Biosort. In particular, the COPAS Biosort is prepared by sterilizing the worm sorter tubing system by running 200 ml of 10% bleach through the system. The bleach is washed out by running 200 ml of sterile ddH$_2$O through the system. The system is further sterilized by running 200 ml of 70% ethanol through the system and the ethanol is washed out by running 200 ml of sterile ddH$_2$O through the system. The system is equilibrated with sample buffer, by running 50 ml of S-buffer through the system.

Following the sterilization and preparation procedure, 200 ml of S-buffer and 2 ml of Sytox®-stained L1 suspension are added to the sample cup. An acquisition cycle of 500 objects is performed. For accurate dispensing of L1s, the flow rate should be approximately 10 events/sec. The L1 suspension is diluted and added accordingly. Based on size and intensity of the fluorescent signal, the gate of interest is defined. A test is performed by dispensing 5 non-Sytox®-stained objects (live L1 s) per well in the cover of a 96-well plate. The accuracy is checked under the dissecting scope.

(4) Resuspend the infected worms in M9 buffer. Dispense 15 young adult worms into each well of the 384-well plates (black walled, clear bottom; Corning Cat. #3712, Lowell, Mass.) using the COPAS Biosort (Harvard Bioscience, Holliston, Mass.). In particular, the worm synchronization method described results in a population of worms in which 95% are young adults. Based on time or flight or length (TOF), the COPAS Biosort differentiates young adults from younger animals. The remaining 5% of the worm population corresponds to slower growing animals that are discarded. The COPAS Biosort transfers each worm in a volume of ~1 µl. The final volume of transferred worms per well is 35 µl. Final concentrations are as follows: 20% BHI, 36% M9 buffer, 1% DMSO, 100 µg/ml kanamycin sulfate, 62.5 U/ml nystatin, and the remaining liquid consists of sheath fluid (worm sorter specific fluid; Pulak, Methods Mol. Biol. 351:275-286, 2006) and M9 buffer.

(5) Dry the top of the 384-well plates with laboratory tissue to allow adhesion of membranes and seal the plates with gas permeable membranes (Diversified Biotech #BEM-1, Boston, Mass.).

(6) Incubate plates at 26.5° C. with 85% relative humidity for 7 days. The plates are placed in a single layer on top of the shelves and incubated without agitation. Roughly 90% of the untreated worms die from the infection during the 7-day incubation period. In contrast, less than 15% of the worms die when treated with antibiotics such as ampicillin or tetracycline. Humidity is set at the maximum of the incubator capacity to reduce evaporation. Alternatively, the microtiter plates could be placed into containers that are lined with wet paper towels.

Prepare Samples to Score (1) Resuspend the worms and bacteria by vortexing the plates for 5 seconds at a high setting. Centrifuge the plates at 1,000×g for 10 seconds to remove the liquid from the membranes. Remove the membrane seals. Using a plate washer, dispense 65 µl of M9 buffer per well using the maximum dispense speed to facilitate washing (e.g., using a thermo multidrop combi (Milford, Mass.) or equivalent liquid dispenser for 384-well microtiter plates). Let the worms settle to the bottom of the wells for at least 3 minutes. Remove three-fourths of the liquid from the top of the plate using the aspirating head of the plate washer (Bio-Tek Elx405, Winooski, Vt.; or equivalent plate washer with an adjustable-height aspiration manifold). Wash the plates a total of 4 times. After the final wash, aspirate enough liquid to leave ~25 µl/well. In addition to staining dead worms, Sytox® Orange also stains the bacteria in the assay wells and therefore the bacteria need to be removed to allow quantification of the fraction of dead worms.

(2) Using the multiplate dispenser, dispense 50 µl of 1 µM Sytox® Orange (Invitrogen Cat. #S11368, Carlsbad, Calif.) diluted in M9 buffer per well resulting in a stain concentration of 0.7 µM.

(3) Seal the plates with gas permeable membranes and incubate at 20° C. for 20 hours at 85% relative humidity (RH). Arrange the plates in a single layer on the incubator shelves and incubate without agitation.

Image Capture

Wells are imaged using a Molecular Devices Discovery-1 automated microscope (Sunnyvale, Calif.) or equivalent. Fluorescent TRITC (535 nm excitation, 610 nm emission) and transmitted light images are captured. Hardware capture conditions are as described in Table 1, except that the focal plane is set at the bottom of the well (laser based scanning). The use of a 2× objective allows capturing the entire area of a well in a 384 well plate.

Settings used to capture images of worms growing on half-area 96-well agar media plates with a Discovery-1 automated microscope are listed (Table 1). Images are taken in 3 wavelengths: bright-field, GFP, and Nile Red.

TABLE 1

| Parameter | Setting |
| --- | --- |
| Plate Reference Point (a) | 14337.5 |
| Reference Objective (b) | 5 |
| Parfocality Offset (c) | 1445 |
| Plate Height (d) | 14.2 |
| Well Depth (e) | 10500 |
| Find 2nd Maximum (f) | FALSE |
| Start z position (g) | 19982.5 |
| Full range (µm) (h) | 1000 |
| Full max step (µm) (i) | 590 |
| Plate bottom exposure (j) | 3 |
| Wide range (µm) (k) | 50 |
| Wide max step (µm) (l) | 10 |
| Accuracy (µm) (m) | 59 |
| Magnification | 2x |

TABLE 1-continued

| Parameter | Setting |
| --- | --- |
| Camera binning | 2 |
| Gain | 2(4x) |
| Transmitted light exposure | 10 ms |
| Image based range (μm) | 500 |
| Max. step (μm) | 100 |
| Nile Red: filter set | 572/630 |
| exposure time | 100 ms |
| GFP: filter set | 470/530 |
| exposure time | 250 ms |

(a) Reference point of flat sheet in plate holder. Value is distance from application Z origin.
(b) Objective position used for setting reference point
(c) Offset distance between current objective to reference point objective
(d) Height defined for current plate
(e) Depth of well for current plate
(f) TRUE = 2 peak search, FALSE = single peak search
(g) Start z position of search in units
(h) Total range covered in μm
(i) Incremental steps in μm
(j) Image exposure (ms)
(k) Search range at bottom of well in μm
(l) Incremental steps in μm
(m) Accuracy to which focus will be found (μm)

Image Analysis

Figure 19:
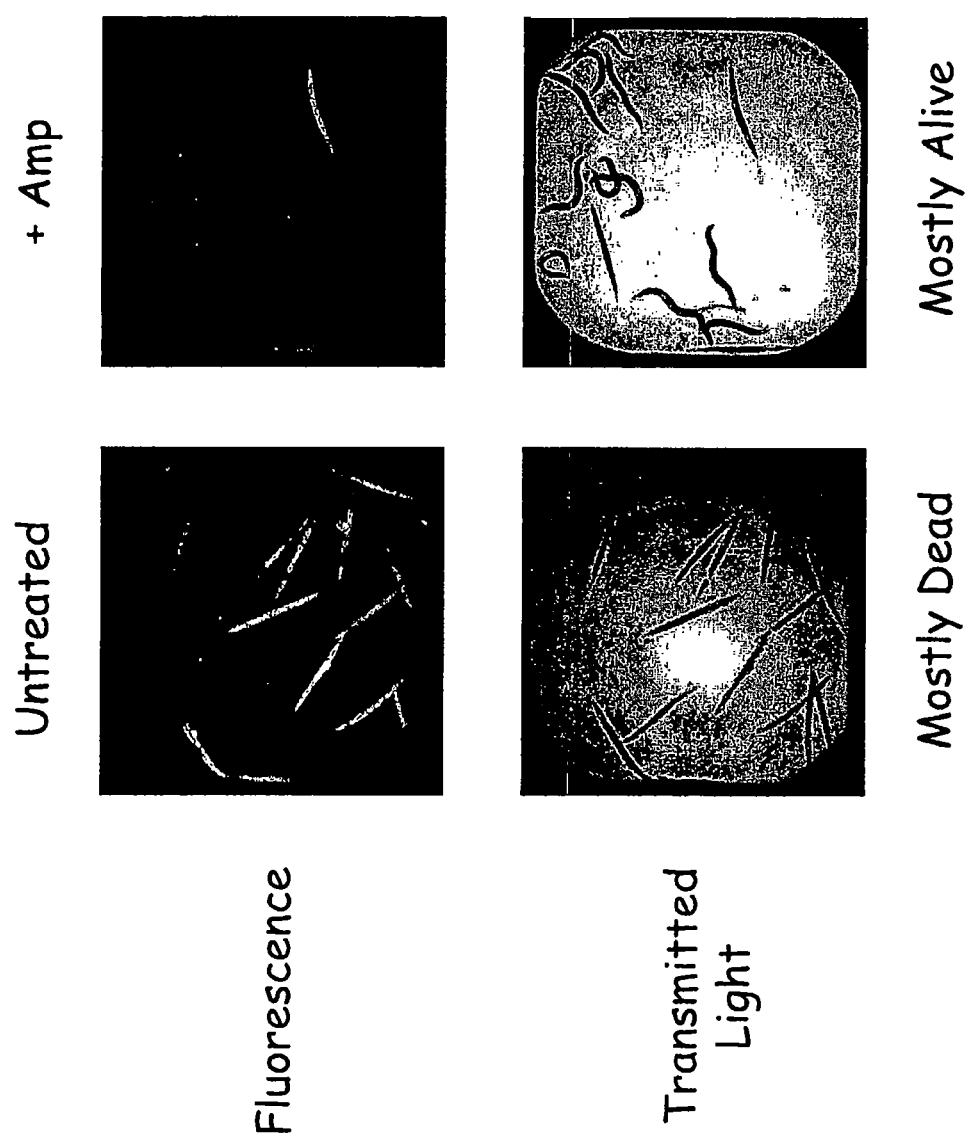
FIG. 19 is a series of images showing that the Sytox® orange fluorophore stains dead worms in the liquid infection assay. At the end point of the infection assay, worms in the 384-well plate were washed to remove the infection media and bacteria. Worms were the incubated with the Sytox® orange, which specifically stains dead and dying worms. Fluorescent and transmitted light images were captured for each well. The images displayed on the left column are from an untreated well in which most of the worms are dead and fluorescent. The images displayed on the right column are from an ampicillin-treated well in which most of the worms are alive and not fluorescently-labeled.
Figure 20:
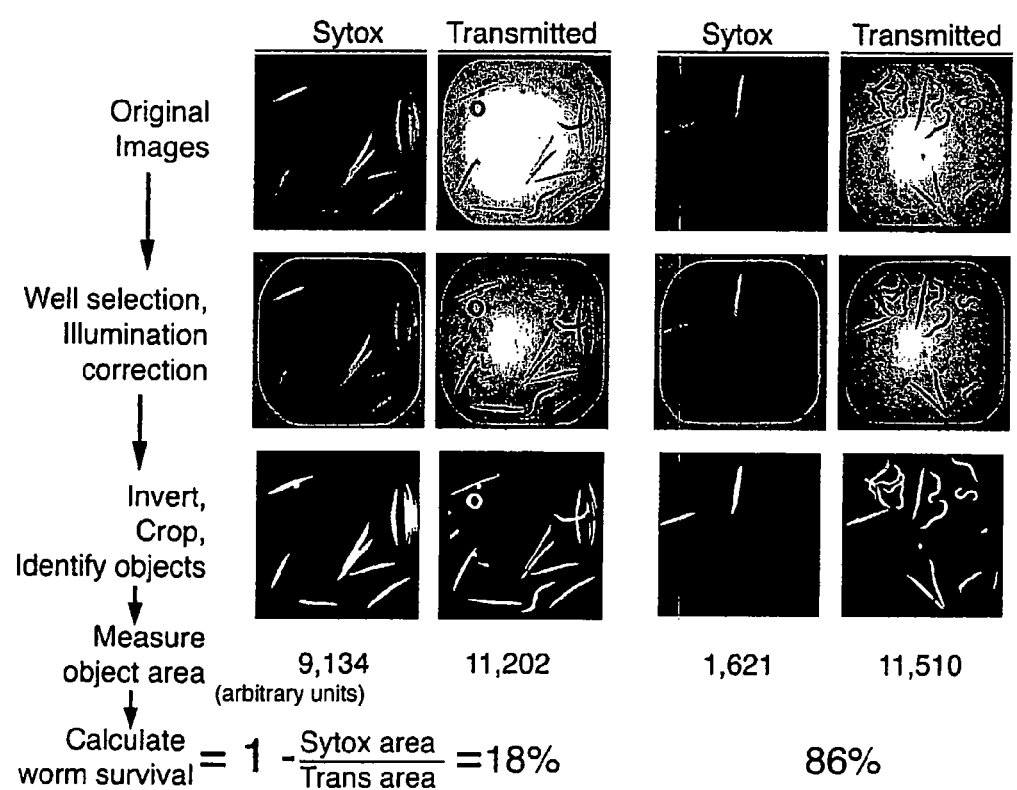
FIG. 20 is a series of images and a schematic diagram showing worm survival quantification using CellProfiler software. After drug treatment (e.g., vancomycin), worms in 384-well plates are incubated with Sytox® orange, which specifically stains dead worms. The top row shows raw fluorescent Sytox® orange and bright-field images captured using a 2× objective. The images were analyzed using CellProfiler software through a pipeline of 22 processing steps. The results of two of the processing steps are shown. Images in the middle row show the results of well area selection and light correction of the bright-field images. Images in the bottom row show the result of the worm identification function after inverting and cropping the well area. Finally, the total object area of the fluorescent and the bright-field images are measured. Assuming that there are exactly the same number of worms per well (±5% sorting error) and that all worms have roughly the same size, the Sytox® orange objects area and bright-field objects area are used to approximate the number of dead worms and the total number of worms, respectively. Worm survival=1−(Sytox® orange area/total bright-field worm area).

Analysis is performed with CellProfiler software which is publicly available at cellprofiler.org. An optimized pipeline to quantify worm survival (1-(Sytox® Orange worm area/bright-field worm area)=1-(dead worm area/total worm area)) is also available at cellprofiler.org. An example of the quantification of worm survival using the described methodology is shown in FIGS. 19 and 20. Survival can be determined by measuring areas (number of pixels) instead of counting worms. CellProfiler cannot distinguish overlapping worms as independent objects. Also, the intensity of fluorescent Sytox® orange staining in dead worms varied greatly. This variation, in addition to the inhomogeneous nature of the worm suspensions, also prevented the use of a fluorescent plate reader.

Example 2

High-Throughput *C. elegans* Screen for Identifying Chemical Compounds with Antimicrobial Activity Materials and Methods Bacterial and Nematode Strains.

Wild-type Bristol N2 (Brenner S., *Genetics* 77: 71-94 (1974)) and glp-4(bn2ts);sek-1 (km4) (Beanan et al., Development 116:755-766 (1992); and Tanaka-Hino et al., EMBO Rep 3:56-62 (2002)) *C. elegans* strains were maintained using standard practices (see Lewis et al., Basic Culture Methods. In: Epstein H F, Shakes D C, editors. *Caenorhabditis elegans* Modern Biological Analysis of an Organism. San Diego, Calif.: Academic Press. pp. 3-29 (1995)). *E. faecalis* strains MMH594 (Huycke et al., Antimicrob. Agents Chemother. 35:1626-1634 (1991)), OG1RF (Murray et al., J. Bacteriol. 175:5216-5223 (1993)), OG1RF ΔfsrB (Qin et al., Infect. Immun. 68:2579-2586 (2000)), V583 (Sahm et al., Antimicrob. Agents Chemother. 33:1588-1591 (1989)), VS583 (Moy et al., Infect. Immun. 72:4512-4520 (1989)) and *E. faecium* strains DO (Arduino et al., Infect. Immun. 62:5587-5594 (1994)) and 11M12 (Moy et al., Infect. Immun. 72:4512-4520 (1989)) were grown on brain heart infusion (BHI) media (Difco Becton Dickinson, Sparks, Md.) at 37° C.

Nematode Killing and Rescue.

N2 or glp-4(bn2ts);sek-1 (km4) worms were synchronized by isolating eggs from gravid adults, hatching the eggs overnight in M9 buffer, and plating L1-stage worms onto lawns of *E. coli* on NGM agar media. Worms were grown to sterile, young adults by incubation at 25° C. for 48 to 52 hours, washed off the plates with M9 buffer, resuspended and washed in M9 buffer, deposited onto lawns of *E. faecalis* grown on BHI agar plates containing kanamycin at 80 μg/ml to inhibit *E. coli* growth, incubated for 8 to 12 hours at 25° C., and resuspended in M9 buffer. For assays using agar media, approximately 35 infected worms were washed and then deposited onto 35 mm plates containing the appropriate antibiotics. Plates were incubated at 25° C. and scored for worm survival at regular intervals. Worms were considered dead if they were unresponsive to touch with a platinum wire pick. For the initial assays using liquid media, approximately 80 infected worms were transferred to wells of a 6 well plate containing 2 ml media consisting of 10% BHI 80 μg/ml kanamycin, 90% M9 buffer, and the appropriate antibiotics. The plates were incubated without agitation at 25° C. and 80-85% relative humidity. To score for worm survival, the 6 well plates were shaken by hand, and the worms were considered to be dead if they did not move or exhibit muscle tone.

Bacterial Colonization.

Infected worms were washed three times with M9 buffer containing 1 mM sodium azide. Approximately 10 worms were transferred to a 2 ml microcentrifuge tube and the volume was brought to 250 μl. Fifty μl of buffer was removed and plated to determine the number of external CFU. Approximately 400 mg of 1.0 mm silicon carbide particles (BioSpec Products, Catalog #11079110sc) were added to each tube, the tubes were vortexed at maximum speed for one minute, which disrupts the worms but does not affect bacterial survival, and the resulting suspension was diluted and plated onto selective media to determine CFU.

Screening for Anti-Infectives.

Synchronized L4 stage to young adult glp-4(bn2ts);sek-1 (km4) worms were infected for 8 hours on lawns of MMH594 as described above. The worms were resuspended in media composed of 20% BHI, 80 μg/ml kanamycin, and 80% M9 buffer. Approximately 25 worms in a volume of 50 μl were transferred into 0.3 ml wells of 96 well plates. An equal volume of liquid media containing 125 units/ml nystatin and the compounds to be tested were mixed into the wells. Each compound was tested in individual wells and the screen was performed using duplicate 96 well plates. The final concentration of compounds from ChemBridge Diverset E was 25 μg/ml with dimethyl sulfoxide (DMSO) at 1%. The plates were sealed with gas permeable membranes (Breatheasy, Diversified Biotech, Boston Mass.) and incubated without agitation at 26° C. and 80-85% relative humidity.

Each 96 well plate contained 80 test compounds that were tested with worms infected with the cytolysin-positive *E. faecalis* strain MMH594. The remaining 16 wells contained positive and negative controls to determine whether the assay yielded predictable and reproducible responses to antibiotics or avirulent *E. faecalis* mutants and a clear threshold between positive and negative responses. Each plate contained 8 negative control wells that did not contain any antinfective compound and 4 positive control wells that contained 20 μg/ml ampicillin (2 wells) or 20 μg/ml tetracycline (2 wells). These control wells were seeded with glp-4;sek-1 infected with *E. faecalis* MMH594. In addition, each plate contained 4 positive control wells that were seeded with glp-4;sek-1 worms infected with the *E. faecalis* ΔfsrB mutant.

In total, there were 1,312 control wells in the ChemBridge and NCI screens. The false positive rate was 2.7% and the false negative rate was 1.9%. False positives were defined as more than 50% survival of infected worms in wells that did not contain an antibiotic. False negatives were defined as less than 50% survival of worms treated with an antibiotic or infected with the ΔfsrB mutant.

Worm survival was scored manually after 6 days of incubation. A total of 6,000 compounds were tested from a ChemBridge library Diverset E. Compounds that increased worm survival by two- to three-fold were retested for activity. Ninety ChemBridge compounds were retested in the worm infection model. Eighteen of the compounds promoted worm survival upon retesting. Additional quantities of the 18 ChemBridge hits were ordered from ChemBridge, Inc. for further analysis and use in antibacterial susceptibility testing. MICs were determined against *E. faecalis* strain MMH594 using 2-fold dilution in BHI media according to the broth microdilution protocol of the NCCLS (CLSI) (National Committee for Clinical Laboratory Standards, Approved Standard M7-A5; Methods for Dilution Antimicrobial Susceptibility Tests for Bacteria that Grow Aerobically, Villanova, Pa.: NCCLS (2000)). The compounds were also tested by their ability to hemolyze sheep erythrocytes based on the protocol of Ciornei (Ciornei et al., Antimicrob. Agents Chemother. 49:2845-2850 (2005)) with the following modifications: sheep erythrocytes (Rockland Immunochemicals Inc., Gilbertsville, Pa.) were treated with 100 µg/ml of the compounds in phosphate-buffered saline with DMSO at 2% for 2 hours and the supernatants were monitored at $OD_{540}$. The results are provided in Table 2 (below).

TABLE 2

| Compound | Fold Survival vs untreated[2] | Therapeutic Concentration (µg/ml) | Amt. Colonization vs untreated[3] | MIC (µg/ml) |
| --- | --- | --- | --- | --- |
| A1 | 3.0 | 25 | 22% | >125 |
| B1 | 2.6 | 12.5 | 13% | >125 |
| C1 | 2.7 | 50 | 7% | >125 |
| D1 | 2.3 | 12.5 | 1% | >125 |
| E1 | 3.0 | 25 | 1% | 31.3 |
| E30 | 1.6 | 6.3 | 2% | >30[1] |
| F1 | 3.1 | 25 | 3% | >125 |
| G1 | 3.3 | 25 | 6% | 31.3 |
| H1 | 3.0 | 50 | 1% | 15.6 |
| I1 | 2.7 | 6.3 | 9% | 7.8 |
| J1 | 2.1 | 6.3 | 11% | 2.0 |
| K1 | 1.9 | 100 | 61% | >125 |
| L1 | 1.8 | 25 | 101% | >125 |
| M1 | 2.2 | 100 | 8% | >125 |
| N1 | 2.6 | 25 | 5% | 3.9 |
| O1 | 2.6 | 25 | 8% | 15.6 |
| Tetracycline[4] | 4.0 | 1.6 | 5% | 0.24 |

[1]aqueous solubility limit.
[2]untreated = 24% survival.
[3]100% = 3.28 × 10[4] CFU/worm.
[4]control.

Toxicity Testing.

Fifteen out of 16 compounds identified in this study did not show any signs of toxicity against *C. elegans* or mammalian erythrocytes indicating that the screen was able to select against toxic compounds. These results indicate that the worm infection model will be able to select against at least some compounds that exhibit toxicity. In other studies, *C. elegans* has been used as an indicator of toxicity from heavy metals, environmental pollutants, organic solvents, and neurotoxins (Sochova et al., Environ. Int. 32:374-83 (2005)). Toxicity against nematodes has been quantified based on nematode survival, growth, reproduction, expression of stress response proteins, feeding behavior, and movement. The utility of *C. elegans* in toxicology testing greatly depends on how it correlates to toxicity in mammalian models. Williams and Dusenbery (Williams et al., Toxicol. Ind. Health 4:469-478 (1988)) determined that toxicity of heavy metals against *C. elegans* as measured by the LC50 values (concentration resulting in 50% death) correlates well with toxicity against mice or rats in rank order tests. Additionally, Cole et al. reported a significant correlation from rank order toxicity tests from organophosphates between *C. elegans* and rodents (Cole et al., Toxicol. Appl. Pharmacol. 194:248-256 (2004)).

Example 3

High-Throughput *C. elegans* Screen for Identifying Chemical Compounds with Antifungal Activity Our objective was to develop a semi-automated, high throughput, whole animal *C. elegans* assay useful for identifying chemical compounds with antifungal activity. Key features of the *C. elegans* assay are that it allows concurrent evaluation of toxicity and antifungal activity and that it identifies compounds that target important pathways associated with human *Candida* infection, including filament formation. Moreover, the assay allows the study of *Candida* cells that are in non-planktonic form and identification of antifungal compounds in a system where both the pathogen and the host can be genetically manipulated.

Materials and Methods.

Strains and Media.

The *Candida* strains used in these experiments are summarized in Table 3 or described in the text. Yeast cultures were maintained on Yeast Peptone Dextrose (YPD, Difco) agar or as frozen stocks. The *C. elegans* strains were propagated on *E. coli* strain OP50 or *E. coli* strain HB101 using established procedures (Moy et al., *Proc. Natl. Acad. Sci. USA* 103:10414 (2006) and Brenner, S. *Genetics* 77:71 (1974)).

TABLE 3

| *Candida* Strain | Description | Relevant Characteristics or Phenotype | $LT_{50}$[a] |
| --- | --- | --- | --- |
| DAY185[b] | Arg+ Ura+ His+ Reference strain | Forms meshwork comprised almost exclusively of long hyphae MIC: 0.5 µg/ml for amphotericin B, 2 µg/ml for fluconazole and caspofungin | 3 days |
| MLR28[b] | KEM1 reconstituted strain | Restored the ability to form normal hyphae | 3 days (no difference) |
| GKO443[b] | suv3 | Biofilm-defective mutant that is defective in hypha production | 6 days (P < .0001) |

TABLE 3-continued

| Candida Strain | Description | Relevant Characteristics or Phenotype | $LT_{50}{}^a$ |
|---|---|---|---|
| MLR3[b] | SUV3 reconstituted strain | Produced thick biofilms containing hyphae and excluded calcofluor from the basal cell layers | 4 days (no difference) |
| MLR74[b] | kem1 deletion mutant | Biofilm-defective mutant that is defective in hypha production | 5 days (P = 0.0008) |
| MLR62[c] | GFP-expressing WT | GFP gene linked to the constitutively active TEF1 promoter | 4.5 days |
| C. albicans ATCC#90028[d] | WT | Isolated from blood, Iowa MIC: 2 μg/ml for amphotericin B and 1 μg/ml for caspofungin | 3.5 days |
| C. krusei ATCC#6258[d] | WT | Isolated from sputum of patient with bronchomycosis, Sri Lanka MIC: 2 μg/ml for amphotericin B[d], 32 μg/ml for fluconazole[d] and 0.5-2 μg/ml caspofungin | 4 days |
| C. parapsilosis ATCC#22019[d] | WT | Isolated from case of sprue, Puerto Rico MIC: 2 μg/ml for amphotericin B[d], 2 μg/ml for fluconazole[d] and 0.5-2 μg/ml caspofungin | 3 days |
| C. albicans HGFP3[e] | Transformed with pHWP1GFPS | Expresses GFP in a hyphae-specific manner | ND |

[a]C. elegans strain glp-4; sek-1 killing (P value compared to parent strain, when relevant);
[b]Richard et al., Eukaryot Cell 4: 1493 (2005);
[c]Nobile et al., Curr. Biol. 15: 1150 (2005);
[d]STANDARDS., N.C.F.C.L. Methods for antifungal disk diffusion susceptibility testing of yeasts; approved guideline M44-A. (National Committee for Clinical Laboratory Standards, Wayne, Pa., 2004.);
[e]Staab et al., Microbiology 149: 2977 (2003)
Abbreviations: ATCC: American Type Culture Collection, GFP: Green fluorescent protein, LT: Lethal Time to mortality, MIC: Minimal Inhibitory Concentration, ND: Not done, WT: Wild type C. elegans Liquid Medium Killing Assays.

Candida strains were inoculated in 2 ml of YPD and grown at 30° C. for 24 hours. Lawns were prepared by spreading 10 μl of each culture on 35 mm tissue-culture plates (Falcon) containing solid brain heart infusion (BHI) media (Difco) with kanamycin (45 μg/ml), ampicillin (100 μg/ml), and streptomycin (100 μg/ml). The plates were incubated at 30° C. for 24 hours followed by 25° C. for 24 hours. glp-4;sek-1 and glp-4 worms were grown at 15° C. until they reached the L2 stage, and then they were transferred to 25° C. for 24 h. N2 wild-type worms were grown at 15° C. for 72 h, until they reached the L4 stage. Approximately 100 worms were picked onto each lawn and allowed to feed for 30 minutes to 2 hours. The worms were washed off the plates with M9 buffer and allowed to crawl on unseeded BHI plates to remove yeast cells from their cuticles. Roughly 70-80 worms were then picked to wells in a six-well microtiter dish that contained 1.5 ml liquid medium of 79% M9 buffer, 20% BHI, 2 μM cholesterol and 90 μg/ml kanamycin. The plates were incubated at 25° C. overnight and then examined at 24-hour intervals for survival. Worms were considered dead when they did not respond to being touched with a platinum wire pick.

C. elegans Filamentation Staining.

C. albicans strains DAY185 and HGFP3 lawns were prepared and C. elegans glp-4;sek-1 worms exposed to C. albicans as described above for the killing assays. The worms were then transferred to the liquid media described above in both the presence and absence of 32 μg/ml fluconazole. At 24, 48, 144, and 192 hours, 20-40 worms exposed to DAY185 were stained in 200 μl of 10 μM and 25 g/ml Concavalin A-Alexafluor for 45 minutes (Li et al., Microbiology 149:353 (2003)). Pictures were taken with a confocal laser microscope (TCS NT, Leica Microsystems). FUN-1 is a fluorescent yellow dye that is absorbed by metabolically active fungal cells and fluoresces red when illuminated with 480 nm (fluorescence emission). Concavalin A-Alexafluor (fluorescence emission at 519 nm) is a fluorescent green dye that binds to polysaccharides and stains filaments.

Evaluation of Fungal Burden within C. elegans.

The number of C. albicans colony forming units in C. elegans was quantified based on the protocol detailed by Tang et al., Infect. Immun. 73:8219 (2005) and Garsin et al., Proc. Natl. Acad. Sci. USA 98:10892 (2001) with a few modifications. C. albicans strain MLR62 lawns were prepared on BHI as described above. C. elegans glp-4;sek-1 worms were exposed to the lawns for 30 minutes and then moved to liquid media and incubated at 25° C. in the presence or absence of antifungal agents. At appropriate time points, 3 groups of 10 worms each were washed twice in 8 μl drops of M9 buffer on BHI agar plates, in order to remove surface Candida. Each group of 10 worms was then disrupted using a Pellet Pestle Motor (Kontes) and plated on YPD agar containing kanamycin (45 μg/ml), ampicillin (100 μg/ml), and streptomycin (100 μg/ml). The plates were incubated for 48 hours at 30° C. and colonies were counted.

Screen of Compound Library in C. elegans

For testing the efficacy of chemical compounds, C. albicans strain MLR62 was inoculated into 2 ml of YPD and grown at 30° C. for 24 hours; 10 μl of the culture was spread on 35-mm tissue-culture plates (Falcon) containing brain heart infusion (BHI) agar (Difco) with kanamycin (45 μg/ml), ampicillin (100 μg/ml), and streptomycin (100 μg/ml). The plates were incubated at 30° C. for 24 hours. C. elegans animals at the L4 developmental stage (grown as detailed above under C. elegans liquid medium killing assays) were transferred from a lawn of E. coli HB101 onto C. albicans lawns on BHI medium, incubated at 25° C. for 30 minutes, and then pipetted in 50 μl into 96-well plate wells that contained 100 μl liquid media (79% of M9 buffer, 20% BHI media, 2 μM cholesterol and 90 μg/ml kanamycin). C. elegans glp-4;sek-1 nematodes were pipetted into 96-well plates that contained compounds from chemical libraries. Library 1361 was assembled by Biomol and contains well-characterized compounds that affect many different aspects of cellular pathways. The NINDS custom collection (plates 501-503) was put together by MicroSource Discovery Systems for the National Institute of Neurological Disorders and Stroke (NINDS), the Huntington's Disease Society of America (HDSA), the Amyotrophic Lateral Sclerosis (ALS) Association, and the Hereditary Disease Foundation (HDF). It mostly contains FDA approved drugs. The Prestwick library (plate 1569) contains compounds that are known to be safe and bioactive in humans. The majority of the compounds are marketed drugs.

On day 6, nematodes were evaluated for survival, filament formation and optical density. The plates were incubated at 25° C. and examined on day 6 for survival with a Nikon SMZ645 dissecting microscope. In addition, images were obtained using a CellWorx High Content Cell Analysis System (Applied Precision) at 4× magnification. Dead worms were counted but not removed. Worms were considered dead if they had developed filamentation, were rod shaped, or did not respond to the well being tapped. Each compound was also scored by the number of dead worms in the well that developed hyphea. Compounds were considered to have completely or almost completely inhibited filament formation if fewer than 25% of the dead worms in the well developed hyphea. Compounds were categorized as having a minimal effect on filament formation if 25-75% of the dead worms developed hyphea. The compounds that had no effect of filament formation allowed over 75% of the dead worms to form hyphea.

Approximately 25 nematodes were used to analyze each chemical compound tested. Two controls were used in all plates. The positive control was the antifungal caspofungin (that allows >75% survival at day 6). PBS was the negative control (<25% of nematodes in PBS are alive at Day 6). In this pilot screen, we considered a compound as a "hit" when survival in the compound well with was 50% and above of the median survival of the control wells. Depending on the compound library, the final concentration of the compounds was 33.33 μg/ml, 13.33 μg/ml, or 6.67 mM.

Results.

Killing of *C. elegans* by *Candida* spp.

Figure 16:
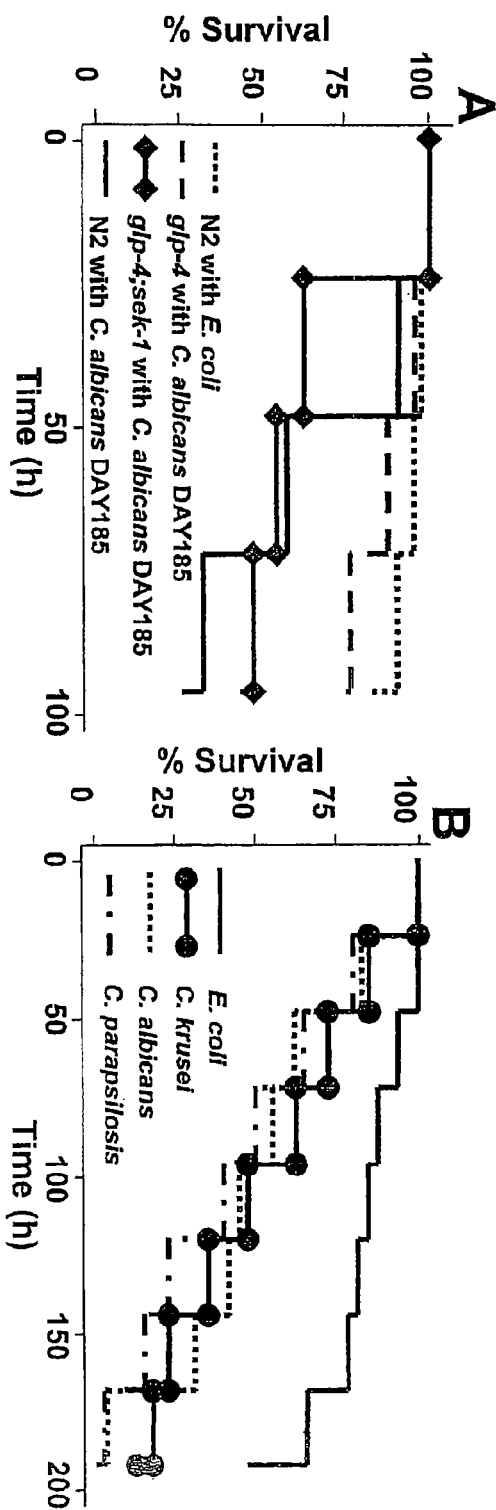
FIGS. 16A and 16B are a series of graphs showing that killing of *C. elegans* nematodes after exposure to *Candida* spp. depends on the nematode MAPK-pathway and on the *Candida* strain.

We sought to develop a *C. elegans-Candida* spp. killing assay that could be performed in liquid media. We found that when wild-type L4 stage N2 nematodes were fed *Candida* spp. on solid brain heart infusion (BHI) medium for 2 hours and then transferred to a liquid medium consisting of 20% BHI and 80% M9 buffer, the longevity of the worms was significantly reduced compared to worms not infected with *Candida* (FIG. 16a). Notably, because of brood production, we removed progeny nematodes that survived beyond the L1 or early L2 developmental stage. We tested different times of exposure to *Candida* spp. on solid BHI medium (from 5 minutes to 24 hours) and in all cases the longevity of the worms was significantly reduced compared to un-infected worms.

Although *Candida* spp. kill wild-type *C. elegans* in liquid medium, the killing does not occur rapidly enough to prevent the production of progeny produced by 3- and 4-day old hermaphroditic nematodes. The presence of a brood in the assay mix makes it difficult to score the viability of the infected parents. Moreover, *Candida*-infected wild type nematodes exhibit significant matricidal death (over 30%) involving the premature hatching of eggs in the *C. elegans* uterus (which is not directly associated with an infectious-like process) around day 3 of the experiment. To avoid these problems associated with progeny production, we substituted *C. elegans* glp-4 mutants for wild-type in the *Candida* spp. killing assay. *C. elegans* glp-4 mutant animals have normal morphology and brood sizes at 15° C., but do not make gonads and are unable to produce eggs at 25° C. (see Moy et al., *Proc. Natl. Acad. Sci. USA* 103:10414 (2006); Mylonakis et al., *Proc. Natl. Acad. Sci. USA* 99:15675 (2002); Beanan et al., *Development* 116:755 (1992); and Roussell et al., *Proc. Natl. Acad. Sci. USA* 90:9300 (1993)). As shown in FIG. 16a, *Candida* spp. also killed glp-4 nematodes, but the rate of killing was significantly slower than for wild-type worms, similar to results reported previously for the killing of glp-4 and other sterile mutants by bacterial pathogens.

Although glp-4 mutant worms could have potentially been used in a anti-fungal screening assay, we sought to increase the rate of killing of the glp-4 mutant by utilizing glp-4;sek-1 double mutant worms. SEK-1 encodes a *C. elegans* homologue of the mammalian p38 mitogen activated protein kinase (MAPK) that was shown previously to be an important component of the *C. elegans* defense response to pathogens (see Moy et al., *Proc. Natl. Acad. Sci. USA* 103:10414 (2006) and Kim et al., *Science* 297:623 (2002)). As shown in FIG. 16a, the *C. elegans* glp-4;sek-1 double mutant is significantly more susceptible to *Candida*-than the glp-4 mutant (P<0.001), suggesting that the *C. elegans* homologue of the mammalian p38 MAPK is involved in the *C. elegans* immune response to *Candida*, similar to it role in candidiasis in mammals (Deva et al., *J. Immunol.* 171:3047 (2003)) and consistent with the observation that sek-1 mutants are more susceptible to a variety of pathogens (see Moy et al., *Proc. Natl. Acad. Sci. USA* 103:10414 (2006) and Kim et al., *Science* 297:623 (2002)). Because the glp-4;sek-1 mutant was similarly susceptible to a variety of *C. albicans* and non-albicans strains (FIG. 16b), because it did not produce progeny, and because we found it compelling to study *Candida* pathogenesis in immunocompromised nematodes (because of the analogy with candidiasis in immunocompromised humans), we utilized the glp-4;sek-1 strain in all of the further studies described below.

Antifungals Prolong Nematode Survival

Figure 17:
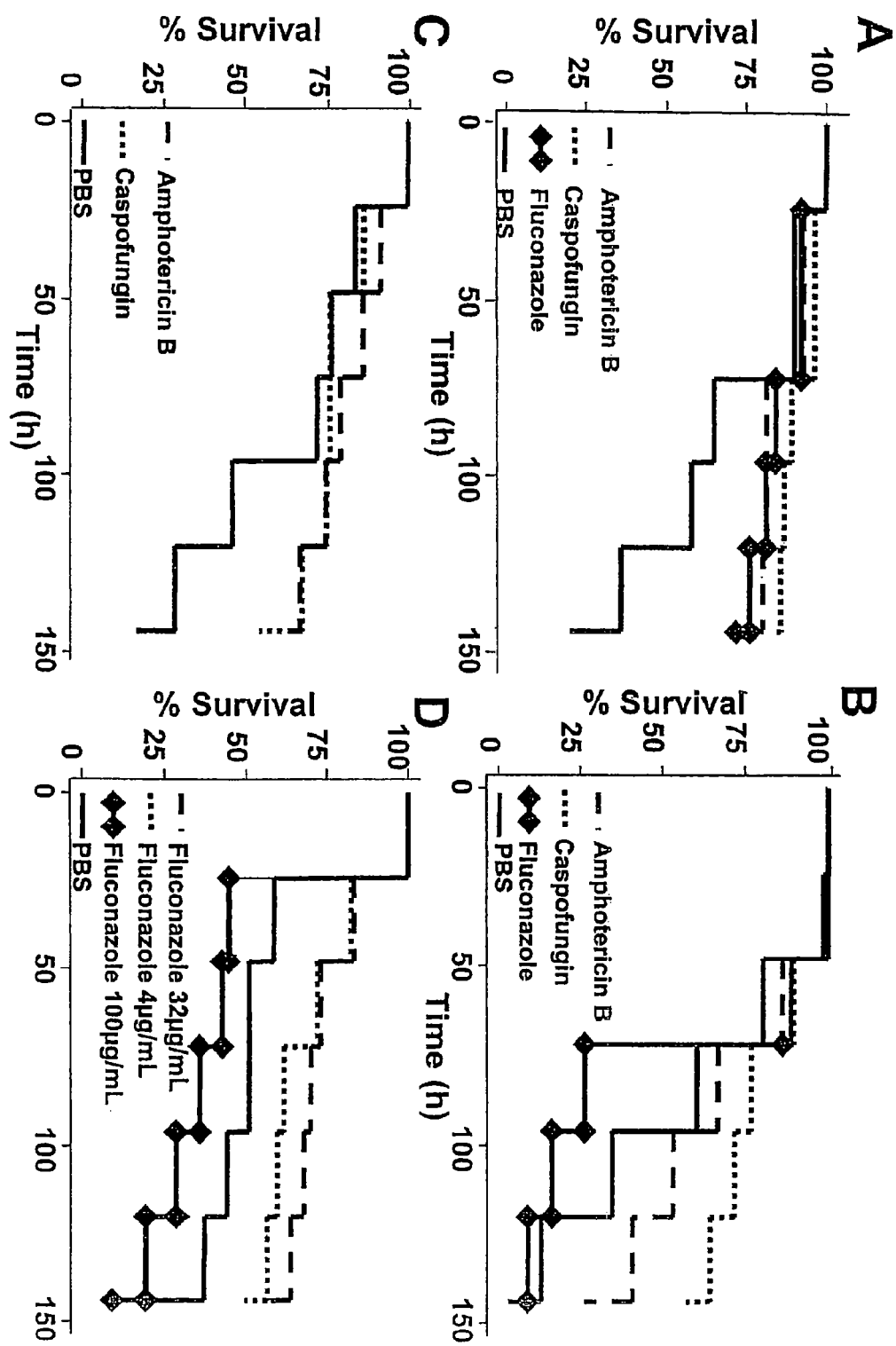
FIGS. 17A through 17D are a series of graphs showing that established antifungals prolong the survival of *C. elegans* glp-4;sek-1 nematodes infected by *Candida* spp. and evaluation of antifungals in the *C. elegans* assay allows the concomitant evaluation of toxicity.

To develop a system that allows high throughput screening for antifungal compounds, we first evaluated whether established antifungals prolong the survival of nematodes infected with *Candida* spp. For this, we used different *C. albicans* isolates as well as non-albicans strains, including those used as reference strains by clinical microbiology laboratories (STANDARDS, N.C.F.C.L. Methods for antifungal disk diffusion susceptibility testing of yeasts; approved guideline M44-A. (National Committee for Clinical Laboratory Standards, Wayne, Pa., 2004)). Notably, all strains tested are susceptible to amphotericin B and caspofungin, but have different susceptibilities to fluconazole (Richard et al., *Eukaryot Cell* 4:1493 (2005); Staab et al., *Microbiology* 149:2977 (2003); Nobile et al., *Curr. Biol.* 15:1150 (2005); and Espinel-Ingroff et al., *J. Clin. Microbiol.* 36:2950 (1998)). We found that antifungals that are active against a particular *Candida* strain resulted in prolongation of *C. elegans* survival when the nematodes were infected with the relevant *Candida* strain (FIGS. 17a-d). Caspofungin, a fungicidal agent that is active against *Candida* biofilm (Bachmann et al., *Antimicrob. Agents Chemother.* 46:3591 (2002) and Kuhn et al., *Antimicrob. Agents Chemother.* 46:1773 (2002)) and the also fungicidal agent amphotericin B were the most active agents tested in prolonging nematode survival to *C. albicans* strain MLR62 (FIG. 17a), *C. krusei* ATCC#6258 (FIG. 17b), *C. parapsilosis* ATCC#20019 (FIGS. 17c and 17d) and *C. albicans* ATCC#90028. In the case of *C. krusei* ATCC#6258, the most resistant to fluconazole among the strains we tested, the difference in survival between fluconazole and caspofungin treated worms was highly significant (P<0.0001), as was the difference between amphotericin B and caspofungin treatments (P=0.0005; FIG. 17b). In the case of *C. parapsilosis* ATCC#20019, caspofungin was significantly more effective than fluconazole (P=0.01), but the difference between amphotericin B and caspofungin was not significant (FIG. 17c). Caspofungin was effective at concentrations as low as 1 µg/ml in the case of *C. albicans* strain MLR62 (P<0.0001). Since filament formation is only seen in dead nematodes, there were significantly fewer nematodes with filaments in the wells that contained antifungal compounds.

Interestingly, at high concentrations, the beneficial effect of fluconazole was lost and the nematodes died faster than non-treated infected worms. Fluconazole up to 32 µg/ml was effective in prolonging survival of nematodes exposed to the fluconazole-susceptible strain *C. parapsilosis* ATCC#20019, but at higher concentrations (100 µg/ml) nematode survival was diminished, even compared to the nematodes in the control group with no antifungals (P=0.01; FIG. 17d). Probably this toxicity is present at even lower concentrations, but the beneficial effect from the antifungal activity outweighs the toxic effect. For example, when nematodes were exposed to the fluconazole-resistant strain *C. krusei* ATCC#6258, fluconazole at 32 µg/ml not only had no effect on nematode survival, but killing in the fluconazole group was significantly faster than untreated worms (P=0.02; FIG. 17b). Similarly, fluconazole at concentrations as low as XYZ µg/ml also decreased the longevity of nematodes feeding only on *E. coli*. Taken together, these observations suggest that the model can be used for the concurrent screen for antifungal activity and host toxicity.

We also evaluated the effect of antifungal agents in reducing fungal burden in the nematode intestine. For example, in one particular experiment, untreated *C. elegans* infected with *C. albicans* MLR62 had an average of 170.8±63.5 colony-forming units (cfu) per worm, whereas caspofungin treated animals (at 8 µg/ml) had almost cleared the infection with an average of 0.3±0.2 cfu per worm (P<0.001). Fluconazole and amphotericin B also significantly decreased the concentration of *Candida* cfu in the nematodes and microscopic examination of the worms confirmed that treatment with antifungals was effective at clearing the worm intestine of visible *Candida* cells (data not shown).

Antifungal Compounds Identified Using the *C. elegans-Candida* Killing Assay

Figure 18:
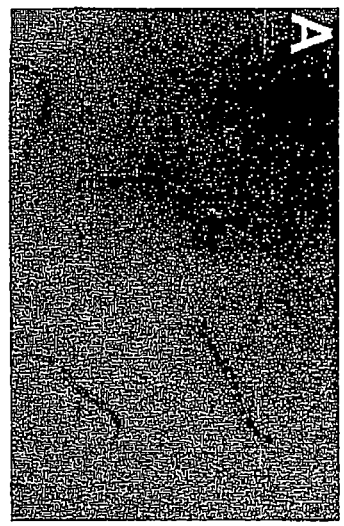
FIGS. 18A through 18C are a series of images showing the phenotype of nematodes exposed to compounds with (FIG. 18A) and without antifungal efficacy (FIGS. 18B and 18C). After exposure to strain *C. albicans* MLR62, *C. elegans* glp-4;sek-1 nematodes were pipetted into 96-well plates that contained compounds from chemical libraries. Nematodes exposed to compounds that had antifungal efficacy (in this case caffeic acid phenethyl ester, CAPE) had no fluorescence within the intestine (FIG. 18A), while nematodes exposed to compounds without antifungal efficacy did not demonstrate any movement (FIG. 18B) and developed filaments outside the nematodes (FIG. 18C). Roughly 25 worms were used per well.
Figure 18:
Figure 18:
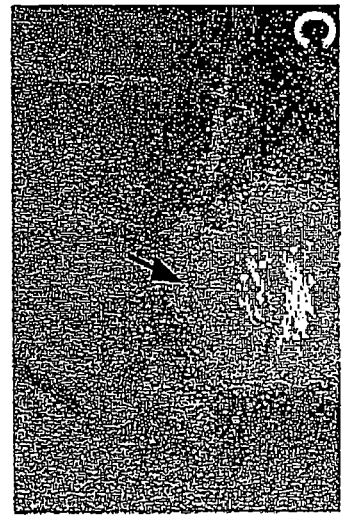

To facilitate adaptation of the *C. elegans-Candida* killing assay to screening chemical libraries for antifungal compounds, we used *C. albicans* strain MLR62 that expresses GFP (linked to the constitutively active TEF1 promoter) and exhibits similar killing kinetics to the parent strain DAY 185 in the *C. elegans* assay. Using this strain, nematodes exposed to compounds that have significant antifungal efficacy exhibit sinusoidal movement and no green fluorescence in the intestine at the endpoint of the assay (FIG. 18a), whereas nematodes exposed to compounds without antifungal efficacy do not demonstrate any movement, are rod-shaped, exhibit high levels of intestinal fluorescence (FIG. 18b), and developed filaments (FIG. 18c).

As an initial test of the *C. elegans-Candida* screening assay, we utilized libraries of compounds made available through the Institute of Chemistry and Cell Biology (ICCB) at Harvard Medical School that includes known compounds that affect diverse cellular pathways as well as US Food and Drug Administration approved drugs that are known to be safe and bioactive in humans. We screened a total of 1,266 compounds (Table 4) and identified 15 (~1.2%) that prolonged nematode survival and completely or almost completely inhibited filamentation. An additional 52 (~4.1%) of the compounds prolonged nematode survival but had no or minimal effect on filamentation (Table 4). To the best of our knowledge, the *C. elegans* screen identified all of the compounds among the 1,266 tested with established, clinically documented antifungal activity against *Candida*. Among the known antifungals, ketoconazole and butoconazole were among the most effective compounds identified (Table 4).

TABLE 4

| Compound | Action/Use | Killing |
| --- | --- | --- |
| Compounds that completely or almost completely inhibited filament formation. | | |
| Caffeic acid phenethyl ester | NFkappaB inhibitor which plays important role in transcription factors pertinent to interleukin 1 action | 0 |
| Ketoconazole | Antifungal | 0.056, 0.167 |
| AG-370 | Belongs to tyrphostin family of tyrosine kinase inhibitors. Inhibits mitogenesis in human fibroblast mediated by platelet derived growth factor | 0.111 |
| Butoconazole nitrate | Antifungal | 0.128 |
| Methscopolamine bromide | Anticholinergic; blocks M1 muscarinic receptors who are present in *Saccharomyces cerevisiae* | 0.167 |
| Lapachol | Antibacterial/Antiparasitic | 0.182 |
| Diethylstilbestrol | Synthetic estrogen; estrogens stimulate colonization of vagina with *Candida albicans* | 0.235 |
| Probucol | Lipid-lowering agent/Antioxidant | 0.278 |
| Sulfabenzamide | Antibiotic | 0.286 |
| Prochlorperazine edisylate | Antiemetic/Antipsychotic; antibacterial activity in vitro | 0.300 |
| Budesonide | Glucocorticoid | 0.385 |
| Cephaloridine | Antibiotic | 0.385 |
| Dyclonine hydrochloride | Local anesthetic; inhibits ergosterol synthesis | 0.444 |
| Flutrimazole | Antifungal | 0.444 |
| Hydroxytacrine maleate | Metabolite of tacrine; tacrine is an acetylcholinesterase inhibitor that is used against Alzheimer's disease; reduces apoptosis in neuronal cells | 0.467 |

TABLE 4-continued

| Compound | Action/Use | Killing |
|---|---|---|
| Compounds that had minimal effect on filament formation | | |
| 5 (S) HPETE | $Ca^{2+}$ channel activation resulting in B-lymphocyte activation | 0.261 |
| Ketorolac tromethamine | Anti-inflammatory | 0.267 |
| Nimodipine | $Ca^{2+}$ channel blocker (L-type)/Probable antioxidant action (see methoxyverapamil) | 0.273 |
| Lipoxin A4 | Product of interaction of 15-HPETE with human leukocytes; anti-inflammatory mediator, suppresses inflammation; inhibits NK cell cytotoxicity | 0.273 |
| N-Arachidonoylglycine | Conjugate of lipids and amino acids; suppresses tonic inflammatory pain in bovine and rat brain; produces endocannabinoid-induced inhibition of T-cell proliferation | 0.275 |
| Lidocaine | $Na^+$ channel blocker; local anesthetic; antiarrhythmic; has antibacterial activity against E. coli, P. aeruginosa, S. aureus in vitro and antifungal activity against C. albicans | 0.286 |
| L-cis-Diltiazem | $Ca^{2+}$ channel blocker; antioxidant | 0.296 |
| AG-1478 | Epidermal growth factor inhibitor; antioxidant | 0.3 |
| 7,7-Dimethyleicosadienoic acid | Probable antioxidant activity | 0.304 |
| MBCQ | Selective inhibitor of cGMP-specific phosphodiesterase | 0.32 |
| 1-Stearoyl-2-linoleoyl-glycerol | Probably enhances the effect of TNF alpha | 0.333 |
| Bafilomycin A1 | Endosomal H(+)-ATPase inhibitor in yeasts; Inhibits TNF-α and expression of metalloproteinases; reduces killing of Aspergillus fumigatus by alveolar macrophages | 0.333 |
| Eicosatrienoic acid (20:3 n-3) | Product of arachidonic acid; induces mitogenesis | 0.333 |
| Farnesylthioacetic acid | Farnesyl derivative; Ras antagonist | 0.343 |
| Niflumic acid | NSAID; inhibits growth of C. albicans via cytosolic acidification and inhibition of glycolysis | 0.355 |
| Siguazodan | Phosphodiesterase III inhibitor; inhibits generation of interleukins-4 and -13 | 0.375 |
| Aminobenzamide (3-ABA) [3-aminobenzamide (3-ABA)] | Tx+ poly(ADP-ribose) synthetase inhibitor; inhibits apoptosis in rat intestinal cells; suppresses inflammatory response and brain injury in experimental E. coli meningitis | 0.389 |
| Acetyl (N) s farnesyl l cys | Inhibitor of isoprenylated protein endoprotease resulting in inhibition of function of ras protein | 0.4 |
| Cefmetazole sodium | Chemotactic agent for neutrophils | 0.4 |
| Glipizide | Sulfonylouria; increases oxidative stress in red cells in vitro | 0.4 |
| Phenylpropanolamine hydrochloride | Catecholamine; inotropic | 0.407 |
| 15 (S) HPETE | Enhances TNF/cycloheximide induced apoptosis, activates caspases-3 and -9 | 0.412 |
| Ascorbic acid | Vitamin C; antioxidant; appears to enhance growth of Cryptococcus neoformans and Candida tropicalis in vitro; enhances neutrophil motility and lymphocyte transformation in vitro and in vivo after infection with Candida albicans | 0.417 |
| FPL-64176 | Induces apoptotic cell death via activation of L-type $Ca^{2+}$ activation | 0.429 |
| Ikarugamycin | Antiprotozoan/Inhibits degradation of CD4 | 0.429 |
| SDZ-201106 | $Na^+$ channel modulator | 0.432 |
| Cytochalasin B | Actin polymerization inhibitor | 0.438 |
| Docosatrienoic acid (22:3 n-3) | Fatty acid; reduces GABA response in rat substantia nigra neurons; is metabolized by fungal lipases to a high-laurate canola oil | 0.439 |
| 3,4-Dichloroisocoumarin | NF-kappaB inhibitor; decreases TNF alpha effect on migration of lymphocytes | 0.444 |
| ALA-ALA-PHE-CMK | Catalytic residue; probably antioxidant | 0.448 |
| Eicosapentaenoic acid (20:5 n-3) | Fatty acid; is metabolized by fungal lipases to a high-laurate canola oil | 0.448 |
| Rolipram | Phosphodiesterase 4A inhibitor; anti-inflammatory; inhibits IL-2R | 0.455 |
| AG-490 | Blocks cell growth and induces apoptosis in human acute lymphocytic leukemia cells; blocks the activity of interleukin-7 in T-lymphocytes | 0.462 |

TABLE 4-continued

| Compound | Action/Use | Killing |
|---|---|---|
| Misoprostol, free acid | Prostaglandin; reverses suppression of TGF-β caused by acetyl salicylic acid; activates protein-kinase A resulting in inhibition of HIV-replication into macrophages | 0.464 |
| Betulinic acid | Inhibits secreted aspartic proteinases of *C. albicans* | 0.483 |
| Leukotriene B4 | Stimulates monocytes, neutrophils and dendritic cell chemotaxis | 0.483 |
| DL-Dihydrosphingosine | Sphingolipid; Probable antibacterial and antifungal activity via inhibition of cell wall | 0.485 |
| N-palmitoyl-L-serine phosphoric acid | Induces platelet aggregation | 0.486 |
| Compounds that had no effect on filament formation | | |
| Butamben | Local anesthetic; contains p-aminobenzoate which decreases the activity of coenzyme Q dependent electron transport | 0.105 |
| Pentolinium bitartrate | Inhibitor of catecholamine secretion | 0.227 |
| Hydrocortisone hemisuccinate | Glucocorticoid | 0.300 |
| Ambroxol hydrochloride | Na$^+$ channel blocker/Pain reliever/Mucolytic agent; promotes microbicidal activity of monocytes; anti-inflammatory activity | 0.303 |
| Clopamide | Thiazide diuretic; enhances oxidative stress | 0.333 |
| Brinzolamide | Antiglaucomatic/Carbonic anhydrase inhibitor; antibacterial | 0.346 |
| Streptomycin sulfate | Antibiotic | 0.364 |
| Benfluorex hydrochloride | Insulin sensitizer; activates transcription factors in *Saccharomyces cerevisiae* | 0.375 |
| Enoxacin | Fluoroquinolone; in vitro synergy with antifungals | 0.379 |
| Practolol | Beta-blocker; enhances free radical production by neutrophils | 0.381 |
| Betamethasone | Glucocorticoid; inhibits glucose-beta-phosphate dehydrogenase, an enzyme present in yeasts | 0.417 |
| Amoxicillin | Antibacterial; enhances colonization of gastrointestinal tract with *Candida* | 0.429 |
| Pregnenolone sulfate, sodium salt | Neurosteroid; induces apoptotic cell death on retinal cells via activation of caspase-2 and -3 and cytochrome c release | 0.438 |
| Clomiphene citrate (Z, E) | Antiestrogen; decreases fatty acid production in *Saccharomyces cerevisiae* | 0.440 |
| Dobutamine hydrochloride | Inotropic agent; stimulates biofilm formation by *Staphylococcus epidermidis* | 0.455 |
| Probenecid | Induces apoptosis | 0.457 |
| Adenosine 5'-monophosphate monohydrate | Induces yeast-mycelium transition in *C. albicans* | 0.471 |
| Azathymine, 6 | Antimetabolite; a derivative of this compound has antibacterial and antifungal activity | 0.480 |
| Benzbromarone | Increases uric acid excretion from kidneys; Probably inhibits apoptosis of proximal tubular renal cells | 0.483 |

Example 5

High-Throughput Chemical Screens Using *Arabidopsis thaliana* Seedlings

We have also developed protocols to perform automated, high-throughput (HT) chemical screens using *Arabidopsis thaliana* (*Arabidopsis*) seedlings as a host. Again, the described methods enable quantitative analyses of a wide range of biological processes such as the response to different types of biotic (pathogens) or abiotic (heavy metals, ultraviolet radiation, heat) stresses that affect viability, as well as other traits. We optimized methods to perform screens in liquid media in 96-well plates.

The exemplary set-up described below highlights key steps in setting up pathogenicity assays with seedlings—all steps of which are amenable to automation, typically using or adapting existing robotics platforms. These examples highlight the ability of this platform to screen using a wide variety of pathogens (in this case the human opportunistic pathogen *P. aeruginosa* and the phytopathogen *P. syringae*—the latter being an example of a bacterial pathogen causing diseases in agricultural setting, are highlighted).

Figure 23:
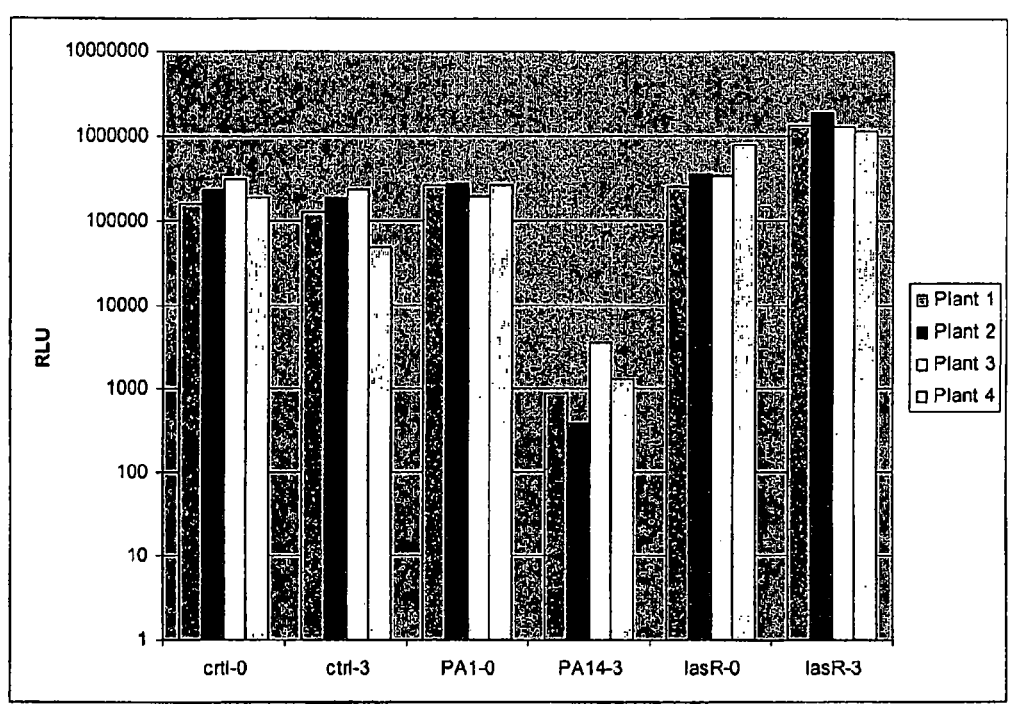
FIG. 23 is a graphical representation of relative luminescent units (RLU) of *Arabidopsis* seedlings ectopically expressing a luciferase reporter from a CaMV 35S promoter. Indicated are RLU just prior to treatment with *P. aeruginosa* (strain PA14) or a mutant impaired in production of some virulence factors—PA 14(lasR) or control untreated seedlings.

For this purpose seeds of an ecotype (natural accession) of *Arabidopsis* that is susceptible to the pathogen being screened is sterilized using standard protocols (soaking in ethanol for 5 minutes followed by 20% bleach treatment for 5 minutes and extensively rinsed with water). These seeds are vernalized at 4° C. for two days and dispensed into 96-well plates with each well containing 100 µl MS (Murashige and Skoog) medium and covered with transparent lids and edges sealed with Parafilm. The seeds are germinated and grown with 50 µE fluorescent light at 22° C. with replacement of medium at day 8 and subsequently inoculated with the bacterial pathogen on day 10. In order to highlight a strategy for automated quantitative read-out of the extent of disease in one case (FIG. 23), seeds from a transgenic *Arabidopsis* plant expressing a luminescent reporter (luciferase) was used. For other screens using certain pathogens, the use of mutants in known defense pathways (such as but not limited to npr1, pad4, sid2 (ics1), ein2, jar1) might make the disease symptoms and the read-out used more robust.

Bacteria are grown in appropriate medium—King's Broth in the case of *Pseudomonas syringae* pv. *tomato* DC3000 or a mutant derivative with an insertion in the hrcC gene-DC3000 (hrcC) at 30° C. or LB in the case of *E. coli* strain DH5α, *P. aeruginosa* (strain PA14) or a mutant derivative of PA14 with a deletion in a regulatory gene lasR-PA14(lasR). These mutants serve to highlight examples of genes that are important for pathogenesis in relevant hosts and when impaired do indeed show attenuated disease symptoms.

Because the dispensing of seeds is a labor-intensive step, we collaborated with Union Biometrica, Inc. to test their robotic equipment COPAS XL to do this step automatically. These tests revealed that single seeds could be dispensed into microplate wells with over 99% accuracy. The equipment used for this purpose has a higher size exclusion diameter than the COPAS BioSort robot described above used to dispense *C. elegans*, thus allowing the sorting and dispensing of appropriately sized larvae as well as *Arabidopsis* seeds for the organisms described in Example 6. The addition of media and compounds, and replacement or media can be done using standard liquid handling devices available in the market.

Figure 21:
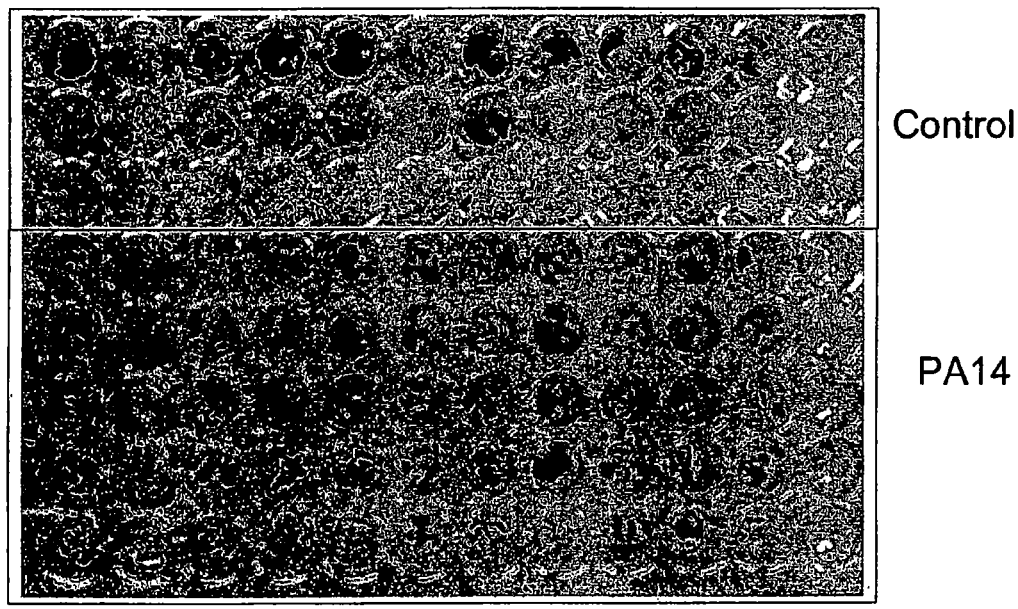
FIG. 21 is an image depicting near complete killing of seedlings in a 96-well plate assay of *Arabidopsis* (Col ecotype) seedlings by *Pseudomonas aeruginosa* (strain PA 14) compared to much healthier (and greener) control seedlings five days post infection.
Figure 22:
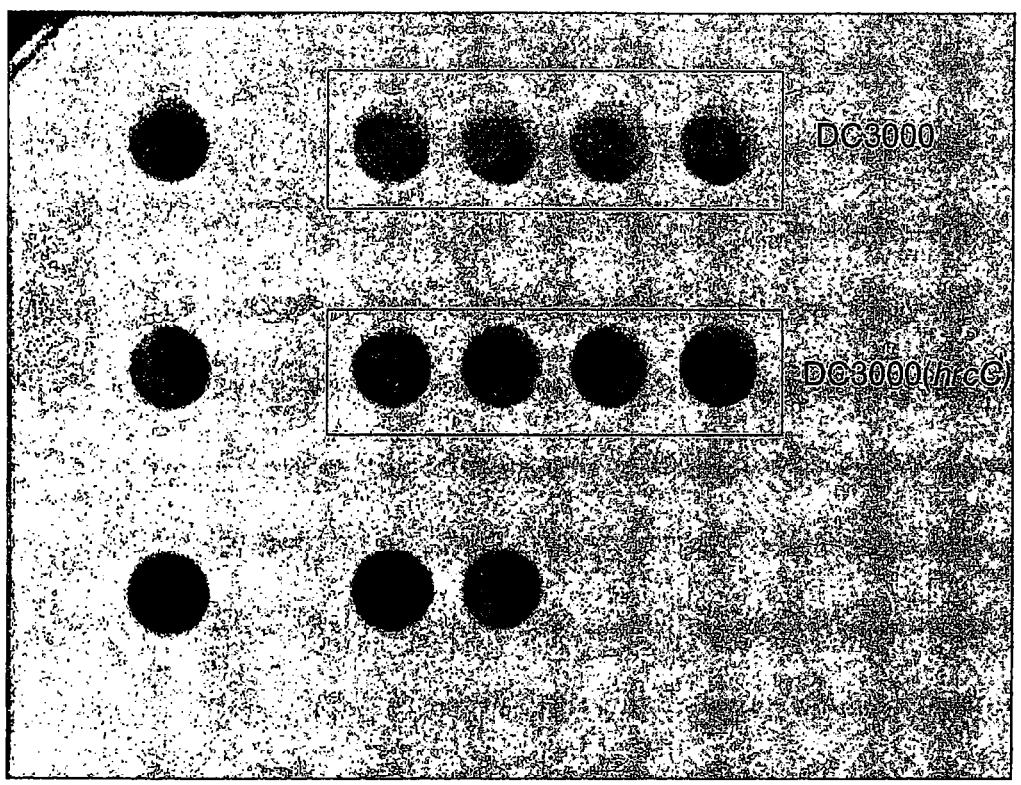
FIG. 22 is an image depicting damage to *Arabidopsis* (Col ecotype) seedlings by a plant pathogen *Pseudomonas syringae* pv. *tomato* (DC3000) and much healthier seedlings (compared to control untreated seedlings) by the type III secretion mutant DC3000(hrcC) five days post infection. The treated seedlings are boxed and labeled.

Bacteria were added to ten-day old seedlings and the plates covered and sealed at the edges as before and were placed at 25° C. at 50 µE light as before. FIGS. 21 and 22 display visual phenotypes (i.e., extent of disease and damage to seedlings). As can be seen in these figures both these pathogens (PA 14 and DC3000) cause extensive damage to the seedlings, while a less pathogenic bacterium such as *E. coli* DH5α causes lesser seedling damage and disease symptoms progress much more slowly (not shown). A key regulatory mutant of PA14 (lasR) that impairs the synthesis and secretion of several virulence factors (not shown) and the hrcC mutant of DC3000-DC3000 (hrcC) which knocks out the key type III secretion mechanism important for the delivery of many virulence effectors into the host cell cause significantly less damage (FIG. 22). These results highlight the relevance and use of this system to identify anti-infectives using a chemical screen in this platform.

Another key aspect for high throughput screening is the need for readouts that are indicators of damage to the host (seedlings) that can be either automated using a quantitative assay (preferably) or a reproducible qualitative assay. One way would be to adapt a live/dead stain such as Sytox® described herein in the context of the *C. elegans* screens. Alternatively, one can use fluorescent or luminescent markers expressed ectopically using constitutive promoters that could be read in multi-well plate readers.

As a proof-of-principle seedlings expressing luciferase constitutively from a CaMV 35S promoter were used in the assay and the seedling luminescence was read on Day 0 and Day 3—well before symptoms are visually obvious, using a multi-well luminometer (TopCount, Perkin Elmer). As can be seen in the graph shown in FIG. 23, the luminescence was almost abrogated by day 3 (about a 3 log reduction in relative luminescence units), indicative of poor seedling health in the case of wild-type PA14, whereas the control untreated plants and the seedlings exposed to the PA14 (lasR) mutant either did not decrease or increased in luminescence compared to day 0, respectively.

Example 6

Other Organisms for Identifying Antimicrobial or Antiviral Compounds as Well as Compounds that Increase Longevity

*Drosophila melanogaster* (Fruit Fly)

The fruit fly, *Drosophila melanogaster*, may also be used in the methods described herein (for instance in Example 1) for identifying antimicrobial or antiviral compounds, as well as compounds that increase lifespan.

Fly stocks of, e.g., OregonR or the marked strain yellow white (yw) are cultured under standard conditions on corn meal medium. Cultures of *P. aeruginosa* strain, PA14, and the control, *E. coli* DH5a, are grown overnight in King's B medium (King et al. (1954) *J. Lab Clin. Med.* 44:301-307). Following overnight culturing, the cells are diluted 1/10 and grown for an additional four to five hours. The cells are subsequently washed twice, resuspended in distilled water, and then added to the corn meal medium. As such, the pathogen, e.g., *P. aeruginosa*, is introduced into the fly larvae by ingestion. Alternatively, direct injection of the pathogen into an appropriately staged larva (e.g., first, second, or third instar) may also be used.

Following bacterial infection, the fly larvae are placed in, e.g., 24-well, 48-well, 96-well, or 384-well microtiter plates, each well containing liquid media and the compound or compounds to be tested, incubated at 18° C. to 28° C., and monitored for death as assayed by a lack of movement.

*Galleria mellonella* (Greater Wax Moth)

The larvae of *Galleria mellonella* (greater wax moth) may also be used in the screening methods described herein.

A pathogen, e.g., *Pseudomonas aeruginosa*, is injected into *G. mellonella* larvae as follows. Cultures of *P. aeruginosa* are grown overnight in King's B medium (King et al. (1954) *J. Lab. Clin. Med.* 44:301-307). This culture is then diluted 1:100 in the same medium and cultured. After two hours of growth, the cultures are harvested by centrifugation, and the cells are resuspended in an equal volume of 10 mM MgSO$_4$. Each culture is subsequently diluted to an OD$_{600}$ of 0.1 (approximately $10^8$ cells/ml). Using a Hamilton syringe, five microliter volumes of serial 10-fold dilutions ($10^0$ to $10^{-6}$) are injected into one of the abdominal parapodia of *G. mellonella* (Lysenko (1963) *Journal of Insect Pathology*, 5:78-82). Bacterial counts are determined by plating according to standard methods. *G. mellonella* larvae are purchased from Van der Horst Wholesale, St. Mary's, OH.

After injection of bacteria, *G. mellonella* larvae are placed in, e.g., 24-well microtiter plates, each well containing liquid media and the compound or compounds to be tested, and incubated at 25° C. Lethality is visually assessed after forty-eight hours by monitoring the color change (from white to black) of each larva, and by determining larval motility. Each single non-motile black larva is scored as dead.

*Plutella xylostella* (Diamondback Moth)

The larvae of *Plutella xylostella* (diamondback moth) may also be used in the screening methods described herein.

Larvae of *Plutella xylostella* are fed mustard leaves infiltrated with *Pseudomonas aeruginosa* as follows. *P. aeruginosa* was cultured in King's B medium (King et al. (1954) *J. Lab. Clin. Med.* 44:301-307). Overnight cultures are pelleted in a microcentrifuge and were then washed twice in 10 mM MgSO$_4$. Cells are then resuspended in 10 mM MgSO$_4$ and are diluted to an OD$_{600}$ of 0.1. *Pl. xylostella* larvae are maintained on a semisynthetic wheat germ based diet according to standard methods (Shelton et al. (1991) *J. Ent. Sci.*, 26:17-26).

Mustard greens (available from grocery stores) are cut into pieces of about 10 $cm^2$ and are submersed in 10 mM $MgSO_4$ containing *P. aeruginosa*. The submersed leaves are placed under vacuum, and the vacuum is released suddenly to infiltrate the bacterial solution into the leaves. As a control, leaves are also infiltrated with only 10 mM $MgSO_4$. Infiltrated leaf material is incubated at 23° C. in a petri dish with twenty *Pl. xylostella* larvae, which are allowed to feed at will. After feeding, *Pl. xylostella* larvae are placed in, e.g., 24-well or 48-well microtiter plates, each well containing liquid media and the compound or compounds to be tested, and incubated at 25° C. Deceased larvae are scored after forty-eight hours. Larvae which do not move after being touched with a pipette tip are scored as dead.

Other Embodiments

All publications, patents, and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

What is claimed is:

1. A method of treating a Gram-positive bacterial infection in a subject in need thereof, said method comprising administering to said subject a pharmaceutical composition comprising a compound of formula III:

(III)

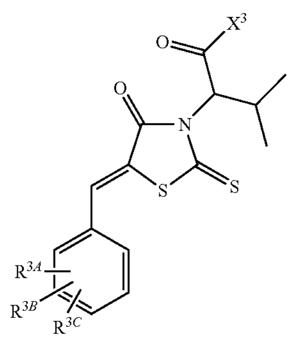

, or a salt thereof, and a pharmaceutically acceptable excipient, wherein each of $R^{3A}$, $R^{3B}$, and $R^{3C}$ is, independently, selected from H, halide, nitro, $C_{1-4}$ alkyl, $C_{2-4}$ alkenyl, $C_{2-4}$ alkynyl, $OR^{3G}$, $OC(O)R^{3H}$, $NR^{3I}R^{3J}$, $NHC(O)R^{3K}$, $NHC(S)R^{3L}$, $NHC(O)OR^{3M}$, $NHC(S)OR^{3N}$, $NHC(O)NHR^{3O}$, $NHC(S)NHR^{3P}$, $NHC(O)SR^{3Q}$, $NHC(S)SR^{3R}$, $NHS(O)_2R^{3S}$, $C(O)OR^{3T}$, and $C(O)NHR^{3U}$;

$X^3$ is independently selected from $OR^{3G}$, $OC(O)R^{3H}$, $NR^{3I}R^{3J}$, $NHC(O)R^{3K}$, $NHC(S)R^{3L}$, $NHC(O)OR^{3M}$, $NHC(S)OR^{3N}$, $NHC(O)NHR^{3O}$, $NHC(S)NHR^{3P}$, $NHC(O)SR^{3Q}$, $NHC(S)SR^{3R}$, and $NHS(O)_2R^{3S}$; and each of $R^{3G}$, $R^{3H}$, $R^{3I}$, $R^{3J}$, $R^{3K}$, $R^{3L}$, $R^{3M}$, $R^{3N}$, $R^{3O}$, $R^{3P}$, $R^{3Q}$, $R^{3R}$, $R^{3S}$, $R^{3T}$, and $R^{3U}$ is, independently, selected from H, $C_{1-4}$ alkyl, $C_{2-4}$ alkenyl, $C_{2-4}$ alkynyl, $C_{2-6}$ heterocyclyl, $C_{6-12}$ aryl, $C_{7-14}$ alkaryl, $C_{3-10}$ alkheterocyclyl, and $C_{1-4}$ heteroalkyl, wherein said pharmaceutical composition is administered in an amount effective to treat said Gram-positive bacterial infection and wherein said Gram-positive bacterial infection is selected from the group consisting of community-acquired pneumonia, upper and lower respiratory tract infection, skin and soft tissue infection, bone and joint infection, hospital-acquired lung infection, acute bacterial otitis media, bacterial pneumonia, complicated infection, noncomplicated infection, pyelonephritis, intra-abdominal infection, deep-seated abscess, central nervous system infection, wound infection, peritonitis, meningitis, infections after burn, urogenital tract infection, gastro-intestinal tract infection, pelvic inflammatory disease, endocarditis, and intravascular infection.

2. The method of claim 1, wherein said compound of formula III is selected from the group consisting of

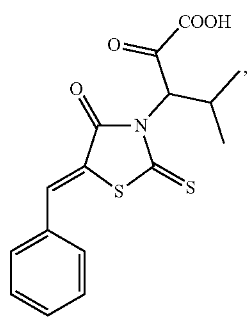

,

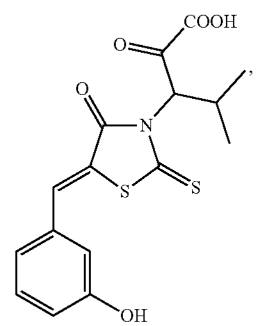

,

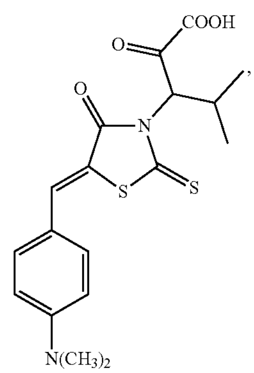

,

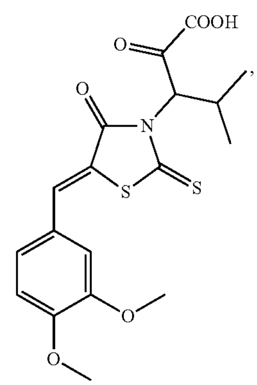

,

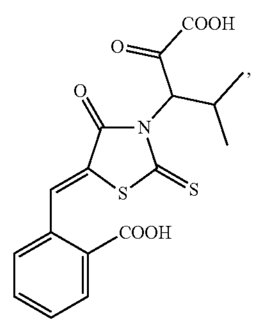

,

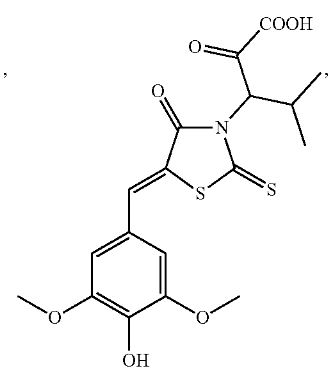

,

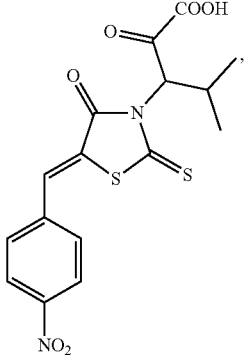
and a salt thereof.
* * * * *